(12) United States Patent
Cool et al.

(10) Patent No.: US 10,723,813 B2
(45) Date of Patent: Jul. 28, 2020

(54) PDGF-B /PDGF-BB BINDING VARIANTS OF HEPARAN SULFATES

(71) Applicant: Agency for Science, Technology and Research, Singapore (SG)

(72) Inventors: Simon Cool, Singapore (SG); Victor Nurcombe, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 22 days.

(21) Appl. No.: 15/542,123

(22) PCT Filed: Jan. 8, 2016

(86) PCT No.: PCT/SG2016/050008
§ 371 (c)(1),
(2) Date: Jul. 7, 2017

(87) PCT Pub. No.: WO2016/111651
PCT Pub. Date: Jul. 14, 2016

(65) Prior Publication Data
US 2018/0258193 A1    Sep. 13, 2018

(30) Foreign Application Priority Data
Jan. 9, 2015  (SG) .......................... 10201500182X

(51) Int. Cl.
| | | |
|---|---|---|
| C08B 37/00 | (2006.01) |
| A61K 31/727 | (2006.01) |
| A61K 38/18 | (2006.01) |
| A61P 17/02 | (2006.01) |
| A61K 45/06 | (2006.01) |
| A61L 33/00 | (2006.01) |

(52) U.S. Cl.
CPC ........ *C08B 37/0075* (2013.01); *A61K 31/727* (2013.01); *A61K 38/1858* (2013.01); *A61K 45/06* (2013.01); *A61L 33/0011* (2013.01); *A61P 17/02* (2018.01); *C08B 37/0078* (2013.01); *C08B 37/0081* (2013.01); *A61L 2300/42* (2013.01); *A61L 2400/18* (2013.01)

(58) Field of Classification Search
CPC ............ C08B 37/0075; C08B 37/0078; A61K 31/727; A61K 38/1858; A61L 27/227; A61L 27/34; A61P 17/02
See application file for complete search history.

(56) References Cited

U.S. PATENT DOCUMENTS

| 9,498,494 B2 | 11/2016 | Cool et al. |
| 2008/0274156 A1 | 11/2008 | Nurcombe et al. |
| 2017/0043053 A1 | 2/2017 | Cool et al. |
| 2017/0106012 A1 | 4/2017 | Cool et al. |
| 2018/0142792 A1 | 5/2018 | Feller et al. |

FOREIGN PATENT DOCUMENTS

| EP | 0243179 A1 * | 10/1987 | ............. A61K 38/39 |
| EP | 3 137 509 A1 | 3/2017 | |
| WO | WO-93/19096 A1 | 9/1993 | |
| WO | WO-99/21588 A1 | 5/1999 | |
| WO | WO-2010/029278 A2 | 3/2010 | |
| WO | WO-2010029278 A2 * | 3/2010 | ......... A61K 38/1875 |
| WO | WO-2011/062561 A1 | 5/2011 | |
| WO | WO-2015/167401 A1 | 11/2015 | |

OTHER PUBLICATIONS

Li, B. et al "The effect of the local delivery of platelet-derived growth factor . . . " Biomater., vol. 30, pp. 3486-3494. (Year: 2009).*
Abramsson, A. et al., Defective N-sulfation of heparan sulfate proetoglycans limits PDGF-BB binding and pericyte recruitment in vascular development, Genes & Development, 21:316-331 (2007).
Ackermann, M. et al., Priming with proangiogenic growth factors and endothelial progenitor cells improves revascularization in linear diabetic wounds, International Journal of Molecular Medicine, 33(4):833-839 (2014).
Brickman, T.G. et al., Structural Modification of Fibroblast Growth Factor-binding Heparan Sulfate at a Determinative Stage of Neural Development, The Journal of Biological Chemistry, 273(8):4350-4359 (1998).
Feyzi, E. et al., Characterization of Heparin and Heparan Sulfate Domains Binding to the Long Splice Variant of Platelet-derived Growth Factor A Chain, The Journal of Biological Chemistry, 272(9):5518-5524 (1997).
Garcia-Filipe, S. et al., RGTA OTR4120, a heparan sulfate mimetic, is a possible long-term active agent to heal burned skin, Journal of Biomedical Materials Research Part A, 80(1):75-84 (2007).
Gotha, L. et al., Heparan sulfate side chains have a critical role in the inhibitory effects of perlecan on vascular smooth muscle cell response to arterial injury, Am J Physiol Heart Circ Physiol, 307:H337-H345 (2014).
International Search Report for PCT/SG16/50008, 7 pages (dated Feb. 29, 2016).
Knobloch, J.E. and Shaklee, P.N., Absolute Molecular Weight Distribution of Low-Molecular-Weight Heparins by Size-Exclusion Chromatography with Multiangle Laser Light Scattering Detection, Analytical Biochemistry, 245:231-241 (1997).
Kurup, S. et al., Heparan sulphate requirement in platelet-derived growth factor B-mediated pericyte recruitment, Biochemical Society Transactions, 34(3):454-455 (2006).

(Continued)

*Primary Examiner* — Leigh C Maier
(74) *Attorney, Agent, or Firm* — Choate, Hall & Stewart, LLP; Kristen C. Buteau; Nicholas J. Pace

(57) ABSTRACT

Affinity purification of platelet-derived growth factor-binding heparan sulphate from porcine mucosa (HS6) is disclosed. Also disclosed is the use of HS6 in repair and regeneration of the skin for treating wounds, burns, ulcers and other skin injuries.

22 Claims, 39 Drawing Sheets
Specification includes a Sequence Listing.

(56) References Cited

OTHER PUBLICATIONS

Lee, J. et al., The effect of controlled release of PDGF-BB from heparin-conjugated electrospun PCL/gelatin scaffolds on cellular bioactivity and infiltration, Biomaterials, 33:6709-6720 (2012).

Ofosu, F.A. et al., Increased sulphation improves the anticoagulant activities heparan sulphate and dermatan sulphate, Biochem. J., 248:889-896 (1987).

Okolicsanyi, R.K. et al., Heparan sulfate phteoglycans and human breast cancer epithelial cell tumorigenicity, J Cell Biochem, 115(5):967-976 (2014).

Raines, E.W. and Ross, R., Compartmentalization of PDGF on Extracellular Binding Sites Dependent on Exon-6-Encoded Sequences, The Journal of Cell Biology, 116(2):533-543 (1992).

Rolny, C. et al., Heparin Amplifies Platelet-derived Growth Factor (PDGF)-BB-induced PDGF alpha-Receptor but Not PDGF beta-Receptor Tyrosine Phosphorylation in Heparan Sulfate-deficient Cells, The Journal of Biological Chemistry, 277(22):19315-19321 (2002).

Rozman, P. and Bolta, Z., Use of platelet growth factors in treating wounds and soft-tissue injuries, Acta Dermatoven APA, 16(4):156-165 (2007).

Skidmore, M.A. et al., Disaccharide compositional analysis of heparan sulfate and heparin polysaccharides using UV or high-sensitivity fluorescence (BODIPY) detection, Nature Protocols, 5(12):1983-1992 (2010).

Tong, M. et al., Diabetes-Impared Wound Healing Is Improved by Matrix Therapy With Heparan Sulfate Glycosaminoglycan Mimetic OTR4120 in Rats, Diabetes, 61(10):2633-2641 (2012).

Written Opinion for PCT/SG16/50008, 6 pages (dated Feb. 29, 2016).

* cited by examiner

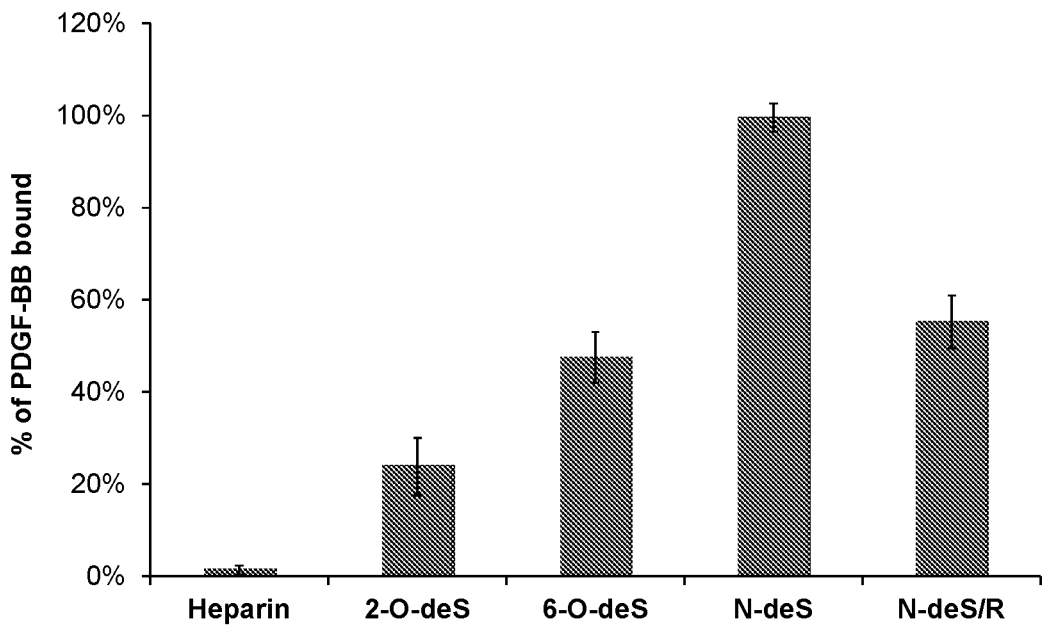

Figure 6

PDGF-B sequence: 241 aa
MNRCWALFLSLCCYLRLVSAEGDPIPE
ELYEMLSDHSIRSFDDLQRLLHGDPGE
EDGAELDLNMTRSHSGGELESLARGR
RSLGSLTIAEPAMIAECKTRTEVFEISR
RLIDRTNANFLVWPPCVEVQRCSGCC
NNRNVQCRPTQVQLRPVQVRKIEIVR
KKPIFKKATVTLEDHLACKCETVAAARP
VTRSPGGSQEQR**AKTPQTRVTIRTVR
VRRPPKGKHRKFKHTHDK**TALKETLG
A

**Biotin –
RAKTPQTRVTIRTVRVRRPPKGKHRK
FKHTHDK**

33 aa peptide

Figure 7

↑ neutrophils

HS6+

↑ blood vessels
↑ matrix deposition

| Sample | µg | | % normalised | |
| --- | --- | --- | --- | --- |
| | >2dp | 2dp | >2dp | 2dp |
| HS starting material | 20.9 | 54.7 | 27.7 | 72.3 |
| | 20.2 | 55.3 | 26.8 | 73.2 |
| HS6 +ve | 18.0 | 49.5 | 26.7 | 73.3 |
| | 16.6 | 49.3 | 25.2 | 74.8 |
| HS6 -ve | 10.3 | 38.0 | 21.3 | 78.7 |
| | 16.2 | 42.5 | 27.6 | 72.4 |

Figure 26

|  | % disaccharide | | | | | | |
|---|---|---|---|---|---|---|---|
|  | ΔUA-GlcNAc | ΔUA-GlcNS | ΔUA-GlcNAc,6S | ΔUA,2S-GlcNAc | ΔUA-GlcNS,6S | ΔUA,2S-GlcNS | ΔUA,2S-GlcNS,6S |
| Celsus HS 10697 | 33.6 | 26.4 | 11.9 | 0.5 | 10.6 | 6.4 | 10.7 |
|  | 33.5 | 26.2 | 12.2 | 0.6 | 10.5 | 6.4 | 10.7 |
|  | 33.7 | 26.4 | 11.9 | 0.5 | 10.5 | 6.4 | 10.6 |
|  | 33.5 | 26.4 | 12.2 | 0.6 | 10.5 | 6.4 | 10.5 |
| Average | 33.6 | 26.4 | 12.1 | 0.6 | 10.5 | 6.4 | 10.6 |
| HS6 +ve | 31.6 | 24.5 | 12.2 | 0.5 | 11.6 | 6.8 | 12.8 |
|  | 31.6 | 24.5 | 12.2 | 0.5 | 11.6 | 6.7 | 13.0 |
|  | 31.4 | 24.5 | 12.0 | 0.5 | 11.8 | 6.8 | 13.0 |
|  | 31.6 | 24.6 | 12.0 | 0.5 | 11.6 | 6.8 | 12.8 |
| Average | 31.6 | 24.5 | 12.1 | 0.5 | 11.7 | 6.8 | 12.9 |
| HS6 -ve | 36.4 | 29.4 | 11.6 | 0.5 | 9.2 | 6.3 | 6.7 |
|  | 36.6 | 29.6 | 11.5 | 0.6 | 8.9 | 6.3 | 6.6 |
|  | 36.5 | 29.4 | 11.6 | 0.5 | 9.1 | 6.2 | 6.7 |
|  | 36.5 | 29.4 | 11.3 | 0.6 | 9.0 | 6.2 | 7.0 |
| Average | 36.5 | 29.5 | 11.5 | 0.6 | 9.1 | 6.3 | 6.8 |

Figure 27

PDGF-B /PDGF-BB BINDING VARIANTS OF HEPARAN SULFATES

FIELD OF THE INVENTION

The present invention relates to heparan sulphates that bind PDGF-B or PDGF-BB, and to their use in wound healing, including the repair and/or regeneration of skin.

BACKGROUND TO THE INVENTION

Skin constitutes the largest organ of the human body, serving as a protective barrier against physical injury, radiation and temperature. Skin consists of an underlying mesenchymal (dermal) layer and an outer epithelial (epidermal) layer.

Skin wound healing is regulated by various mechanisms including cell-cell interactions, extracellular matrix production and a number of cytokines and growth factors (see Paul Martin. Wound Healing—Aiming for Perfect Skin Regeneration. Science 276 (75) 1997). Important aims of wound treatment include rapid wound closure and a functionally and aesthetically satisfactory scar.

Wound healing in skin proceeds via an overlapping pattern of events including coagulation, inflammation, tissue formation (epithelialization, formation of granulation tissue, matrix) and tissue remodeling. PDGF BB is implicated in the processes of inflammation, granulation, tissue formation, re-epithelization, matrix formation and remodeling. The process of repair is mediated in large part by interacting molecular signals, primarily cytokines. Initial injury triggers coagulation and an acute local inflammatory response followed by mesenchymal stem cell recruitment, proliferation and matrix synthesis. Failure to resolve the inflammation can lead to chronic non healing wounds, whereas uncontrolled matrix accumulation, can lead to excess scarring.

One of the major growth factors known to be crucial for wound healing is platelet-derived growth factor (PDGF), a family of heparin-binding proteins made by many types of cell, including platelets, macrophages, smooth muscle and endothelial cells. The PDGF-BB (homodimer of PDGF-B) variant is the only growth factor approved by the Food and Drug Administration (FDA) for the treatment of non-healing diabetic ulcers. However, excessive usage of PDGF-BB has been linked to an increased risk of cancer.

Glycosaminoglycans are complex, linear, highly charged carbohydrates that interact with a wide range of proteins to regulate their function; they are usually synthesized attached to core protein. GAGs are classified into nonsulfated (HA) and sulfated (CS, DS, KS, heparin and HS).

Among the GAGs, the heparan sulfate (HS) family is of particular interest because of its ability to interact with targeted proteins based on specific sequences within its domains. The family (heparin and HS) consist of repeating uronic acid-(1→4)-D-glucosamine disaccharide subunits with variable pattern of N-, and O-sulfation. For example, the anti-coagulant activity of heparin requires 3O-sulfation in glucosamine residue with a unique pentasaccharide arrangement (Lindahl U, Backstrom G, Hook M, Thunberg L, Fransson L A, Linker A. Structure of the antithrombin-binding site in heparin Proc Natl Acad Sci USA. 1979; 76:3198-202.). A unique sulfation pattern is also apparent for ECM proteins; an avid heparin-binding variant that binds FN is particularly highly charged, with 7 to 8 N-sulfated disaccharides being required, and with a larger domain than usual (>14 residues) (Falcone D J, Salisbury B G J. Fibronectin stimulates macrophage uptake of low-density lipoprotein-heparin-collagen complexes Arteriosclerosis. 1988; 8:263-73; Mahalingam Y, Gallagher J T, Couchman J R. Cellular adhesion responses to the heparin-binding (HepII) domain of fibronectin require heparan sulfate with specific properties. J Biol Chem. 2007; 282:3221-30). However, HS differs from such sulfated heparins by having highly sulfated NS domains separated by unsulfated NA domains; such dispositions provide unique arrangements for selectively binding proteins, without the side effects of heparin (Gandhi N S, Mancera R L. The Structure of Glycosaminoglycans and their Interactions with Proteins. Chem Biol Drug Des. 2008; 72:455-82.).

The disaccharide composition of HS can be elucidated through a series of enzymatic cleavages (Venkataraman G, Shriver Z, Raman R, Sasisekharan R. Sequencing complex polysaccharides. Science. 1999; 286:537-42; Desai U R, Wang H M, Linhardt R J. Specificity studies on the heparin lyases from *Flavobacterium*-heparinum Biochemistry. 1993; 32:8140-5; Shriver Z, Sundaram M, Venkataraman G, Fareed J, Linhardt R, Biemann K, et al. Cleavage of the antithrombin III binding site in heparin by heparinases and its implication in the generation of low molecular weight heparin. Proc Natl Acad Sci USA. 2000; 97:10365-70) using the *Flavobacterium heparinium* enzymes heparinase I, II and III to cleave the glycosidic bonds. More than 90% depolymerization of heparin or HS is possible when all 3 heparinases are used in combination (Karamanos N K, Vanky P, Tzanakakis G N, Tsegenidis T, Hjerpe A. Ion-pair high-performance liquid chromatography for determining disaccharide composition in heparin and heparan sulphate. J Chromatogr A. 1997; 765:169-79; Vynios D H, Karamanos N K, Tsiganos C P. Advances in analysis of glycosaminoglycans: its application for the assessment of physiological and pathological states of connective tissues. J Chromatogr B. 2002; 781:21-38.). The resulting disaccharide mixtures can be analyzed by PAGE (Hampson I N, Gallagher J T. Separation of radiolabeled glycosaminoglycan oligosaccharides by polyacrylamide-gel electrophoresis Biochem J. 1984; 221:697-705), SAX-H PLC (Skidmore M A A, Yates E and Turnbull J E. Labelling heparan sulfate saccharides with chromophore, fluorescence and mass tag for HPLC and MS separations. Methods in Molecular biology. 2009; 534: 157-69), or highly sensitive capillary electrophoresis (CE) (Lamari F, Militsopoulou M, Gioldassi X, Karamanos N K. Capillary electrophoresis: a superior miniaturized tool for analysis of the mono-, di-, and oligosaccharide constituents of glycan moieties in proteoglycans. Fresenius J Anal Chem. 2001; 371:157-67; Karamanos N K, Vanky P, Tzanakakis G N, Hjerpe A. High performance capillary electrophoresis method to characterize heparin and heparan sulfate disaccharides. Electrophoresis. 1996; 17:391-5; Sudhalter J, Folkman J, Svahn C M, Bergendal K, Damore P A. Importance of size, sulfation, and anticoagulant activity in the potentiation of acidic fibroblast growth-factor by heparin J Biol Chem. 1989; 264:6892-7; Militsopoulou M, Lamari F N, Hjerpe A, Karamanos N K. Determination of twelve heparin- and heparan sulfate-derived disaccharides as 2-aminoacridone derivatives by capillary zone electrophoresis using ultraviolet and laser-induced fluorescence detection. Electrophoresis. 2002; 23:1104-9) by comparison to known disaccharides standards.

SUMMARY OF THE INVENTION

The present invention concerns a heparan sulphate species and heparan sulphate preparations comprising or consisting of the heparan sulphate species. The heparan sulphate species is called HS6 (or HS6+). HS6 refers to a novel class of structurally and functionally related isolated heparan sulphate.

HS6 has been found to bind PDGF-B and/or PDGF-BB. HS6 has also been found to enhance the proliferation of human dermal fibroblasts in vitro, enhance migration of human dermal fibroblasts in an in vitro model of wound healing, and enhance wound healing in vivo. HS6 has also been found to increase/enhance binding of PDGF-BB to PDGFRβ.

In one aspect of the present invention a heparan sulphate HS6 is provided. HS6 may be provided in isolated form or in substantially purified form. This may comprise providing a composition in which the heparan sulphate component is at least 80% HS6, more preferably one of at least 85%, 90%, 95%, 96%, 97%, 98%, 99% or 100%.

In preferred embodiments, HS6 is capable of binding a peptide or polypeptide having the amino acid sequence of RAKTPQTRVTIRTVRVRRPPKGKHRKFKHTHDK (SEQ ID NO: 1). The peptide may have one or more additional amino acids at one or both ends of this sequence. For example, the peptide may have any of 1, 2, 3, 4, 5, 6, 7, 8, 9, 10, 11, 12, 13, 14, 15, 16, 17, 18, 19, 20 or more amino acids at one or both end of this sequence.

In other embodiments the polypeptide is a PDGF-B or PDGF-BB protein. In some embodiments HS6 binds to a peptide having or consisting of the amino acid sequence of SEQ ID NO:1 or PDGF-B or PDGF-BB protein with a $K_D$ of less than 100 µM, more preferably less than one of 50 µM, 40 µM, 30 µM, 20 µM, 10 µM, 1 µM, 100 nM, 50 nM, 10 nM or 1 nM.

HS6 may be obtained, identified, isolated or enriched according to the inventors' methodology described herein, which may comprise the following steps:

(i) providing a solid support having polypeptide molecules adhered to the support, wherein the polypeptide comprises a heparin-binding domain having the amino acid sequence of RAKTPQTRVTIRTVRVRRPPKGKHRKFKHTHDK (SEQ ID NO: 1);
(ii) contacting the polypeptide molecules with a mixture comprising glycosaminoglycans such that polypeptide-glycosaminoglycan complexes are allowed to form;
(iii) partitioning polypeptide-glycosaminoglycan complexes from the remainder of the mixture;
(iv) dissociating glycosaminoglycans from the polypeptide-glycosaminoglycan complexes;
(v) collecting the dissociated glycosaminoglycans.

In the inventors' methodology the mixture may comprise glycosaminoglycans obtained from commercially available sources. One suitable source is a heparan sulphate fraction, e.g. a commercially available heparan sulphate. One suitable heparan sulphate fraction can be obtained during isolation of heparin from porcine intestinal mucosa, another is heparan sulphate from porcine mucosa [$HS^{PM}$] (e.g. from Celsus Laboratories Inc.—sometimes called "Celsus HS").

Other suitable sources of heparan sulphate include heparan sulphate from any mammal (human or non-human), particularly from the kidney, lung or intestinal mucosa. In some embodiments the heparan sulphate is from pig (porcine) or cow (bovine) intestinal mucosa, kidney or lung.

In another aspect of the present invention a composition comprising HS6 according to any one of the aspects above and PDGF-B or PDGF-BB protein is provided. The composition may comprise isolated PDGF-B, PDGF-BB, or a heterodimer comprising PDGF-B, and isolated HS6. The composition may be a PDGF-B preparation comprising PDGF-B, PDGF-BB, or a heterodimer comprising PDGF-B, and isolated HS6 in a container. A suitable container may be a bottle, vial, tube or syringe, and may optionally be sterile.

In one aspect of the present invention a pharmaceutical composition or medicament is provided comprising HS6 in accordance with the aspects described above. The pharmaceutical composition or medicament may further comprise a pharmaceutically acceptable carrier, adjuvant or diluent. In some embodiments the pharmaceutical composition or medicament may further comprise PDGF-B or PDGF-BB protein.

In some embodiments the pharmaceutical composition is for use in a method of medical treatment. The method may comprise wound healing in vivo, the repair and/or regeneration of tissue, e.g. skin, dermal or epithelial tissue, or the repair and/or regeneration of skin.

In another aspect of the present invention HS6 is provided for use in a method of medical treatment. The method of medical treatment may comprise a method of wound healing in vivo, the repair and/or regeneration of tissue, or the repair and/or regeneration of skin. Such repair and/or regeneration may be in a mammal or a human.

In a related aspect of the present invention the use of HS6 in the manufacture of a medicament for use in a method of medical treatment is provided. In some embodiments the method of medical treatment comprises wound healing in vivo or the repair and/or regeneration of tissue as described above.

In one aspect of the present invention Heparan Sulphate HS6 is provided for use in a therapeutic method of repair and/or regeneration of skin. In another aspect of the present invention the use of Heparan Sulphate HS6 in the manufacture of a medicament for use in a therapeutic method of repair and/or regeneration of skin is provided. In another aspect of the present invention a therapeutic method of repair and/or regeneration of skin is provided, the method comprising administering Heparan Sulphate HS6 to a subject in need of treatment thereof.

In some embodiments the therapeutic method may involve treatment of a skin wound or scar, optionally selected from skin burns, ulcers, excisional wounds, cut, stab or puncture wounds. In some embodiments the therapeutic method may involve skin graft healing, skin reconstruction, or skin plastic surgery.

In another aspect of the present invention a method of healing a skin wound is provided, the method comprising contacting the skin wound with an effective amount of a pharmaceutical composition comprising HS6. In another aspect of the present invention heparan sulphate HS6 is provided for use in a method of healing a skin wound, the method comprising contacting the skin wound with an effective amount of a pharmaceutical composition comprising HS6. In another aspect of the present invention the use of heparan sulphate HS6 in the manufacture of a medicament for use in a method of healing a skin wound, the method comprising contacting the skin wound with an effective amount of a pharmaceutical composition comprising HS6 is provided.

In another aspect of the present invention a method of treating a subject having a skin wound is provided, the method comprising administration of a therapeutically effective amount of heparan sulphate HS6 to the subject leading to repair and/or regeneration of skin at the wound. In another aspect of the present invention heparan sulphate HS6 is provided for use in a method of treating a subject having a skin wound, the method comprising administration of a therapeutically effective amount of heparan sulphate HS6 to the subject leading to repair and/or regeneration of skin at the wound. In another aspect of the present invention the use of heparan sulphate HS6 in the manufacture of a medicament for use in a method of treating a subject having a skin wound, the method comprising administration of a therapeutically effective amount of heparan sulphate HS6 to the subject leading to repair and/or regeneration of skin at the wound, is provided.

In some embodiments the skin wound is a skin burn, ulcer, excisional wound, cut, stab or puncture wound In another aspect of the present invention a method of skin grafting, skin reconstruction, or skin plastic surgery is provided, the method comprising contacting the skin at or adjacent the region of grafting, reconstruction or plastic surgery with an effective amount of a pharmaceutical composition comprising HS6. In another aspect of the present invention heparan sulphate HS6 is provided for use in a method of skin grafting, skin reconstruction, or skin plastic surgery, the method comprising contacting the skin at or adjacent the region of grafting, reconstruction or plastic surgery with an effective amount of a pharmaceutical composition comprising HS6. In another aspect of the present invention the use of heparan sulphate HS6 in the manufacture of a medicament for use in a method of skin grafting, skin reconstruction, or skin plastic surgery is provided, the method comprising contacting the skin at or adjacent the region of grafting, reconstruction or plastic surgery with an effective amount of a pharmaceutical composition comprising HS6.

In another aspect of the present invention HS6 is provided for use in a method of scarless wound healing in skin. In another aspect of the present invention the use of HS6 in the manufacture of a medicament for use in a method of scarless wound healing in skin is provided. In another aspect of the present invention a method of scarless wound healing in skin is provided, the method comprising administering heparan sulphate HS6 to a subject in need of treatment thereof.

In another aspect of the present invention HS6 is provided for use in the treatment of wounds and/or injured tissues. In some embodiments, the tissue is a soft tissue, and in some embodiments the tissue is bone. In some embodiments the tissue is connective tissue, such as skin, tendon, ligament, fascia, fibrous tissues, fat or synovial membrane. In some embodiments the tissue is muscle, nerve or blood vessel tissue. In particular embodiments, the tissue is skin, tendon, ligament or bone. In some embodiments the skin wound is a skin burn, ulcer, excisional wound, cut, stab or puncture wound.

In another aspect of the present invention HS6 is provided for use to prevent or inhibit scarring, and/or to promote or facilitate healing or repair. In some embodiments the use is to prevent scarring and/or to promote or facilitate healing or repair of wounds or damaged tissue. In some embodiments, the damaged tissue or wound is a result of surgical intervention (e.g. a surgical wound), in particular incision. Wound healing may be in vivo repair and/or regeneration of tissue, e.g. skin, dermal or epithelial tissue.

In embodiments of the present invention HS6 is provided for use to promote skin graft healing, in skin reconstruction, or in skin plastic surgery.

In this and other aspects of the present invention, administration of HS6 may be at the point of care or later. For example, HS6 may be administered at the time of surgery, or later.

In another aspect of the present invention HS6 is provided for use as a stabilising agent. In some embodiments, HS6 is used as an agent for stabilising a growth factor. In some embodiments stabilising comprises promoting the activity of the growth factor. In some embodiments stabilising comprises prolonging the half-life or inhibiting degradation of the growth factor. The growth factor is preferably a protein growth factor, more preferably PDGF-B or PDGF-BB or a heterodimer comprising PDGF-B.

Accordingly, in one aspect of the present invention a method of stabilising PDGF-B, PDGF-BB or a heterodimer comprising PDGF-B, optionally in isolated and/or recombinant form, is provided the method comprising contacting PDGF-B, PDGF-BB or a heterodimer comprising PDGF-B with HS6, preferably a predetermined quantity of HS6, e.g. in the range 1 nM to 100 mM, or 1 µM to 100 mM, or 1 µM to 10 mM, or 1 µM to 1 mM. The method may comprise mixing the growth factor and HS6.

In another aspect of the present invention a method of increasing the stability of a growth factor is also provided, the method comprising contacting a growth factor with isolated HS6. In some embodiments the growth factor is PDGF-B or PDGF-BB or a heterodimer comprising PDGF-B.

In another aspect of the present invention HS6 is provided for use as a preserving agent and/or preservative. In some embodiments, HS6 is provided as a preserving agent or preservative for use to preserve biological material. In some embodiments HS6 is used as a preserving agent and/or preservative for biological material in storage.

In some embodiments, the biological material is cellular material or tissue. In some embodiments the cellular material or tissue is animal cellular material or animal tissue. In some embodiments the material has been obtained from an animal. In some embodiments the animal is a mammal, and in particular embodiments the mammal is a human.

In some embodiments, the cellular material or tissue is for use as source material for graft or transplant. In some embodiments the tissue is skin for use in a skin graft, skin reconstruction, or in skin plastic surgery.

In some embodiments HS6 is used as a preserving agent and/or preservative during the production of blood-derived products. In some embodiments the blood-derived products include platelets, platelet products, platelet lysates and platelet-rich plasma (PRP).

In accordance with the above, a method of preserving biological material is provided, preferably biological material comprising PDGF-B or PDGF-BB or a heterodimer comprising PDGF-B, the method comprising contacting the biological material with a predetermined quantity of HS6. In some embodiments the biological material may be selected from cellular material, tissue, blood-derived products, cells, or stem cells.

Accordingly, in one aspect of the present invention a method of preserving biological material is provided, the method comprising contacting the biological material with HS6, preferably a predetermined quantity of HS6, e.g. in the range 1 nM to 100 mM, or 1 µM to 100 mM, or 1 µM to 10 mM, or 1 µM to 1 mM.

In one aspect of the present invention a preparation comprising biological material and a preservative is provided, wherein the preservative comprises HS6, preferably a predetermined quantity of HS6, e.g. in the range 1 nM to 100 mM, or 1 µM to 100 mM, or 1 µM to 10 mM, or 1 µM to 1 mM. The biological material may be cellular material, tissue, blood, a blood-derived product, cells, or stem cells. The preparation may be an in vitro or ex vivo preparation.

In another aspect of the present invention HS6 is provided for use during isolation and/or processing of stem cells. In some embodiments, HS6 is provided as a reagent for use during culture and/or expansion of stem cells. Accordingly, a method of isolating, processing, culturing or expanding stem cells may be provided, the method comprising contacting the stem cells with a predetermined quantity of HS6, e.g. in the range 1 nM to 100 mM, or 1 μM to 100 mM, or 1 μM to 10 mM, or 1 μM to 1 mM. The stem cells may optionally express PDGF-B or PDGF-BB or a heterodimer comprising PDGF-B.

In another aspect of the present invention HS6 is provided for use to promote angiogenesis. Accordingly, a method of promoting angiogenesis is provided, the method comprising contacting cells or tissue, in vitro or in vivo, with a predetermined quantity of HS6. The tissue may be vascular tissue. The cells may be stem cells, e.g. hematopoietic stem cells.

In another aspect of the present invention a method for treating a dermal or epidermal wound in a subject is provided, the method comprising administering to the subject a pharmaceutical composition comprising HS6. In another aspect of the present invention heparan sulphate HS6 is provided for use in a method for treating a dermal or epidermal wound in a subject. In another aspect of the present invention, the use of heparan sulphate HS6 in the manufacture of a medicament for use in a method for treating a dermal or epidermal wound in a subject is provided.

In some embodiments HS6, or medicaments or pharmaceutical compositions containing HS6 may be formulated for topical or transdermal administration. In some embodiments HS6, or medicaments or pharmaceutical compositions containing HS6 may be formulated as a gel, spray, paste, ointment, cream, lotion, salve, oil, aqueous solution, suspension, dispersion, patch, adhesive plaster, bandage, dressing, depot, or reservoir.

In some embodiments, the method/treatment may further comprise administration of a growth factor, preferably PDGF-B, or PDGF-BB, or a heterodimer comprising PDGF-B. In some embodiments the HS6, or medicament or pharmaceutical composition is formulated as a combined preparation together with a growth factor, preferably PDGF-B, or PDGF-BB, or a heterodimer comprising PDGF-B.

In a further aspect of the present invention a biocompatible implant or prosthesis comprising a biomaterial and HS6 is provided. In some embodiments the implant or prosthesis is coated with HS6. In some embodiments the implant or prosthesis is impregnated with HS6. The implant or prosthesis may be further coated or impregnated with PDGF-B, or PDGF-BB, or a heterodimer comprising PDGF-B.

In another aspect of the present invention a method of forming a biocompatible implant or prosthesis is provided, the method comprising the step of coating or impregnating a biomaterial with HS6. In some embodiments the method further comprises coating or impregnating the biomaterial with PDGF-B, or PDGF-BB, or a heterodimer comprising PDGF-B.

Preferably, the HS6, and optionally PDGF-B, or PDGF-BB, or a heterodimer comprising PDGF-B, are respectively provided in therapeutically effective amounts. In some embodiments the method of treatment further comprises the step of formulating therapeutically effective amounts of HS6, and optionally PDGF-B, or PDGF-BB, or a heterodimer comprising PDGF-B, as a pharmaceutical composition comprising the HS6, and optionally PDGF-B, or PDGF-BB, or a heterodimer comprising PDGF-B, and a pharmaceutically acceptable carrier, adjuvant or diluent, wherein the pharmaceutical composition is administered to the patient.

In another aspect of the present invention a method of treatment of a patient is provided, the method comprising surgically implanting a biocompatible implant or prosthesis, which implant or prosthesis comprises a biomaterial and HS6, into tissue of the patient at or surrounding a site at which wound healing is required.

In some embodiments the implant or prosthesis is coated with HS6. In some embodiments the implant or prosthesis is impregnated with HS6. In some embodiments the implant or prosthesis is further impregnated with PDGF-B, or PDGF-BB, or a heterodimer comprising PDGF-B.

In yet a further aspect of the present invention a kit of parts is provided, the kit comprising a predetermined amount of HS6 and a predetermined amount of PDGF-B, or PDGF-BB, or a heterodimer comprising PDGF-B. The kit may comprise a first container containing the predetermined amount of HS6 and a second container containing the predetermined amount of PDGF-B, or PDGF-BB, or a heterodimer comprising PDGF-B. The kit may be provided for use in a method of medical treatment. The method of medical treatment may comprise a method of wound healing in vivo, the repair and/or regeneration of tissue, as described herein. The repair and/or regeneration may be in a mammal or a human. The kit may be provided together with instructions for the administration of the HS6 and PDGF-B, or PDGF-BB, or a heterodimer comprising PDGF-B separately, sequentially or simultaneously in order to provide the medical treatment.

In a further aspect of the present invention products are provided, the products containing therapeutically effective amounts of:
(i) HS6; and
(ii) PDGF-B, or PDGF-BB, or a heterodimer comprising PDGF-B;

for simultaneous, separate or sequential use in a method of medical treatment. The method of medical treatment may comprise a method of wound healing in vivo or the repair and/or regeneration of tissue as described herein. The repair and/or regeneration may be in a mammal or a human. The products may optionally be formulated as a combined preparation for co-administration.

DESCRIPTION

The inventors have used a sequence-based affinity chromatography platform to exploit the heparin-binding domain of PDGF-B. This allowed the enrichment of a PDGF-B and/or PDGF-BB binding heparan sulphate (HS) fraction. HS6

The present invention relates to a species of heparan sulphate molecule called HS6. HS6 molecules are obtainable by methods of enriching mixtures of compounds containing one or more glycosaminoglycans (GAGs) that bind to a polypeptide corresponding to a heparin-binding domain of PDGF-B. In particular, HS6 molecules can be obtained by enriching for heparan sulphate that binds to a heparan binding domain of PDGF-B which domain comprises, or consists of, the amino acid sequence RAKTPQTRVTIRT-VRVRRPPKGKHRKFKHTHDK (SEQ ID NO:1). The enrichment process may be used to isolate HS6.

Purified HS6 contains the sugar-binding code for the activation of PDGF-BB, a growth factor of major clinical importance already in widespread use. It enables significant improvement of the safety profile of the PDGF-BB, which, although undoubtedly useful, is also pro-oncogenic. The HS6 sugar allows lower doses of PDGF to be used, but be more therapeutically powerful. Within topical wound sites, the sugar by itself has significant healing effects.

The present invention also relates to mixtures of compounds enriched with HS6, and methods of using such mixtures.

In addition to being obtainable by the methodology described here, HS6 can also be defined functionally and structurally.

Functionally, an HS6 is capable of binding a peptide having, or consisting of, the amino acid sequence RAKTPQTRVTIRTVRVRRPPKGKHRKFKHTHDK (SEQ ID NO:1). The peptide may contain one or more additional amino acids on one or both ends of the peptide, or in some instances may be attached to a short amino acid linker sequence (e.g. about 1 to 5 amino acids in length) and/or a tag such as biotin.

Preferably, HS6 binds the peptide with a $K_D$ of less than 100 µM, more preferably less than one of 50 µM, 40 µM, 30 µM, 20 µM, 10 µM, 1 µM, 100 nM, 50 nM, 10 nM, 1 nM, or 100 µM.

Preferably, HS6 also binds PDGF-B, or PDGF-BB, with a $K_D$ of less than 100 µM, more preferably less than one of 50 µM, 40 µM, 30 µM, 20 µM, 10 µM, 1 µM, 100 nM, 50 nM, 10 nM, 1 nM, or 100 µM.

Binding between HS6 and PDGF-B, or PDGF-BB, may be determined by the following assay method.

PDGF-B or PDGF-BB is dissolved in Blocking Solution (0.2% gelatin in SAB) at a concentration of 3 µg/ml and a dilution series from 0-3 µg/ml in Blocking Solution is established. Dispensing of 200 µl of each dilution of PDGF-B or PDGF-BB into triplicate wells of Heparin/GAG Binding Plates pre-coated with heparin; incubated for 2 hrs at 37° C., washed carefully three times with SAB and 200 µl of 250 ng/ml biotinylated anti-PDGF-B or anti-PDGF-BB added in Blocking Solution. Incubation for one hour at 37° C., wash carefully three times with SAB, 200 µl of 220 ng/ml ExtrAvidin-AP added in Blocking Solution, Incubation for 30 mins at 37° C., careful washing three times with SAB and tap to remove residual liquid, 200 µl of Development Reagent (SigmaFAST p-Nitrophenyl phosphate) added. Incubate at room temperature for 40 minutes with absorbance reading at 405 nm within one hour.

In this assay, binding may be determined by measuring absorbance and may be determined relative to controls such as PDGF-B or PDGF-BB protein in the absence of added heparan sulphate, or PDGF-B/PDGF-BB protein to which an heparan sulphate is added that does not bind PDGF-B/PDGF-BB protein.

The binding of HS6 is preferably specific, in contrast to non-specific binding and in the context that the HS6 can be selected from other heparan sulphates and/or GAGs by a method involving selection of heparan sulphates exhibiting a high affinity binding interaction with the peptide comprising RAKTPQTRVTIRTVRVRRPPKGKHRKFKHTHDK such as SEQ ID NO:1, or with PDGF-B or PDGF-BB protein.

HS6+ binds with high affinity to PDGF-BB. The flow through fraction HS6− does not bind much PDGF-BB, yet contains chains with affinity for BMP-2, FGF-2 but not VEGF165. HS6 according to the present invention may be characterised by reference to ability to increase or enhance association of PDGF-BB and PDGFRβ (e.g. binding between PDGF-BB and PDGFRβ). In some embodiments, association between PDGF-BB and PDGFRβ is increased/enhanced by HS6 in a dose-dependent manner.

Increased/enhanced association between PDGF-BB and PDGFRβ observed in the presence of HS6 may be a consequence of formation of more PDGF-BB:PDGFRβ complexes in the presence of HS6 as compared to the number of complexes formed in the absence of HS6, and/or increased stability of PDGF-BB:PDGFRβ complexes in the presence of HS6 as compared to stability of complexes in the absence of HS6. HS6 may facilitate binding of PDGF-BB and PDGFRβ, and/or may stabilise PDGF-BB:PDGFRβ complexes.

Ability of a given heparan sulfate to increase/enhance association between PDGF-BB and PDGFRβ can be assayed by any suitable means, for example by co-immunoprecipitation analysis, e.g. as described in Example 16 herein.

HS6 has also been shown to:
- increase the growth rates of human dermal fibroblasts in vitro, and/or
- trigger the scratch wound assay response of both keratinocytes and dermal fibroblasts in vitro, and/or
- enhance the proliferative and migratory effects of PDGF-BB on human derma fibroblasts
- enhance the speed of wound healing in a pig skin model (e.g. as described in Example 14).
- increase/enhance binding of PDGF-BB to PDGFRβ. (e.g. as described in Example 16).

The mean average disaccharide composition of HS6 following digestion with heparin lyases I, II and III to completion and then subjecting the resulting disaccharide fragments to HPLC (or optionally to capillary electrophoresis) analysis is shown below.

| Disaccharide | Normalised weight percentage |
|---|---|
| ΔUA,2S-GlcNS,6S | 12.9 |
| ΔUA,2S-GlcNS | 6.8 |
| ΔUA-GlcNS,6S | 11.7 |
| ΔUA-GlcNS | 24.5 |
| ΔUA,2S-GlcNAc | 0.5 |
| ΔUA-GlcNAc,6S | 12.1 |
| ΔUA-GlcNAc | 31.6 |

HS6 according to the present invention includes heparan sulphate that has a disaccharide composition within ±10% (more preferably ±one of 9%, 8%, 7%, 6%, 5%, 4%, 3%, 2%, 1% or 0.5%) of the normalised percentage values shown for each disaccharide above for the HS6 retained species (HS6+) as determined by digestion with heparin lyases I, II and III to completion and then subjecting the resulting disaccharide fragments to HPLC (or optionally to capillary electrophoresis) analysis.

The disaccharide composition of HS6 as determined by digestion with heparin lyases I, II and III to completion and then subjecting the resulting disaccharide fragments to HPLC (or optionally to capillary electrophoresis) analysis may have a disaccharide composition according to any one of the following:

| Disaccharide | Normalised weight percentage |
|---|---|
| ΔUA,2S-GlcNS,6S | 12.9 ± 3.0 |
| ΔUA,2S-GlcNS | 6.8 ± 2.0 |
| ΔUA-GlcNS,6S | 11.7 ± 3.0 |
| ΔUA-GlcNS | 24.5 ± 3.0 |
| ΔUA,2S-GlcNAc | 0.5 ± 0.5 |
| ΔUA-GlcNAc,6S | 12.1 ± 3.0 |
| ΔUA-GlcNAc | 31.6 ± 3.0 |
| ΔUA,2S-GlcNS,6S | 12.9 ± 2.0 |
| ΔUA,2S-GlcNS | 6.8 ± 2.0 |
| ΔUA-GlcNS,6S | 11.7 ± 2.0 |
| ΔUA-GlcNS | 24.5 ± 2.0 |
| ΔUA,2S-GlcNAc | 0.5 ± 0.2 |

-continued

| Disaccharide | Normalised weight percentage |
| --- | --- |
| ΔUA-GlcNAc,6S | 12.1 ± 2.0 |
| ΔUA-GlcNAc | 31.6 ± 2.0 |
| ΔUA,2S-GlcNS,6S | 12.9 ± 2.0 |
| ΔUA,2S-GlcNS | 6.8 ± 1.0 |
| ΔUA-GlcNS,6S | 11.7 ± 2.0 |
| ΔUA-GlcNS | 24.5 ± 2.0 |
| ΔUA,2S-GlcNAc | 0.5 ± 0.2 |
| ΔUA-GlcNAc,6S | 12.1 ± 2.0 |
| ΔUA-GlcNAc | 31.6 ± 2.0 |
| ΔUA,2S-GlcNS,6S | 12.9 ± 1.0 |
| ΔUA,2S-GlcNS | 6.8 ± 0.5 |
| ΔUA-GlcNS,6S | 11.7 ± 1.0 |
| ΔUA-GlcNS | 24.5 ± 2.0 |
| ΔUA,2S-GlcNAc | 0.5 ± 0.2 |
| ΔUA-GlcNAc,6S | 12.1 ± 1.0 |
| ΔUA-GlcNAc | 31.6 ± 2.0 |
| ΔUA,2S-GlcNS,6S | 12.9 ± 0.75 |
| ΔUA,2S-GlcNS | 6.8 ± 0.3 |
| ΔUA-GlcNS,6S | 11.7 ± 0.75 |
| ΔUA-GlcNS | 24.5 ± 2.0 |
| ΔUA,2S-GlcNAc | 0.5 ± 0.1 |
| ΔUA-GlcNAc,6S | 12.1 ± 0.75 |
| ΔUA-GlcNAc | 31.6 ± 2.0 |
| ΔUA,2S-GlcNS,6S | 12.9 ± 0.5 |
| ΔUA,2S-GlcNS | 6.8 ± 0.2 |
| ΔUA-GlcNS,6S | 11.7 ± 0.5 |
| ΔUA-GlcNS | 24.6 ± 1.5 |
| ΔUA,2S-GlcNAc | 0.5 ± 0.2 |
| ΔUA-GlcNAc,6S | 12.1 ± 0.5 |
| ΔUA-GlcNAc | 31.6 ± 0.8 |
| ΔUA,2S-GlcNS,6S | 12.8 ± 0.5 |
| ΔUA,2S-GlcNS | 6.8 ± 0.2 |
| ΔUA-GlcNS,6S | 11.6 ± 0.5 |
| ΔUA-GlcNS | 24.5 ± 0.5 |
| ΔUA,2S-GlcNAc | 0.5 ± 0.1 |
| ΔUA-GlcNAc,6S | 12.2 ± 0.4 |
| ΔUA-GlcNAc | 31.6 ± 0.5 |
| ΔUA,2S-GlcNS,6S | 13.0 ± 0.5 |
| ΔUA,2S-GlcNS | 6.7 ± 0.2 |
| ΔUA-GlcNS,6S | 11.6 ± 0.5 |
| ΔUA-GlcNS | 24.5 ± 0.5 |
| ΔUA,2S-GlcNAc | 0.5 ± 0.1 |
| ΔUA-GlcNAc,6S | 12.2 ± 0.4 |
| ΔUA-GlcNAc | 31.6 ± 0.5 |
| ΔUA,2S-GlcNS,6S | 13.0 ± 0.5 |
| ΔUA,2S-GlcNS | 6.8 ± 0.2 |
| ΔUA-GlcNS,6S | 11.8 ± 0.5 |
| ΔUA-GlcNS | 24.5 ± 0.5 |
| ΔUA,2S-GlcNAc | 0.5 ± 0.1 |
| ΔUA-GlcNAc,6S | 12.0 ± 0.4 |
| ΔUA-GlcNAc | 31.4 ± 0.5 |
| ΔUA,2S-GlcNS,6S | 12.8 ± 0.5 |
| ΔUA,2S-GlcNS | 6.8 ± 0.2 |
| ΔUA-GlcNS,6S | 11.6 ± 0.5 |
| ΔUA-GlcNS | 24.6 ± 0.5 |
| ΔUA,2S-GlcNAc | 0.5 ± 0.1 |
| ΔUA-GlcNAc,6S | 12.0 ± 0.4 |
| ΔUA-GlcNAc | 31.6 ± 0.5 |

Following digestion with heparin lyases I, II and III to completion the disaccharide ΔUA,2S GlcNAc,6S may be absent from HS6, or only trace amounts may be detectable by HPLC/capillary electrophoresis analysis.

In preferred embodiments the total weight percentage of the disaccharides listed is 100% (optionally ±3.0% or less, or ±2.0% or less, ±1.0% or less, ±0.5% or less, ±0.1% or less). For any given set of disaccharide percentages the total may be slightly greater than, or less than, 100% owing to rounding of each calculated percentage, in particular where mean average values are used.

HS6 may also be characterised by being N-sulfated.

Disaccharide compositional analysis of HS-6 after heparin lyase treatment reveals it to have slightly less ΔUA-GlcNAc and ΔUA-GlcNS than Celsus HS 10697 and be slightly enriched in ΔUA-GlcNS,6S and ΔUA,2S-GlcNS,6S. Most importantly, the non-retained HS-6 contains more ΔUA-GlcNAc and ΔUA-GlcNS than HS-6 and Celsus HS 10697 and less ΔUA-GlcNS,6S and ΔUA,2S-GlcNS,6S.

Digestion of HS6 with heparin lyases I, II and III and/or HPLC/capillary electrophoresis analysis of disaccharides is preferably performed in accordance with Example 6.

By way of example, digestion of HS preparations with heparin lyase enzymes may be conducted as follows: HS preparations (1 mg) are each dissolved in 500 μL of sodium acetate buffer (100 mM containing 10 mM calcium acetate, pH 7.0) and 2.5 mU each of the three enzymes is added; the samples are incubated at 37° C. overnight (24 h) with gentle inversion (9 rpm) of the sample tubes; a further 2.5 mU each of the three enzymes is added to the samples which are incubated at 37° C. for a further 48 h with gentle inversion (9 rpm) of the sample tubes; digests are halted by heating (100° C., 5 min) and are then lyophilized; digests are resuspended in 500 μL water and an aliquot (50 μL) is taken for analysis.

By way of example, capillary electrophoresis (CE) of disaccharides from digestion of HS preparations may be conducted as follows: capillary electrophoresis operating buffer is made by adding an aqueous solution of 20 mM $H_3PO_4$ to a solution of 20 mM $Na_2HPO_4 \cdot 12H_2O$ to give pH 3.5; column wash is 100 mM NaOH (diluted from 50% w/w NaOH); operating buffer and column wash are both filtered using a filter unit fitted with 0.2 μm cellulose acetate membrane filters; stock solutions of disaccharide Is (e.g. 12) are prepared by dissolving the disaccharides in water (1 mg/mL); calibration curves for the standards are determined by preparing a mix containing all standards containing 10 μg/100 μL of each disaccharide and a dilution series containing 10, 5, 2.5, 1.25, 0.625, 0.3125 μg/100 μL is prepared; including 2.5 μg of internal standard (ΔUA,2S-GlcNCOEt, 6S). The digests of HS are diluted (50 μL/mL) with water and the same internal standard is added (2.5 μg) to each sample. The solutions are freeze-dried and re-suspended in water (1 mL). The samples are filtered using PTFE hydrophilic disposable syringe filter units.

Analyses are performed using a capillary electrophoresis instrument on an uncoated fused silica capillary tube at 25° C. using 20 mM operating buffer with a capillary voltage of 30 kV. The samples are introduced to the capillary tube using hydrodynamic injection at the cathodic (reverse polarity) end. Before each run, the capillary is flushed with 100 mM NaOH (2 min), with water (2 min) and pre-conditioned with operating buffer (5 min). A buffer replenishment system replaces the buffer in the inlet and outlet tubes to ensure consistent volumes, pH and ionic strength are maintained. Water only blanks are run at both the beginning, middle and end of the sample sequence. Absorbance is monitored at 232 nm. All data is stored in a database and is subsequently retrieved and re-processed. Duplicate or triplicate digests/analyses may be performed and the normalized percentage of the disaccharides in the HS digest is calculated as the mean average of the results for the analyses.

In some embodiments an HS6 chain comprises at least 4 saccharide units (degree of polymerisation, dp). In some embodiments the dp number may be one of at least 2 disaccharides (i.e. dp4), at least 3 disaccharides, at least 4 disaccharides, at least 5 disaccharides, at least 6 disaccharides, at least 7 disaccharides, at least 8 disaccharides, at least 9 disaccharides, at least 10 disaccharides, at least 11 disaccharides, at least 12 disaccharides, at least 13 disaccharides, at least 14 disaccharides, at least 15 disaccharides, at least 16 disaccharides, at least 17 disaccharides, at least 18 disaccharides, at least 19 disaccharides, at least 20 disaccharides, at least 21 disaccharides, at least 22 disaccharides, at least 23 disaccharides, at least 24 disaccharides, at least 25 disaccharides, at least 26 disaccharides, at least 27 disaccharides, at least 28 disaccharides, at least 29 disaccharides, or at least 30 disaccharides.

To identify HS6 the inventors used a method that involves enriching for glycosaminoglycan molecules that exhibit binding to particular polypeptides having a heparin-binding domain.

Isolated GAG mixtures and/or molecules can then be identified and tested for their ability to modulate proliferation or migration of dermal fibroblasts in vitro. This methodology is described in PCT/GB2009/000469 (WO2010/030244), incorporated herein by reference. The inventors applied this methodology to PDGF-B/PDGF-BB in order to isolate and characterise GAGs having high binding to PDGF-B/PDGF-BB.

Accordingly, to identify HS6 the inventors provided a method of isolating glycosaminoglycans capable of binding to proteins having heparin/heparan-binding domains, the method comprising:
 (i) providing a solid support having polypeptide molecules adhered to the support, wherein the polypeptide comprises a heparin-binding domain;
 (ii) contacting the polypeptide molecules with a mixture comprising glycosaminoglycans such that polypeptide-glycosaminoglycan complexes are allowed to form;
 (iii) partitioning polypeptide-glycosaminoglycan complexes from the remainder of the mixture;
 (iv) dissociating glycosaminoglycans from the polypeptide-glycosaminoglycan complexes;
 (v) collecting the dissociated glycosaminoglycans.

The inventors used these methods to identify a GAG capable of binding to PDGF-B/PDGF-BB (which they called HS6), wherein the polypeptide used in the inventors' methodology comprised the heparin-binding domain of RAKTPQTRVTIRTVRVRRPPKGKHRKFKHTHDK (SEQ ID NO:1).

In the inventors' methodology, the mixture comprising GAGs may contain synthetic glycosaminoglycans. However, GAGs obtained from cells or tissues are preferred. The mixture comprising GAGs is preferably a heparan sulphate preparation/fraction, such as $HS^{PM}$. In preferred embodiments the GAG is heparan sulphate.

The heparan sulphate or GAG component may be extracted from a tissue or cell sample or extract by a series of routine separation steps (e.g. anion exchange chromatography), well known to those of skill in the art.

GAG mixtures may contain a mixture of different types of glycosaminoglycan, which may include dextran sulphates, chondroitin sulphates and heparan sulphates. Preferably, the GAG mixture contacted with the solid support is enriched for heparan sulphate. A heparan sulphate-enriched GAG fraction may be obtained by performing column chromatography on the GAG mixture, e.g. weak, medium or strong anion exchange chromatography, as well as strong high pressure liquid chromatography (SAX-HPLC), with selection of the appropriate fraction.

The collected GAGs may be subjected to further analysis in order to identify the GAG, e.g. determine GAG composition or sequence, or determine structural characteristics of the GAG. GAG structure is typically highly complex, and, taking account of currently available analytical techniques, exact determinations of GAG sequence structure are not possible in most cases.

However, the collected GAG molecules may be subjected to partial or complete saccharide digestion (e.g. chemically by nitrous acid or enzymatically with lyases such as heparinase III) to yield saccharide fragments that are both characteristic and diagnostic of the GAG. In particular, digestion to yield disaccharides (or tetrasaccharides) may be used to measure the percentage of each disaccharide obtained which will provide a characteristic disaccharide "fingerprint" of the GAG.

The pattern of sulphation of the GAG can also be determined and used to determine GAG structure. For example, for heparan sulphate the pattern of sulphation at amino sugars and at the C2, C3 and C6 positions may be used to characterise the heparan sulphate.

Disaccharide analysis, tetrasaccharide analysis and analysis of sulphation can be used in conjunction with other analytical techniques such as HPLC, mass spectrometry and NMR which can each provide unique spectra for the GAG. In combination, these techniques may provide a definitive structural characterisation of the GAG.

A high affinity binding interaction between the GAG and heparin-binding domain indicates that the GAG will contain a specific saccharide sequence that contributes to the high affinity binding interaction. A further step may comprise determination of the complete or partial saccharide sequence of the GAG, or the key portion of the GAG, involved in the binding interaction.

GAG-polypeptide (e.g. HS-polypeptide) complexes may be subjected to treatment with an agent that lyses glycosaminoglycan chains, e.g. a lyase. Lyase treatment may cleave portions of the bound GAG that are not taking part in the binding interaction with the polypeptide. Portions of the GAG that are taking part in the binding interaction with the polypeptide may be protected from lyase action. After removal of the lyase, e.g. following a washing step, the GAG molecule that remains bound to the polypeptide represents the specific binding partner ("GAG ligand") of the polypeptide. Owing to the lower complexity of shorter GAG molecules, following dissociation and collection of the GAG ligand, a higher degree of structural characterisation of the GAG ligand can be expected. For example, the combination of any of the saccharide sequence (i.e. the primary (linear) sequence of monosaccharides contained in the GAG ligand), sulphation pattern, disaccharide and/or tetrasaccharide digestion analysis, NMR spectra, mass spectrometry spectra and HPLC spectra may provide a high level of structural characterisation of the GAG ligand.

As used herein, the terms 'enriching', 'enrichment', 'enriched', etc. describes a process (or state) whereby the relative composition of a mixture is (or has been) altered in such a way that the fraction of that mixture given by one or more of those entities is increased, while the fraction of that mixture given by one or more different entities is decreased.

GAGs isolated by enrichment may be pure, i.e. contain substantially only one type of GAG, or may continue to be a mixture of different types of GAG, the mixture having a higher proportion of particular GAGs that bind to the heparin-binding domain relative to the starting mixture.

HS6 preferably exhibits a functional effect when contacted with cells or tissue in which a protein containing the heparin-binding domain is expressed or contained. The functional effect may be a modulating or potentiating effect.

The functional effect may be to promote (stimulate) or inhibit the proliferation of the cells of a certain type or the differentiation of one cell type into another, or the expression of one or more protein markers. For example, the GAGs may promote cell proliferation, i.e. an increase in cell number, or promote differentiation of cells.

As used herein, the term 'modulating effect' is understood to mean the effect that a first entity has on a second entity wherein the second entity's normal function in another process or processes is modified by the presence of the first entity. The modulating effect may be either agonistic or antagonistic.

The modulating effect may be a potentiating effect. The term 'potentiating effect' is understood to mean the effect of increasing potency. In a preferred embodiment of the present invention, the term 'potentiating effect' refers to the effect that a first entity has on a second entity, which effect increases the potency of that second entity in another process or processes. In a further preferred embodiment of the present invention, the potentiating effect is understood to mean the effect of isolated GAGs on a heparin-binding factor, wherein the said effect increases the potency of said heparin-binding factor.

As used herein, the process of 'contacting' involves the bringing into close physical proximity of two or more discrete entities. The process of 'contacting' involves the bringing into close proximity of two or more discrete entities for a time, and under conditions, sufficient to allow a portion of those two or more discrete entities to interact on a molecular level. Preferably, as used herein, the process of 'contacting' involves the bringing into close proximity of the mixture of compounds possessing one or more GAGs and the polypeptide corresponding to the heparin-binding domain of a heparin-binding factor. Examples of 'contacting' processes include mixing, dissolving, swelling, washing. In preferred embodiments 'contact' of the GAG mixture and polypeptide is sufficient for complexes, which may be covalent but are preferably non-covalent, to form between GAGs and polypeptides that exhibit high affinity for each other.

The polypeptide may comprise the full length or near full length primary amino acid sequence of a selected protein having a heparin-binding domain. Due to folding that may occur in longer polypeptides leading to possible masking of the heparin-binding domain from the GAG mixture, it is preferred for the polypeptide to be short. Preferably, the polypeptide will have an amino acid sequence that includes, or consists of, the heparin-binding domain and optionally including one or more amino acids at one or each of the N- and C-terminals of the peptides. These additional amino acids may enable the addition of linker or attachment molecules (e.g. a tag such as biotin) to the polypeptide that are required to attach the polypeptide to the solid support.

In preferred embodiments of the inventors' methodology, in addition to the number of amino acids in the heparin-binding domain the polypeptide contains no more than 1-20, more preferably 1-10, still more preferably 1-5 additional amino acids, e.g. any of 1, 2, 3, 4, 5, 6, 7, 8, 9, 10, 11, 12, 13, 14, 15, 16, 17, 18, 19 or 20 amino acids at one or both of the C- and/or N-terminals of the polypeptide. In some embodiments the amino acid sequence of the heparin-binding domain accounts for at least 80% of the amino acids of the polypeptide, more preferably one of at least 90%, 91%, 92%, 93%, 94%, 95%, 96%, 97%, 98%, 99% or 100%. In order to adhere polypeptides to the surface of a solid support the polypeptides are preferably modified to include a molecular tag, and the surface of the solid support is modified to incorporate a corresponding molecular probe having high affinity for the molecular tag, i.e. the molecular tag and probe form a binding pair. The tag and/or probe may be chosen from any one of: an antibody, a cell receptor, a ligand, biotin, any fragment or derivative of these structures, any combination of the foregoing, or any other structure with which a probe can be designed or configured to bind or otherwise associate with specificity. A preferred binding pair suitable for use as tag and probe is biotin and avidin.

The polypeptide is derived from the protein of interest, which in the present case is PDGF-B/PDGF-BB. By "derived from" is meant that the polypeptide is chosen, selected or prepared because it contains the amino acid sequence of a heparin-binding domain that is present in the protein of interest. The amino acid sequence of the heparin-binding domain may be modified from that appearing in the protein of interest, e.g. to investigate the effect of changes in the heparin-binding domain sequence on GAG binding.

In this specification the protein is PDGF-B (monomer) or PDGF-BB (homodimer) or a heterodimer comprising PDGF-B such as PDGF-AB. Reference herein to PDGF-BB includes reference to PDGF-B unless stated otherwise. The amino acid sequences of the preferred heparin-binding domain is RAKTPQTRVTIRTVRVRRPPKGKHRK-FKHTHDK (SEQ ID NO:1) (e.g. Cook et al. 1992, Biochem J. 1992 Jan. 1; 281 (Pt 1):57-65). The amino acid sequence of human PDGF-B can be found in GenBank under accession no. NP_002599.1 GI:4505681 in which SEQ ID NO:1 starts at position 200.

It is understood by those skilled in the art that small variations in the amino acid sequence of a particular polypeptide may allow the inherent functionality of that portion to be maintained. It is also understood that the substitution of certain amino acid residues within a peptide with other amino acid residues that are isosteric and/or isoelectronic may either maintain or improve certain properties of the unsubstituted peptide. These variations are also encompassed within the scope of the present invention. For example, the amino acid alanine may sometimes be substituted for the amino acid glycine (and vice versa) whilst maintaining one or more of the properties of the peptide. The term 'isosteric' refers to a spatial similarity between two entities. Two examples of moieties that are isosteric at moderately elevated temperatures are the iso-propyl and tert-butyl groups. The term 'isoelectronic' refers to an electronic similarity between two entities, an example being the case where two entities possess a functionality of the same, or similar, pKa.

The polypeptide corresponding to the heparin-binding domain may be synthetic or recombinant.

The solid support may be any substrate having a surface to which molecules may be attached, directly or indirectly, through either covalent or non-covalent bonds. The solid support may include any substrate material that is capable of providing physical support for the probes that are attached to the surface. It may be a matrix support. The material is generally capable of enduring conditions related to the attachment of the probes to the surface and any subsequent treatment, handling, or processing encountered during the performance of an assay. The materials may be naturally occurring, synthetic, or a modification of a naturally occurring material. The solid support may be a plastics material (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), etc., either used by themselves or in conjunction with other materials. Additional rigid materials may be considered, such as glass, which includes silica and further includes, for example, glass that is available as Bioglass.

Other materials that may be employed include porous materials, such as, for example, controlled pore glass beads. Any other materials known in the art that are capable of having one or more functional groups, such as any of an amino, carboxyl, thiol, or hydroxyl functional group, for example, incorporated on its surface, are also contemplated.

Preferred solid supports include columns having a polypeptide immobilized on a surface of the column. The surface may be a wall of the column, and/or may be provided by beads packed into the central space of the column.

The polypeptide may be immobilised on the solid support. Examples of methods of immobilisation include: adsorption, covalent binding, entrapment and membrane confinement. In a preferred embodiment of the present invention the interaction between the polypeptide and the matrix is substantially permanent. In a further preferred embodiment of the present invention, the interaction between the peptide and the matrix is suitably inert to ion-exchange chromatography. In a preferred arrangement, the polypeptide is attached to the surface of the solid support. It is understood that a person skilled in the art would have a large array of options to choose from to chemically and/or physically attach two entities to each other. These options are all encompassed within the scope of the present invention. In a preferred arrangement, the polypeptide is adsorbed to a solid support through the interaction of biotin with streptavidin. In a representative example of this arrangement, a molecule of biotin is bonded covalently to the polypeptide, whereupon the biotin-polypeptide conjugate binds to streptavidin, which in turn has been covalently bonded to a solid support. In another arrangement, a spacer or linker moiety may be used to connect the molecule of biotin with the polypeptide, and/or the streptavidin with the matrix.

By contacting the GAG mixture with the solid support GAG-polypeptide complexes are allowed to form. These are partitioned from the remainder of the mixture by removing the remainder of the mixture from the solid support, e.g. by washing the solid support to elute non-bound materials. Where a column is used as the solid support non-binding components of the GAG mixture can be eluted from the column leaving the GAG-polypeptide complexes bound to the column.

It is understood that certain oligosaccharides may interact in a non-specific manner with the polypeptide. In certain embodiments, oligosaccharide which interacts with the polypeptide in a non-specific manner may be included in, or excluded from the mixture of compounds enriched with one or more GAGs that modulate the effect of a heparin-binding factor. An example of a non-specific interaction is the temporary confinement within a pocket of a suitably sized and/or shaped molecule. Further it is understood that these oligosaccharides may elute more slowly than those oligosaccharides that display no interaction with the peptide at all. Furthermore it is understood that the compounds that bind non-specifically may not require the input of the same external stimulus to make them elute as for those compounds that bind in a specific manner (for example through an ionic interaction). The inventors' methodology is capable of separating a mixture of oligosaccharides into those components of that mixture that: bind in a specific manner to the polypeptide; those that bind in a non-specific manner to the polypeptide; and those that do not bind to the polypeptide. These designations are defined operationally for each GAG-peptide pair.

By varying the conditions (e.g. salt concentration) present at the surface of the solid support where binding of the GAG and polypeptide occurs those GAGs having the highest affinity and/or specificity for the heparin-binding domain can be selected.

GAGs may accordingly be obtained that have a high binding affinity for a protein of interest and/or the heparin-binding domain of the protein of interest. The binding affinity ($K_d$) may be chosen from one of: less than 10 µM, less than 1 µM, less than 100 nM, less than 10 nM, less than 1 nM, less than 100 µM.

HS6 and PDGF-BB

HS6 has the property of stabilising PDGF-B, preventing its degradation and thereby prolonging its action. Accordingly, in aspects of the present invention HS6 finds use to promote or prolong activity of PDGF-B, PDGF-BB or a heterodimer comprising PDGF-B.

HS6 finds use in any application wherein stabilisation of PDGF-B (or PDGF-BB or a heterodimer comprising PDGF-B) and/or prevention of degradation of PDGF-B (or PDGF-BB or a heterodimer comprising PDGF-B) and/or prolonging of PDGF-B (or PDGF-BB or a heterodimer comprising PDGF-B) is desirable. For example, HS6 finds use to stabilise PDGF-BB in platelet products.

In one aspect of the present invention a composition comprising a growth factor and isolated HS6 is provided. The composition may optionally be sterile. The growth factor may be a protein growth factor, and is preferably one of PDGF-B, PDGF-BB or a heterodimer comprising PDGF-B. The composition may comprise isolated growth factor and isolated HS6. In some embodiments the composition may be a culture media. In other embodiments the composition may be a pharmaceutical composition or medicament containing the growth factor.

The composition may be a preparation comprising PDGF-B (or PDGF-BB or a heterodimer comprising PDGF-B) and isolated HS6 in a container. A suitable container may be a bottle, vial, tube or syringe.

A method of increasing the stability of a growth factor is also provided, the method comprising contacting a growth factor with isolated HS6.

The stability of the growth factor may be measured in terms of its half-life, i.e. the amount of time taken for half of the growth factor in a given composition to be degraded and/or lose its activity. The growth factor is preferably a protein growth factor, more preferably one of PDGF-B, PDGF-BB or a heterodimer comprising PDGF-B. HS6 acts to maintain and prolong the half-life of the growth factor. The method may involve contacting isolated HS6 with the growth factor (e.g. PDGF-BB) in vitro, e.g. as part of preparation of a growth factor (e.g. PDGF-BB) composition, its storage or transport. Alternatively, the method may involve contacting isolated HS6 with the growth factor (e.g. PDGF-BB) in vivo, e.g. by administering isolated HS6 to tissue in which the growth factor (e.g. PDGF-BB) [naturally occurring in the tissue or exogenously added to the tissue] is present. The method may also comprise the step of adding exogenous growth factor (e.g. PDGF-BB) to the tissue.

The stability of the growth factor in a given composition or tissue that contains isolated HS6 (or to which isolated HS6 has been added) may be compared against a comparable composition not containing HS6 (or to which isolated HS6 has not been added).

In the composition and method described above the HS6 may be purified, as described herein. The growth factor may be isolated and/or purified, non-isolated or partially isolated, e.g. part of an extracellular matrix material, or present in a composition of cells. Isolated or purified growth factor may be recombinant growth factor. Recombinant PDGF-BB is commercially available from a number of manufacturers such as Peprotech; Merck Millipore, MA; Life Technologies Corporation and Gibco.

Use of HS6 in the Repair and/or Regeneration of Skin We have developed a purified HS preparation, HS6 described herein that is more specifically targeted at PDGF-B/PDGF-BB. We have shown that HS6 possesses an increased affinity for PDGF-B/PDGF-BB, increases the growth rates of human dermal fibroblasts, and triggers the scratch wound assay response of both keratinocytes and dermal fibroblasts. HS6 will be trialled as an adjuvant that induces the repair of skin after trauma, burns, ulceration or disease. HS6 will be trialled as an adjuvant that both stabilizes and reduces the amounts of growth factor required to treat chronic wounds of the skin, including full thickness, excisional wounds. HS6 thus provides a useful therapeutic tool for the treatment of non-healing skin wounds such as diabetic ulcers which are a major and growing drain on the health system, and an urgent and major unmet clinical need.

Accordingly, aspects of the invention concern the therapeutic use of HS6 in the repair and/or regeneration of skin. Repair or regeneration of skin may be required in response to injury or formation of a wound in the skin. The therapeutic use may involve treatment of skin wounds or skin scars of any kind. Wounds may be acute or chronic. Wounds may be slow-healing or non-healing.

The injury may be any injury that disrupts the skin barrier. In some embodiments the injury may be a physical or mechanical injury. It may be an excisional wound or excisional skin trauma. In some embodiments the wound may be a cut, stab or puncture wound. In some embodiments it may be a surgical cut. In other embodiments the injury may be a result of a burn, which may be a heat or chemical burn. Burns which may be treated may be first degree, second degree or third degree. The action of HS6 may be to facilitate or accelerate the wound healing process in response to such injuries.

In some embodiments HS6 may be used to facilitate or accelerate wound healing in skin or skin graft healing, e.g. following skin grafting, skin reconstruction or skin plastic surgery. In some embodiments HS may be used to reduce or minimise scar formation during skin wound healing. In some embodiments HS6 is used to achieve scarless wound healing in skin.

Therapeutic applications of HS6 in skin wound healing include wound healing after plastic surgery, colorectal anastomotic surgery, closing up stitches, treatment of burns, vascular/arterial/pressure ulcer treatment, skin incisional/trauma wound repair, the encouraging of blood vessels back into the epidermal compartment and stimulation of epidermal stem cell function.

In some embodiments HS6 may be used to treat a skin ulcer, for example a diabetic skin ulcer. Skin ulcers may be non-healing ulcers, e.g. non-healing lower extremity ulcers.

In some optional embodiments, HS6 is not used for the treatment of graft versus host disease of the skin.

Skin Grafting, Reconstruction and Plastic Surgery

Skin grafting involves the transplantation of skin and is often used to treat traumatic wounds in which large areas of skin are damaged, e.g. in burns, skin cancer or following infections such as necrotizing fasciitis The process typically involves surgical removal of the damaged skin followed by grafting of transplanted skin. Skin grafts may be obtained by removing either a thin layer of skin or a full thickness section of skin from a healthy part of the body. Grafts are typically obtained from the subject requiring treatment (autologous) or from another individual of the same species (allogeneic)

Skin grafting, reconstruction and plastic surgery techniques are known to those of skill in the art, for example as described in Snyder et al (Applying split-thickness skin grafts: a step-by-step clinical guide and nursing implications. Ostomy Wound Manage. 2001 November; 47(11):20-6); Jeffrey E. Janis (Essentials of Plastic Surgery CRC Press, 22 Jul. 2007) Ziegler, Dietz and Schmidt (Skin Grafts. *Surgery in Wounds*. 2004, pp 179-186); Weerda, Hilko (2001). Reconstructive Facial Plastic Surgery: A Problem-Solving Manual. Barret-Nerin, Juan; Herndon, David N. (2004). Principles and Practice of Burn Surgery. New York: Marcel Dekker.

In aspects and embodiments of the present invention HS6 is provided for use in methods of skin grafting, reconstruction and plastic surgery to assist the skin healing process and/or acceptance of the graft. HS6 may be applied or administered to the skin at or adjacent the site of grafting, reconstruction or surgery. Such application may form part of the surgical method or may be separate to the surgical method, e.g. being applied post-surgery to an area of skin that has undergone grafting, reconstruction or plastic surgery.

Use of HS6 in the Repair and/or Regeneration of Bone

In some aspects the present invention is concerned with the therapeutic use (human and/or veterinary) of HS6 to repair and/or regenerate bone. This may involve treatment of wounds in bone, typically bone fracture.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopaedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures.

In most subjects bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralisation) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment using HS6 include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella).

Bones in which fractures occur and which may benefit from treatment using HS6 include skeletal bone (i.e. any bone of the skeleton), bones of the cranio-facial region, bones of the axial skeleton (e.g. vertebrae, ribs), appendicular bone (e.g. of the limbs), bone of the pelvic skeleton (e.g. pelvis).

Bones in which fractures occur and which may benefit from treatment using HS6 also include those of the head (skull) and neck, including those of the face such as the jaw, nose and cheek. HS6 may be used to assist in repair or regeneration of bone during dental or facial or cranial surgery, which may include reconstruction of bones (as distinct from teeth) of the face and/or mouth, e.g. including the jawbone.

Bone fracture also includes pathological porosity, such as that exhibited by subjects with osteoporosis.

Although not limiting to the present invention, the primary actions of HS6 may be on cells within, adjacent to, or caused to migrate into the wound site and may be on the mesenchymal stem cells, bone stem cells, the preosteoblasts or the osteoblasts, or on any of the ancillary or vasculogenic cells found or caused to migrate into or within the wound bed.

HS6 and pharmaceutical compositions and medicaments comprising HS6 are provided for use in a method of treatment of bone fracture in a mammalian subject.

Treatment may comprise wound healing in bone. The treatment may involve repair, regeneration and growth of bone. HS6 facilitates fracture repair by facilitating new bone growth. HS6 acts to improve the speed of fracture repair enabling bone healing to occur faster leading to improved recovery time from injury. Treatment may lead to improved bone strength.

Treatment may also include treatment of osteoporosis or osteoarthritis.

Administration of HS6 is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

Medicaments and pharmaceutical compositions according to the present invention may be formulated for administration by a number of routes. Most preferably HS6 is formulated in fluid or liquid form for injection.

In some embodiments the HS6 is formulated as a controlled release formulation, e.g. in a drug capsule for implantation at the wound site. The HS6 may be attached to, impregnated on or soaked into a carrier material (e.g. a biomaterial) such as nanofibres or biodegradable paper or textile.

Pharmaceutical compositions, medicaments, implants and prostheses comprising HS6 may also comprise PDGF-B, PDGF-BB, or a heterodimer comprising PDGF-B. Owing to the ability of HS6 to bind PDGF-B, PDGF-BB, or a heterodimer comprising PDGF-B, the HS6 may act as a carrier of the protein assisting in delivery of the protein to the wound site.

Administration is preferably in a "therapeutically effective amount", this being sufficient to improve healing of the bone fracture compared to a corresponding untreated fracture. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of HS6 doses may be administered in accordance with the guidance of the prescribing medical practitioner. Purely by way of example, HS6 may be delivered in dosages of at least 1 ng/ml, more preferably at least 5 ng/ml and optionally 10 ng/ml or more. Individual HS6 dosages may be of the order less than 1 mg and greater than 1 µg, e.g. one of about 5 µg, about 10 µg, about 25 µg, about 30 µg, about 50 µg, about 100 µg, about 0.5 mg, or about 1 mg. Examples of the techniques and protocols mentioned above can be found in Remington's Pharmaceutical Sciences, 20th Edition, 2000, pub. Lippincott, Williams & Wilkins.

HS6 may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required HS6 may be administered directly to (e.g. applied to) the fracture during the surgical procedure.

Use of HS6 in the Repair and/or Regeneration of Soft Tissue

In some aspects the present invention is concerned with the therapeutic use (human and/or veterinary) of HS6 to repair and/or regenerate soft tissue. This may involve treatment of wounds or diseases in soft tissue.

Soft tissues include connective tissue, muscle, tendon, ligament, fascia, joints, fibrous tissues, fat and synovial membrane.

Soft tissues wounds may be caused by injury or damage, which may be of any kind, e.g. physical, mechanical, heat or chemical injury or damage. In some embodiments the wound may be a cut, stab or puncture wound. In some embodiments it may be a surgical cut. Physical and mechanical injuries may be sports injuries, e.g. ligament and tendon ruptures, joint capsular injuries and tendonitis. The action of HS6 may be to facilitate or accelerate the wound healing process in response to such injuries.

Soft tissue therapy concerns the treatment of soft tissue injury, pain and dysfunction. Soft tissues disorders and diseases include gum disease (gingivitis, periodontitis), ulcers, and chronic wounds.

The role of PDGF and activated platelets in treating soft tissue wounds and disorders is reviewed in Rozman et al (Use of platelet grwoth factors in treating wounds and soft-tissue injuries. Acta Dermatoven APA Vol 16, 2007, No. 4, p 156-165).

Formulations

While it is possible for the active compound, HS6, to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, adjuvants, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Suitable carriers, adjuvants, excipients, etc. can be found in standard pharmaceutical texts, for example, Remington's Pharmaceutical Sciences, 18th edition, Mack Publishing Company, Easton, Pa., 1990; and Handbook of Pharmaceutical Excipients, 2nd edition, 1994.

In some embodiments HS6 may be formulated as a powder, e.g. lyophilised powder, which may be re-hydrated by mixing with a fluid, e.g. water or saline, preferably sterile, to form a liquid, fluid or gel formulation.

In some embodiments gel, hydrogel, putty or paste formulations are preferred.

In preparing a formulation, HS6 may be admixed with one of several carriers, diluents, adjuvants, excipients or scaffold materials. For example, HS6 may be admixed with one or more of a bone void filler; β-Tricalcium phosphate; calcium carbonate; calcium sulfate; collagen; demineralised bone matrix; hydroxyapatite; hyaluronic acid; a gel or hydrogel; a growth factor; allograft material (e.g. Cortical Cancellous Chips (CCC) or Cancellous bone matrix (CBM)); autograft material (e.g. Cortical Cancellous Chips (CCC) or Cancellous bone matrix (CBM)); a heat sensitive copolymer; platelets or platelet gels; a bioactive silicate; a ceramic; carboxymethyl cellulose.

In some embodiments HS6 is formulated as a handling agent, e.g. to assist handling of biological material mixed with the HS6. In some embodiments HS6 is formulated as a viscous formulation, e.g. with hyaluronic acid or with carboxymethyl cellulose. In some embodiments HS6 is formulated on a titanium or ceramic implant substrate.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with HS6 and optionally one or more other pharmaceutically acceptable ingredients, including, for example, penetration, permeation, and absorption enhancers. Formulations may also suitably be provided in the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for topical or transdermal administration may be preferred and may include gels, sprays, pastes, ointments, creams, lotions, salves, oils, aqueous solutions, suspensions, and dispersions as well as patches, adhesive plasters, bandages, dressings, depots, and reservoirs.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

Topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired pharmaceutical properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

HS6 could be applied to a number of therapeutic applications in skin care that include wound healing and coating technology for wound dressings. As such, formulations may suitably be provided as a patch, adhesive plaster, bandage, dressing, tissue scaffold (e.g. see Zhong et al., Tissue scaffolds for skin wound healing and dermal reconstruction. Science 1997 Apr. 4; 276(5309):75-81), a biomaterial or the like which is impregnated with, or coated with, HS6 and optionally one or more other pharmaceutically acceptable ingredients, including, for example, penetration, permeation, and absorption enhancers.

Pharmaceutical compositions, medicaments, and other formulations comprising HS6 may also comprise PDGF-B, or PDGF-BB, or a heterodimer comprising PDGF-B. Owing to the ability of HS6 to bind PDGF-B/PDGF-BB, the HS6 may act as a carrier of PDGF-B/PDGF-BB assisting in delivery of PDGF-B/PDGF-BB to the wound site.

Administration is preferably in a "therapeutically effective amount", this being sufficient to repair and/or regenerate the skin. The actual amount administered, and rate and time-course of administration, will depend on the nature and severity of the fracture. Prescription of treatment, e.g. decisions on dosage etc., is within the responsibility of general practitioners and other medical doctors, and will typically take account of the nature of the fracture, the condition of the individual patient, the site of delivery, the method of administration and other factors known to practitioners. Single or multiple administrations of HS6 doses may be administered in accordance with the guidance of the prescribing medical practitioner. Purely by way of example, HS6 may be delivered in dosages of at least 1 ng/ml, more preferably at least 5 ng/ml and optionally 10 ng/ml or more. Individual HS6 dosages may be of the order less than 1 mg and greater than 1 µg, e.g. one of about 5 µg, about 10 µg, about 25 µg, about 30 µg, about 50 µg, about 100 µg, about 0.5 mg, or about 1 mg. Examples of the techniques and protocols mentioned above can be found in Remington's Pharmaceutical Sciences, 20th Edition, 2000, pub. Lippincott, Williams & Wilkins.

HS6 may be used to repair and/or regenerate skin alongside other treatments, such as administration of pain relieving or anti-inflammatory medicaments.

HS6 can be administered to a subject as a pharmaceutically acceptable salt thereof. For example, base salts of the compounds of the enriched mixtures of the present invention include, but are not limited to, those formed with pharmaceutically acceptable cations, such as sodium, potassium, lithium, calcium, magnesium, ammonium and alkylammonium. The present invention includes within its scope cationic salts, for example the sodium or potassium salts.

It will be appreciated that the compounds of the present invention which bear a carboxylic acid group may be delivered in the form of an administrable prodrug, wherein the acid moiety is esterified (to have the form —CO2R'). The term "pro-drug" specifically relates to the conversion of the —OR' group to a —OH group, or carboxylate anion therefrom, in vivo. Accordingly, the prodrugs of the present invention may act to enhance drug adsorption and/or drug delivery into cells. The in vivo conversion of the prodrug may be facilitated either by cellular enzymes such as lipases and esterases or by chemical cleavage such as in vivo ester hydrolysis.

Medicaments and pharmaceutical and cosmetic compositions according to aspects of the present invention may be formulated for administration by a number of routes, including but not limited to, injection at the site of disease or injury. The medicaments and compositions may be formulated in fluid or solid form. Fluid formulations may be formulated for administration by injection to a selected region of the human or animal body.

Glycosaminoglycans

As used herein, the terms 'glycosaminoglycan' and 'GAG' are used interchangeably and are understood to refer to the large collection of molecules comprising an oligosaccharide, wherein one or more of those conjoined saccharides possess an amino substituent, or a derivative thereof. Examples of GAGs are chondroitin sulfate, keratan sulfate, heparin, dermatan sulfate, hyaluronate and heparan sulfate.

As used herein, the term 'GAG' also extends to encompass those molecules that are GAG conjugates. An example of a GAG conjugate is a proteoglycosaminoglycan (PGAG, proteoglycan) wherein a peptide component is covalently bound to an oligosaccharide component.

In preferred embodiments the GAG is heparan sulphate.
Heparan Sulphate (HS)

Heparan sulfate proteoglycans (HSPGs) represent a highly diverse subgroup of proteoglycans and are composed of heparan sulfate glycosaminoglycan side chains covalently attached to a protein backbone. The core protein exists in three major forms: a secreted form known as perlecan, a form anchored in the plasma membrane known as glypican, and a transmembrane form known as syndecan. They are ubiquitous constituents of mammalian cell surfaces and most extracellular matrices. There are other proteins such as agrin, or the amyloid precursor protein, in which an HS chain may be attached to less commonly found cores.

Preferred embodiments of the present invention concerns HS chains isolated from their core protein. HS chains can be readily separated and isolated from the core protein, e.g. by neuramidase treatment.

"Heparan Sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O-, 6-O- and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulfate side chains consist of alternately arranged D-glucuronic acid or L-iduronic acid and D-glucosamine, linked via (1→4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), J. Biol. Chem. 273(8), 4350-4359, which is herein incorporated by reference in its entirety).

It is hypothesized that the highly variable heparan sulfate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulfate glycosaminoglycans may be genetically described (Alberts et al. (1989) Garland Publishing, Inc, New York & London, pp. 804 and 805), heparan sulfate glycosaminoglycan species isolated from a single source may differ in biological activity.

The biospecificity of targeted, affinity-purified HS preparations makes them very attractive for many therapeutic applications, including potential use to increase the efficiency of the biomolecule delivery and activity. Use of HS as carrier for growth factor delivery system, particularly PDGF, would be supported by demonstration of increased affinities for appropriate PDGF isoforms. Tissue repair and regeneration involve complex biological processes, in particular due to the fact that multiple growth factors and chemokines are locally expressed within distinct time frames. These biomolecules induce various signals at an optimized ratio in a defined spatiotemporal pattern to target specific cell types, underlining that orchestrated activities of each molecule are required in forming functional tissue, and must be considered for the development of an ideal delivery system. In comparison with other polysaccharides that bind to growth factors, such as heparin, which is a mixture of complex polymers varying in charge and chemical configuration, the control of the successive procedures of HS6 manufacture represents a major advantage allowing reproducible preparation of well-characterized, functionalized sugar, at scale. Moreover, control of the degree of substitution of each chemical group allows targeting of the binding of a specific biological mediator in an easier manner than with heparin, which bears different structural microdomains that offer various biological properties into the same macromolecule, and which can interfere with many components in the extracellular environment.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 µl of 0.5 M $H_2SO_4$ and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 µl of $HNO_2$ was added to GAG samples resuspended in 20 µl of $H_2O$, and vortexed before being incubated for 15 min at 25° C. with occasional mixing. After incubation, 1 M $Na_2CO_3$ was added to the sample to bring it to pH 6. Next, 100 µl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulfation patterns are found. Note: The repeating disaccharide backbone of the heparan polymer is a uronic acid connected to the amino sugar glucosamine. "NS" means the amino sugar is carrying a sulfate on the amino group enabling sulfation of other groups at C2, C6 and C3. "NA" indicates that the amino group is not sulphated and remains acetylated.

For example, for depolymerisation in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 µg of HS and incubated at 37° C. for 16 h before stopping the reaction by heating to 70° C. for 5 min.

Di- and tetrasaccharides may be eluted by column chromatography, e.g. HPLC. Alternatively they may be analysed by capillary electrophoresis.

Biomaterials

Pharmaceutical compositions and medicaments of the invention may take the form of a biomaterial that is coated and/or impregnated with HS6. An implant or prosthesis may be formed from the biomaterial. Such implants or prostheses may be surgically implanted to assist wound healing or tissue regeneration.

HS6 may be applied to implants or prostheses to accelerate new tissue formation at a desired location. It will be appreciated that heparan sulphates, unlike proteins, are particularly robust and have a much better ability to withstand the solvents required for the manufacture of synthetic bioscaffolds and application to implants and prostheses.

The biomaterial may be coated or impregnated with HS6. Impregnation may comprise forming the biomaterial by mixing HS6 with the constitutive components of the biomaterial, e.g. during polymerisation, or absorbing HS6 into the biomaterial. Coating may comprise adsorbing the HS6 onto the surface of the biomaterial.

The biomaterial should allow the coated or impregnated HS6 to be released from the biomaterial when administered to or implanted in the subject. Biomaterial release kinetics may be altered by altering the structure, e.g. porosity, of the biomaterial.

In addition to coating or impregnating a biomaterial with HS6, one or more biologically active molecules may be impregnated or coated on the biomaterial. For example, at least one chosen from the group consisting of: PDGF-B, PDGF-BB, BMP-2, BMP-4, OP-1, FGF-1, FGF-2, TGF-β1, TGF-β2, TGF-β3; VEGF; collagen; laminin; fibronectin; vitronectin.

Biomaterials coated or impregnated with HS6 may be useful in both medical and veterinary purposes. It will be appreciated that the present invention may improve the quality of life of a patient or potentially extend the life of an animal, for example a valuable racehorse for use in breeding.

The biomaterial provides a scaffold or matrix support. The biomaterial may be suitable for implantation in tissue, or may be suitable for administration (e.g. as microcapsules in solution).

The implant or prosthesis should be biocompatible, e.g. non-toxic and of low immunogenicity (most preferably non-immunogenic). The biomaterial may be biodegradable such that the biomaterial degrades as wound healing occurs, ultimately leaving only the regenerated tissue in situ in the subject. Alternatively a non-biodegradable biomaterial may be used, e.g. to guide tissue regeneration over a large discontinuity and/or to act as a structural support during healing, with surgical removal of the biomaterial being an optional requirement after successful wound healing.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium.

The biomaterial may have a porous matrix structure which may be provided by a cross-linked polymer. The matrix is preferably permeable to nutrients and growth factors required for bone growth.

Matrix structures may be formed by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of: agarose, collagen, fibrin, chitosan, polycaprolactone, poly(DL-lactide-co-caprolactone), poly(L-lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019,087; Tanaka, S.; Takigawa, T.; Ichihara, S. & Nakamura, T. Mechanical properties of the bioabsorbable polyglycolic acid-collagen nerve guide tube Polymer Engineering & Science 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material. Fibrin glue enjoys widespread clinical application as a wound sealant, a reservoir to deliver growth factors and as an aid in the placement and securing of biological implants (Rajesh Vasita, Dhirendra S Katti. Growth factor delivery systems for tissue engineering: a materials perspective. *Expert Reviews in Medical Devices.* 2006; 3(1): 29-47; Wong C, Inman E, Spaethe R, Helgerson S. *Thromb. Haemost.* 2003 89(3): 573-582; Pandit A S, Wilson D J, Feldman D S. Fibrin scaffold as an effective vehicle for the delivery of acidic growth factor (FGF-1). *J. Biomaterials Applications.* 2000; 14(3); 229-242; DeBlois Cote M F. Doillon C J. Heparin-fibroblast growth factor fibrin complex: in vitro and in vivo applications to collagen based materials. *Biomaterials.* 1994; 15(9): 665-672.).

Luong-Van et al (In vitro biocompatibility and bioactivity of microencapsulated heparan sulphate Biomaterials 28 (2007) 2127-2136), incorporated herein by reference, describes prolonged localised delivery of HS from polycaprolactone microcapsules.

A further example of a biomaterial is a polymer that incorporates hydroxyapatite or hyaluronic acid.

The biomaterial can be supplemented with additional cells. For example, one can "seed" the biomaterial (or co-synthesise it) with stem cells such as mesenchymal stem cells, more preferably human mesenchymal stem cells.

The subject to be treated may be any animal or human. The subject is preferably mammalian, more preferably human. The subject may be a non-human mammal (e.g. rabbit, guinea pig, rat, mouse or other rodent (including cells from any animal in the order Rodentia), cat, dog, pig, sheep, goat, cattle (including cows, e.g. dairy cows, or any animal in the order Bos), horse (including any animal in the order Equidae), donkey, and non-human primate). The non-human mammal may be a domestic pet, or animal kept for commercial purposes, e.g. a race horse, or farming livestock such as pigs, sheep or cattle. The subject may be male or female. The subject may be a patient.

Methods according to the present invention may be performed in vitro or in vivo, as indicated. The term "in vitro" is intended to encompass procedures with cells in culture whereas the term "in vivo" is intended to encompass procedures with intact multi-cellular organisms.

Dosages of Heparan Sulphate

In both in vitro and in vivo uses, HS6 may be used in concentrations or dosages of about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, 5 ng/ml or less; or of about 100 mg or less, 50 mg or less, 40 mg or less, 30 mg or less, 20 mg or less, 10 mg or less, 5 mg or less, 4 mg or less, 3 mg or less, 2 mg or less, or 1 mg or less; or about between 0.3-5 µg/ml, 0.3-4, 0.3-3, 0.3-2.5, 0.3-2, 0.3-1.5, 0.3-1.0, 0.3-0.9, 0.3-0.8, 0.3-0.7, 0.3-0.6, 0.3-0.5, 0.3-0.4, 1-2, 1-1.75, 1-1.5, 1-1.25, 1.25-2, 1.5-2, or 1.75-2 µg/ml.

PDGF-B and PDGF-BB

Platelet-derived growth factor (PDGF) is a pleiotropic growth factor regulating the growth, migration and differentiation of a wide variety of responsive cells. PDGF plays critical roles in such physiological processes as embryogenesis, inflammation and wound repair, but is also implicated in a variety of diseases such as fibrotic conditions and chronic wounds, atherosclerosis and malignancies. Because of its natural and powerful activity of stimulating wound healing, recombinant human PDGF has been made available for clinical use for targeting wound repair and tissue regeneration. Structurally, the classical PDGF isoforms are disulfide linked dimers of homologous A- and B-polypeptide chains, arranged as homodimers (PDGF-AA, PDGF-BB) or as a heterodimer (PDGF-AB). The biological effects of PDGF are exerted by binding to two structurally related tyrosine kinase receptors, denoted a- and b-receptors. The PDGF isoforms interact differentially with each of the two receptors, establishing one basis for the diversity of function of PDGF isoforms. PDGF-BB binds with similar affinity to the PDGF a- and b receptors, whereas PDGF-AA interacts effectively only with the PDGF a-receptor. The role of HS sugars in these interactions is not yet clear.

PDGF belongs to the heparin-binding growth factor family and interacts with heparin and especially with the GAG component of heparan sulfate proteoglycans (HSPG). The binding involves electrostatic interactions between basic residues in the C-terminal extremity of PDGF chains and negatively charged HSPG. However, while it is well documented that heparan sulfate (HS) can increase the efficiency of the prototypic heparin-binding growth factor fibroblast growth factor (FGF)-2 by stabilizing ligand receptor complexes and inducing the subsequent activation of the receptor tyrosine kinase, the role of HS on the biological functions of PDGF remains unclear. HS and heparin have been shown to inhibit PDGF mitogenic activity in human smooth muscle cells through inhibition of activated MAPK. In heparan sulfate-deficient cells heparin increased PDGF-BB-induced chemotaxis by modulating PDGF receptor phosphorylation, MAPK and Akt downstream signaling (Rolny C, Spillmann D, Lindahl U, Claesson-Welsh L. Heparin amplifies platelet-derived growth factor (PDGF)-BB-induced PDGF alpha-receptor but not PDGF beta-receptor tyrosine phosphorylation in heparan sulfate-deficient cells. J Biol Chem 2002; 277:1931).

In this specification PDGF-B refers to platelet derived growth factor B (monomer). In physiological conditions PDGF-B is usually found as a dimer, either a homodimer PDGF-BB or a heterodimer, e.g. PDGF-AB formed with PDGF-A.

The HS6 preparation of the present invention was designed to enrich for an HS sugar with a measurable affinity for the mitogen PDGF-BB. HS6 preferably binds to PDGF-B or PDGF-BB and the terms are used interchangeably herein.

The major contributors to HS-PDGF-BB binding may be ionic interactions between negatively charged carboxyl and sulfate groups in HS and the appropriately configured basic amino acid residues of PDGF-BB, as has been demonstrated for the interaction of PDGF-A chain with HS, and for protein-GAG binding in general. However, other types of interaction may contribute to binding, such as van der Waals forces, hydrogen bonds and hydrophobic interactions between the protein and the carbohydrate backbone. The idea that the secondary and tertiary structures of the growth factor may be involved for an efficient and specific binding of the growth factor to HS6 is reinforced by the fact that compositions of potentiating HS derivatives differ between PDGF and BMP2. The binding capacity of PDGF-BB for polysaccharide polymers presumably reflect the physiological capacity of PDGF isoforms to interact differentially with matrix- and cell GAG species, including HS and chondroitin sulfate, providing the means to modulate the bioavailability of the growth factor for responsive cells.

HS6 has less specificity for PDGF-BB than BMP2 does for HS3 (described in WO2010/030244). In particular, HS6 also exhibits binding to BMP2 and FGF2, and some affinity for VEGF-165. This may contribute to the advantageous properties of HS6 in terms of promoting healing and regeneration.

An amino acid sequence for PDGF-B is shown in FIG. 7.

The amino acid sequence of human PDGF-B can be found in GenBank under accession no. NP_002599.1 GI:4505681 in which SEQ ID NO:1 starts at position 200.

In this specification "PDGF-B" or "PDGF-BB" includes proteins or polypeptides having at least 70%, more preferably one of 75%, 80%, 85%, 90%, 95%, 96%, 97%, 98%, 99% or 100% sequence identity with the amino acid sequence of PDGF-B illustrated in FIG. 7.

The PDGF-B or PDGF-BB protein or polypeptide preferably also includes a heparin binding domain having the amino acid sequence of SEQ ID NO:1, or an amino acid sequence having one of 75%, 80%, 85%, 90%, 95%, 96%, 97%, 98%, or 99% sequence identity to SEQ ID NO:1.

A PDGF-B protein or polypeptide may be a fragment or truncate of a full length PDGF-B protein or polypeptide.

The PDGF-B or PDGF-BB protein may be from, or derived from, any animal or human, e.g. non-human animals, e.g. rabbit, guinea pig, rat, mouse or other rodent (including from any animal in the order Rodentia), cat, dog, pig, sheep, goat, cattle (including cows, e.g. dairy cows, or any animal in the order Bos), horse (including any animal in the order Equidae), donkey, and non-human primate or other non-human vertebrate organism; and/or non-human mammalian animal; and/or human.

Dosages of PDGF-B or PDGF-BB

In both in vitro and in vivo uses, PDGF-B/PDGF-BB may be used in combination with HS6. In some cell culture methods of the present invention exogenous HS6 is added to the culture.

Suitable concentrations or dosages of PDGF-B/PDGF-BB include about 500 ng/ml or less, more preferably one of 250 ng/ml or less, 100 ng/ml or less, 90 ng/ml or less, 80 ng/ml or less, 70 ng/ml or less, 60 ng/ml or less, 50 ng/ml or less, 40 ng/ml or less, 30 ng/ml or less, 20 ng/ml or less, 10 ng/ml or less, 5 ng/ml or less; or of about 100 mg or less, 50 mg or less, 40 mg or less, 30 mg or less, 20 mg or less, 10 mg or less, 5 mg or less, 4 mg or less, 3 mg or less, 2 mg or less, or 1 mg or less; or between about range 0.1-5 ng/ml, 0.1-0.2, 0.1-0.3, 0.1-0.4, 0.1-0.5, 0.1-0.6, 0.1-0.7, 0.1-0.8, 0.1-0.9, 0.1-1.0, 0.1-1.5, 0.1-2.0, 0.1-2.5, 0.1-3.0, 0.1-3.5, 0.1-4.0, 0.1-4.5, 0.1-5.0 ng/ml.

In some embodiments, in vitro and in vivo uses of HS6 exclude the addition of exogenous PDGF-B/PDGF-BB. For example, in some cell culture methods of the present invention exogenous PDGF-B/PDGF-BB is not added to the culture.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 6. Chart showing that N-sulfation is crucial for PDGF-BB binding.

FIG. 7. Amino acid sequence of PDGF-B showing the heparin binding domain of SEQ ID NO:1 in bold. PDGF-B peptide (SEQ ID NO:1) was selected based on the highly basic region of PDGF-BB sequence. Note the basic amino acids: Arginine (R), Lysine (K), Histidine (H).

FIG. 26. Table showing proportion of disaccharides in heparin lyase digests of the HS samples as determined by HPLC-SEC-RI.

FIG. 27. Table showing disaccharide composition of heparin lyase digested HS samples: Celsus HS, HS6+, HS6−.

EXAMPLES

Example 1: Surface Plasmon Resonance (SPR)

1. Heparin was biotinylated using N-hydroxysuccinimide-biotin (NHS-biotin) (Pierce).
2. Streptavidin (SA) sensor chip (GE Healthcare) was coated with biotinylated heparin using an in-built immobilisation protocol on Biacore T100 (GE Healthcare), with a targeted 40 response units (RUs).
3. Recombinant PDGF-BB (R&D) was prepared at 12.5 nM to 800 nM concentrations in HBS-EP-0.1 running buffer (10 mM HEPES, 150 mM NaCl, 3 mM EDTA, 0.1% Tween-20 (v/v) pH 7.4).
4. PDGF-BB samples were then injected over the heparin-coated surface at a flow rate of 30 µL/min for 120 s, with HBS-EP-0.1 being subsequently passed over the surface for a further 600 s to monitor PDGF-BB dissociation. After dissociation, the sensor surface on the chip was regenerated by 2 washes of 2 M NaCl injected at 30 µL/min for 60 s.

Figure 1:
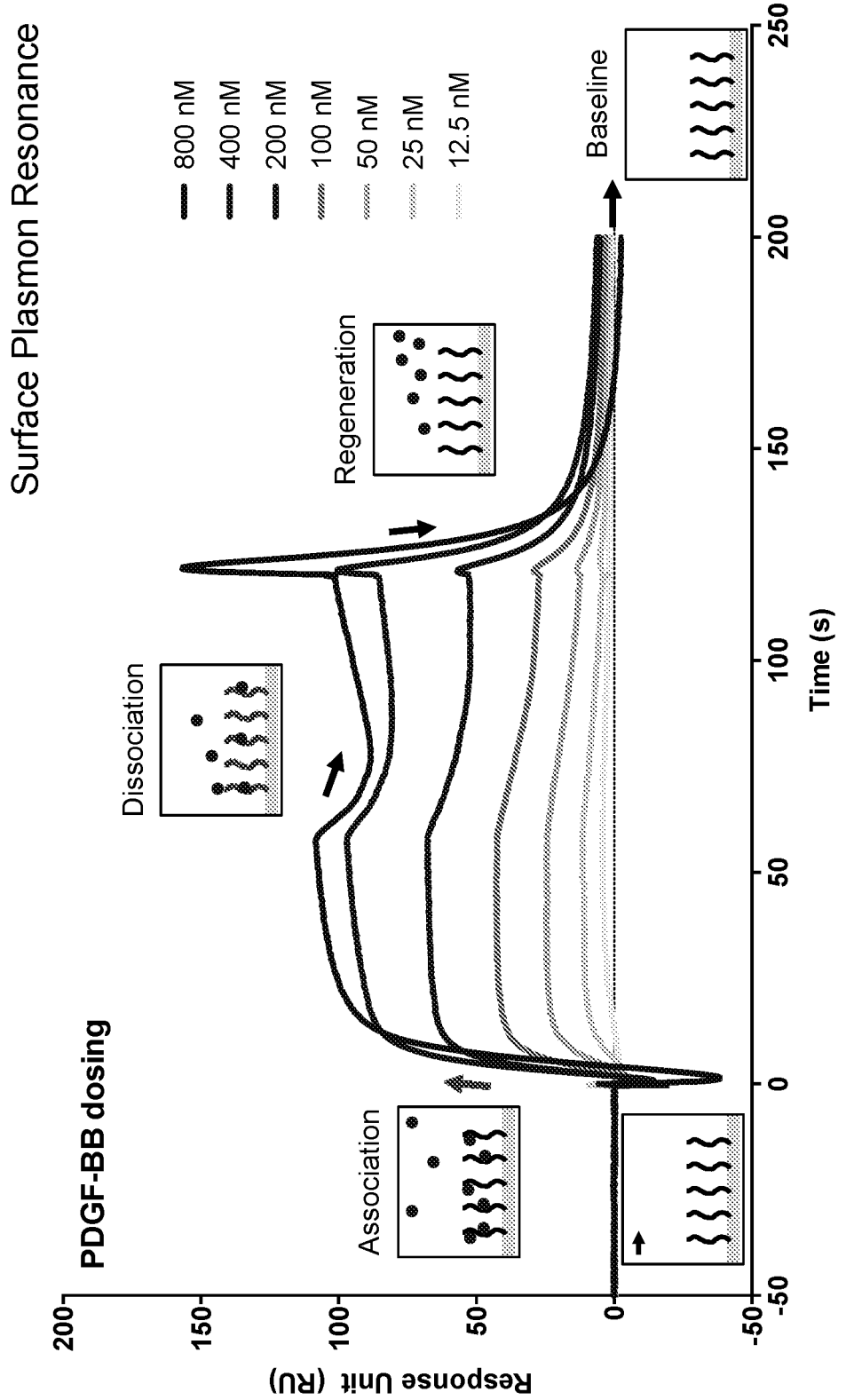
FIG. 1. Chart showing PDGF-BB binding to heparin.

Results:

PDGF-BB binds to the heparin coated chip in a dose dependent manner (FIG. 1).

50 nM PDGF-BB was selected for use in the competition experiments.

Example 2: PDGF-B Peptide Binds to Heparin and $HS^{PM}$

GAG Protocol:

1. GAG binding plate (Iduron) was coated with 200 µL/well of 5 µg/ml Heparin or heparan sulphate from porcine mucosa ($HS^{PM}$) prepared in Standard Assay Buffer (SAB, 100 mM NaCl, 50 mM Sodium Acetate, 0.2% (v/v) Tween-20, pH 7.2) overnight. Plates are protected from light at every incubation step.
2. Plates were washed thrice with SAB.
3. Add 250 µL/well of 0.4% (w/v) gelatin blocking solution and incubate at 37° C. for 1 hour.
4. Plates were washed thrice with SAB.
5. Add 200 µL/well of biotinylated PDGF-B peptide (SEQ ID NO:1) prepared at 100, 200 and 400 ng/mL in blocking solution and incubate at 37° C. for 1 hour.
6. Plates were washed thrice with SAB.
7. Add 200 µL/well of 220 ng/mL ExtrAvidin prepared in blocking solution and incubate at 37° C. for 30 minutes.
8. Plates were washed thrice with SAB.
9. Add 200 µL/well of Development Reagent SigmaFAST p-Nitrophenyl phosphate prepared in distilled water and incubate at room temperature for 40 minutes.
10. Read plate at 405 nm within one hour.

Figure 2A:
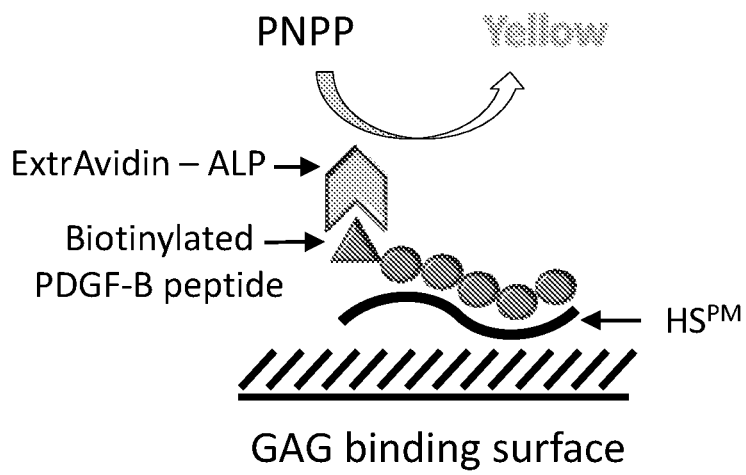
FIG. 2. (A) Illustration of PDGF-B:HS binding assay; (B) Chart showing PSGF-B binds to heparin and $HS^{PM}$.
Figure 2B:
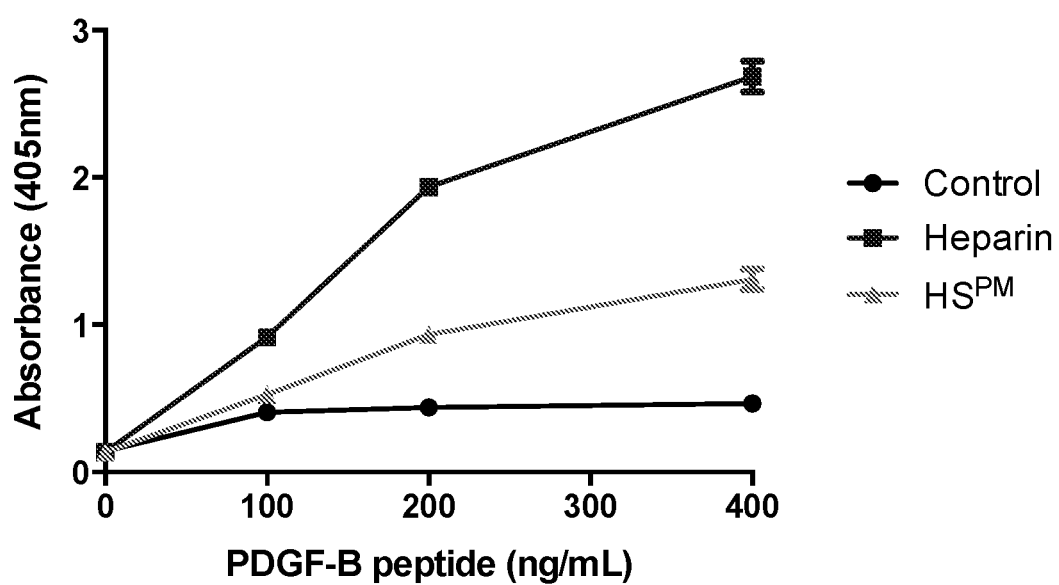
Figure 3A:
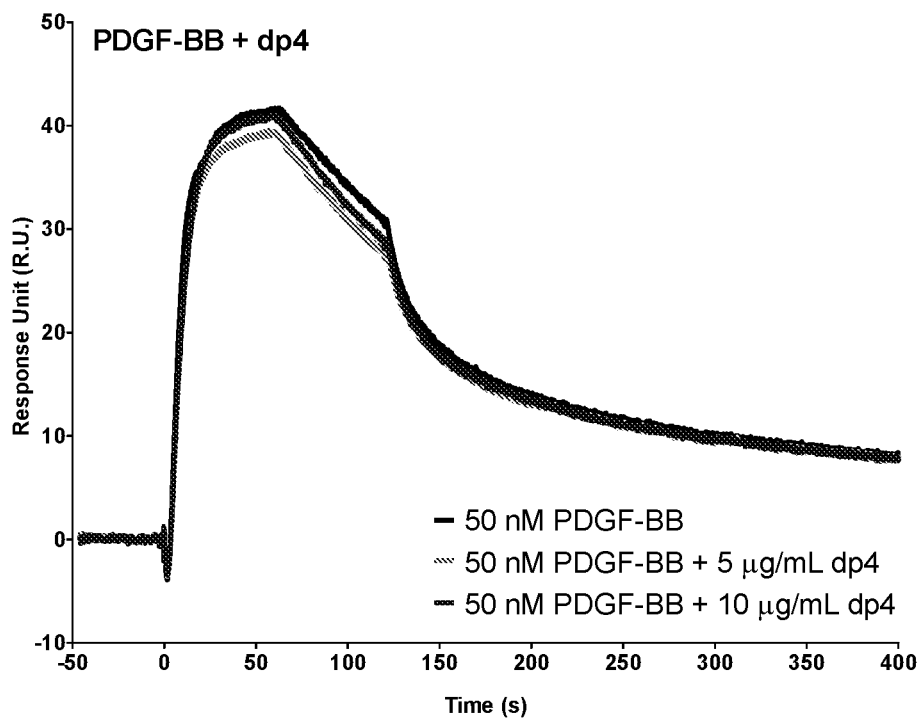
FIG. 3. Charts showing binding of heparin dp4-24 to PDGF-BB. (A) PDGF-BB+dp4, (B) PDGF-BB+dp8, (C) PDGF-BB+dp12, (D) PDGF-BB+dp16, (E) PDGF-BB+dp20, (F) PDGF-BB+dp24.
Figure 3B:
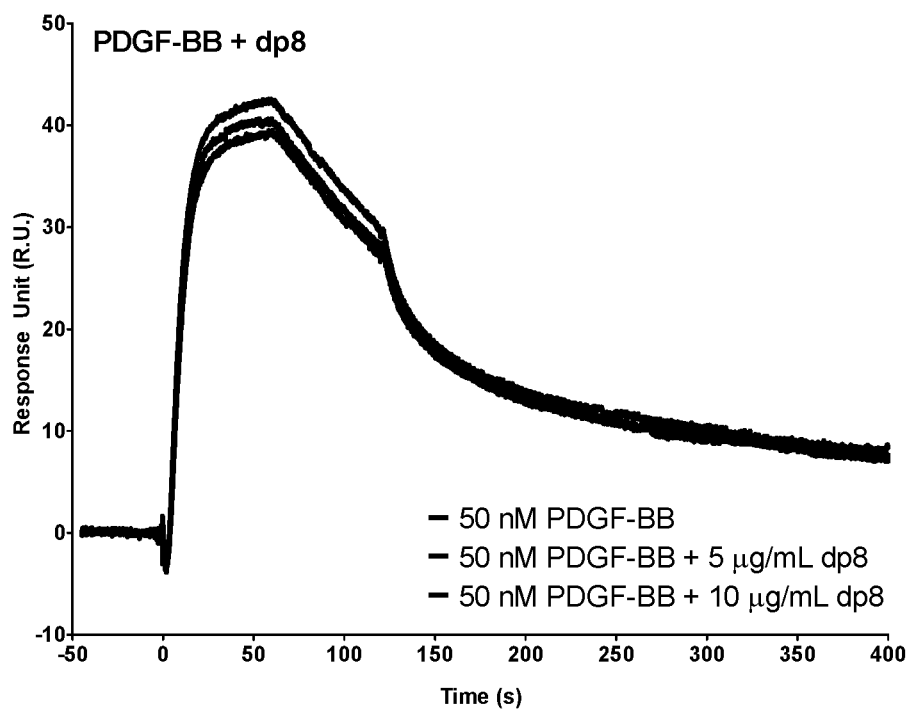
Figure 3C:
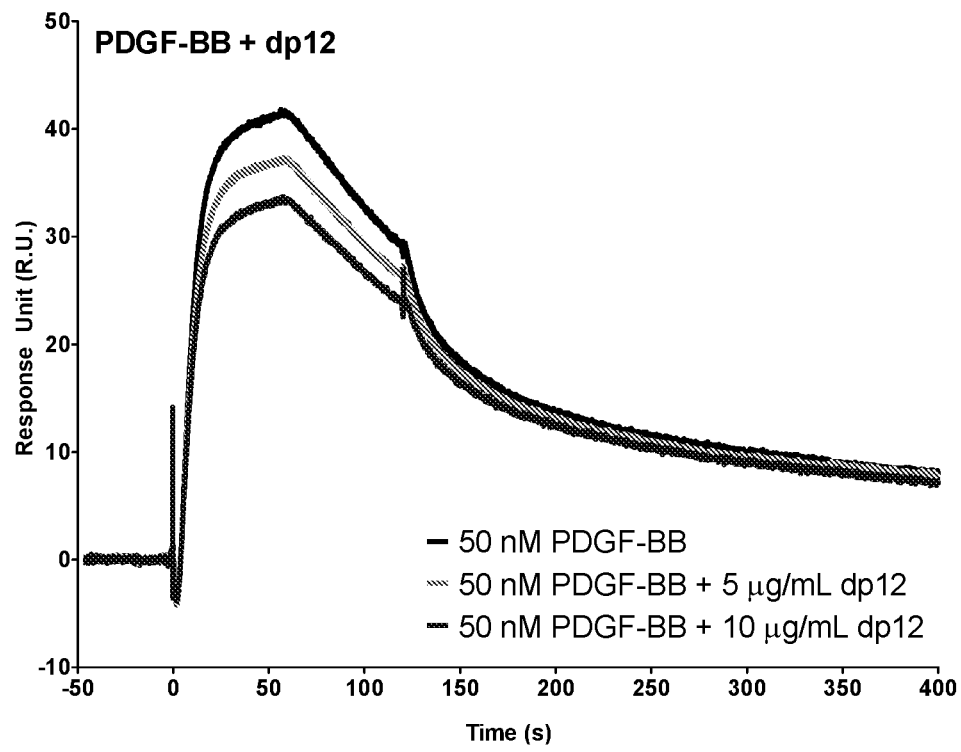
Figure 3D:
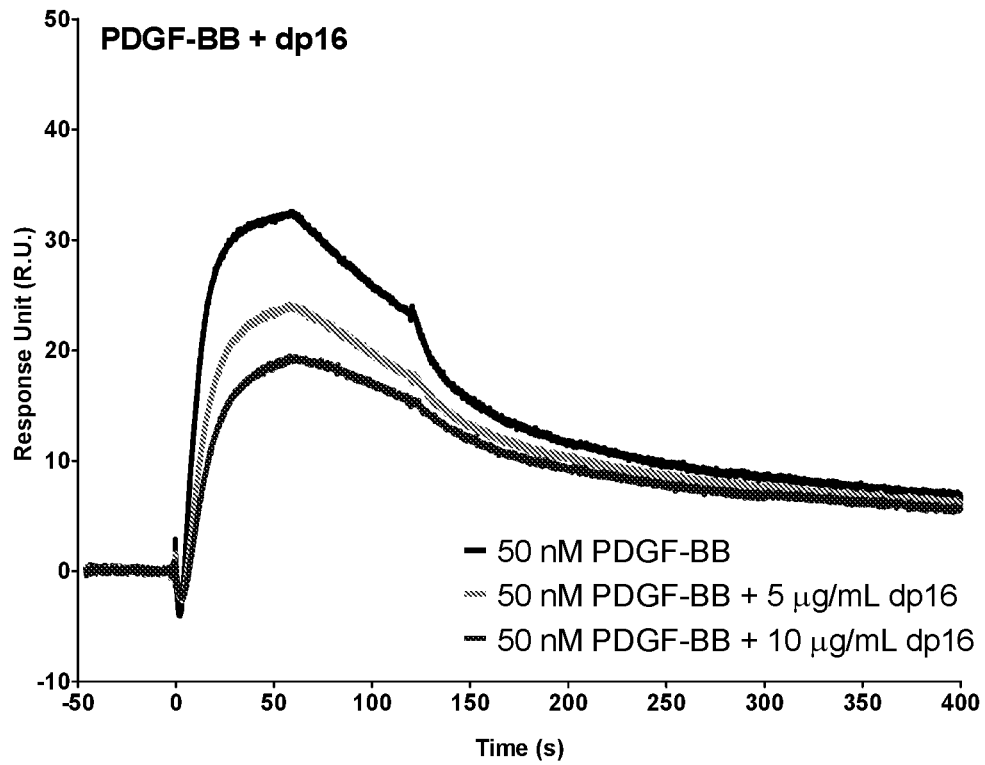
Figure 3E:
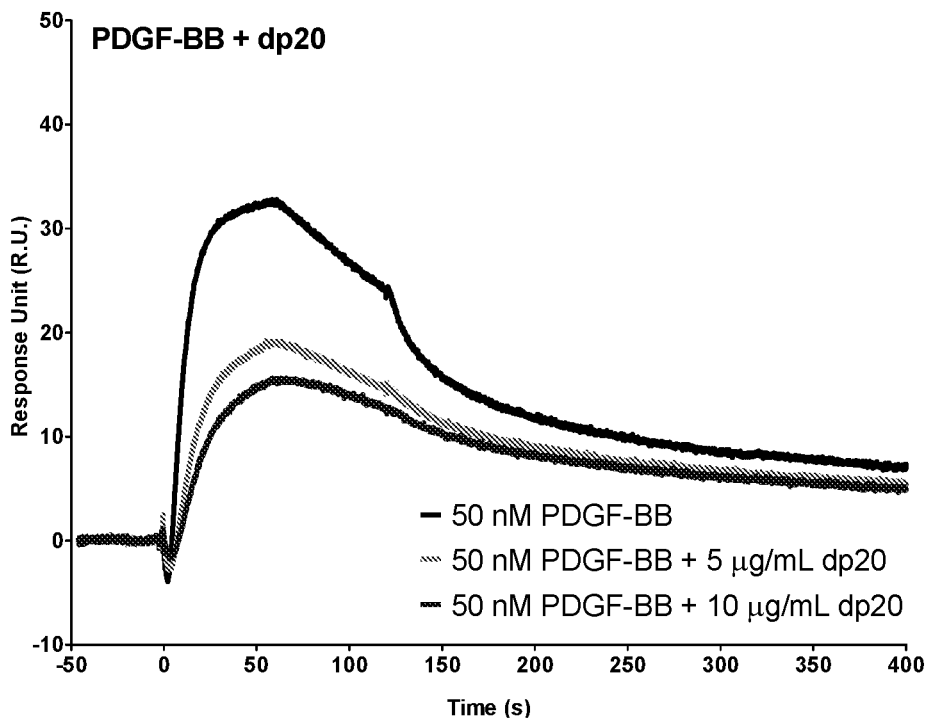
Figure 3F:
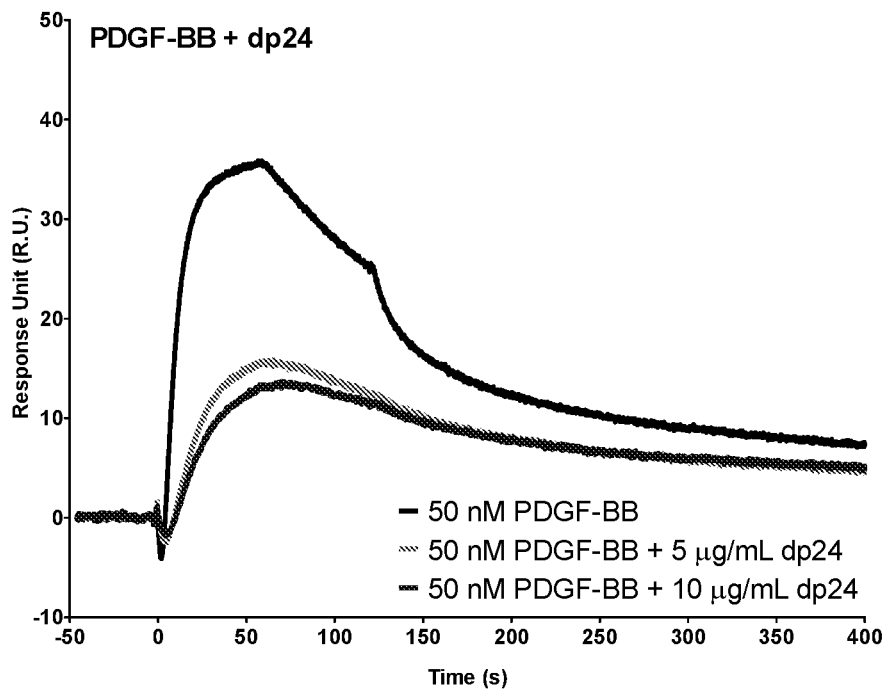

Results:

Biotinylated PDGF-B peptide binds to both Heparin and $HS^{PM}$ (FIG. 2).

PDGF-B peptide will bind to the highly sulfated Heparin more than $HS^{PM}$.

Results also shows that there are PDGF-B binding $HS^{PM}$ fractions.

PDGF-B peptide was selected for use in isolating PDGF-BB binding HS fraction (HS6).

Example 3: Binding of Heparin Dp4-24 to PDGF-BB

Competition Protocol:

1. Heparin and heparin derivatives (Iduron), including dp fragments and desulfated heparins, were prepared at 5 µg/ml and 10 µg/ml in HBS-EP-0.1 running buffer.
2. 50 nM PDGF-BB was prepared in HBS-EP-0.1 running buffer.
3. PDGF-BB and heparin/heparin derivatives were mixed.
4. PDGF-BB samples were then injected over the heparin-coated surface at a flow rate of 30 µL/min for 120 s, with HBS-EP-0.1 being subsequently passed over the surface for a further 600 s to monitor PDGF-BB dissociation. After dissociation, the sensor surface on the chip was regenerated by 2 washes of 2 M NaCl injected at 30 µL/min for 60 s.

Figure 4:
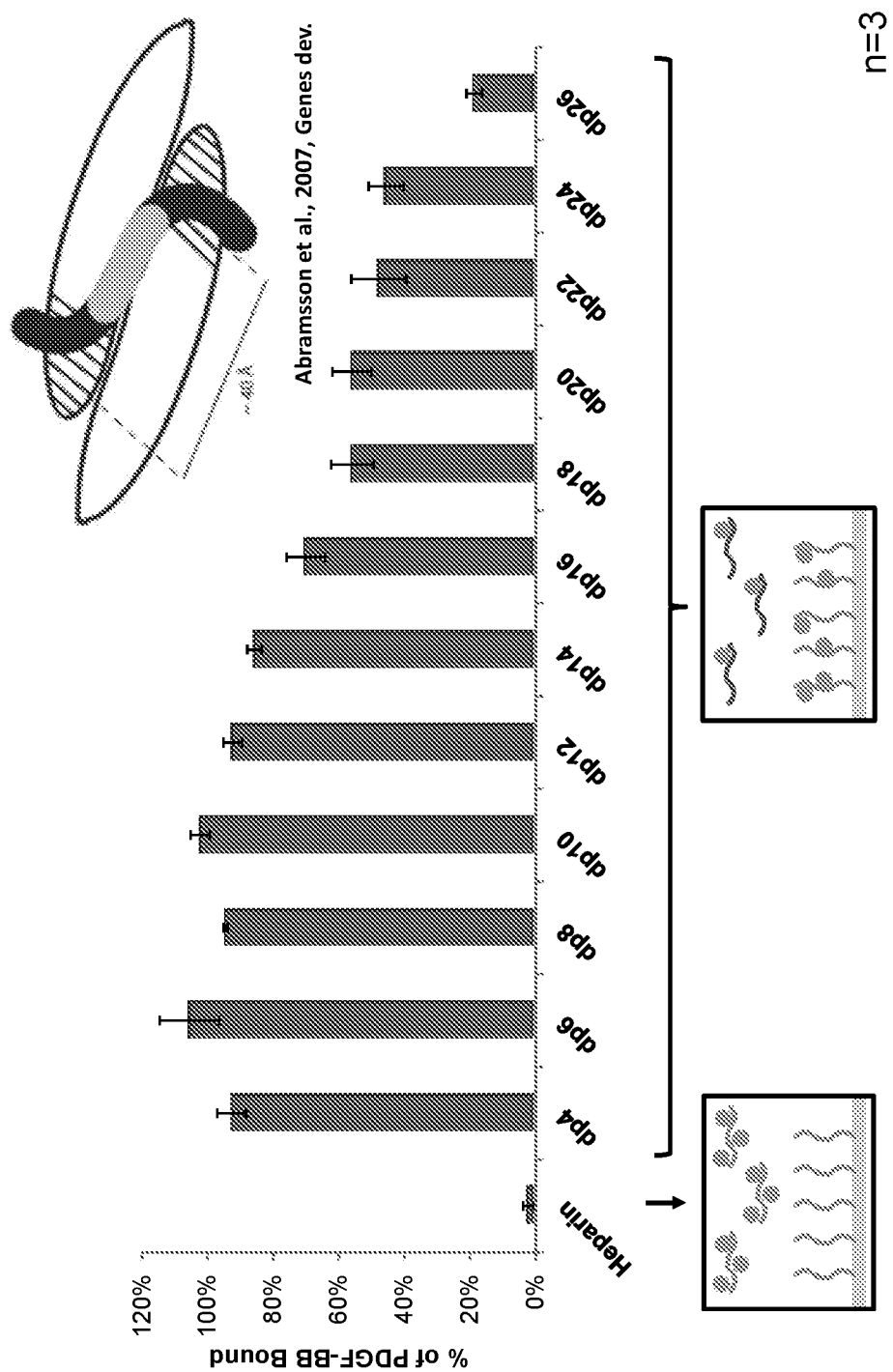
FIG. 4. Chart showing that binding of PDGF-BB increases with chain length.
Figure 5A:
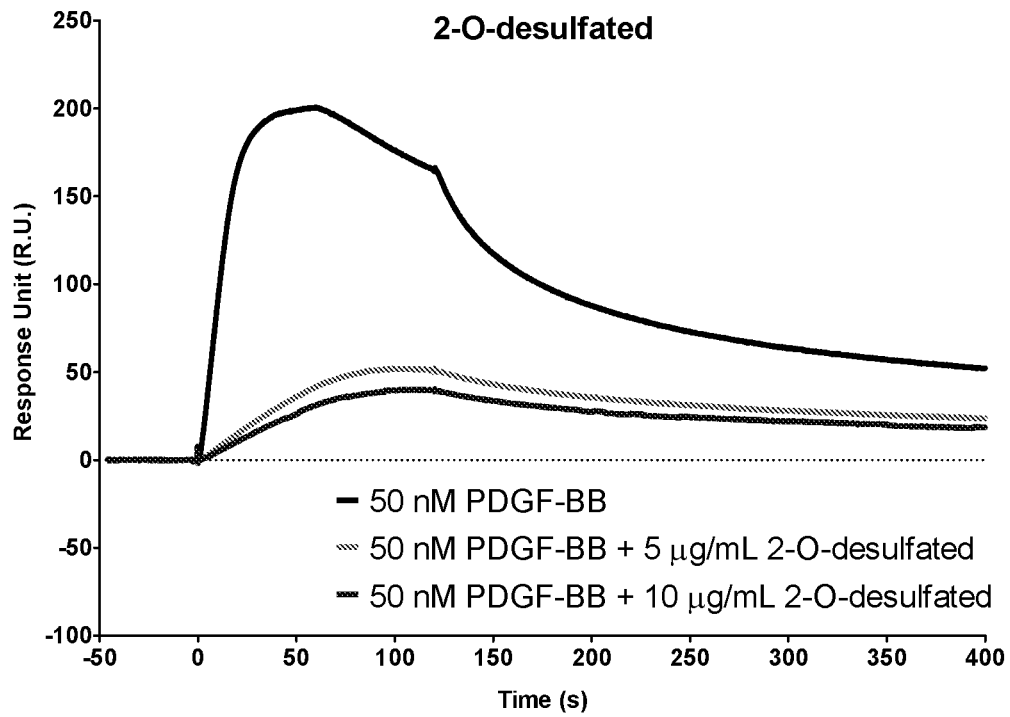
FIG. 5. Charts showing that N-sulfation is crucial for PDGF-BB binding. Effect of (A) 2-O-desulfation; (B) 6-O-desulfation; (C) N-desulfation; (D) N-desulfated reN-Acetylated.
Figure 5B:
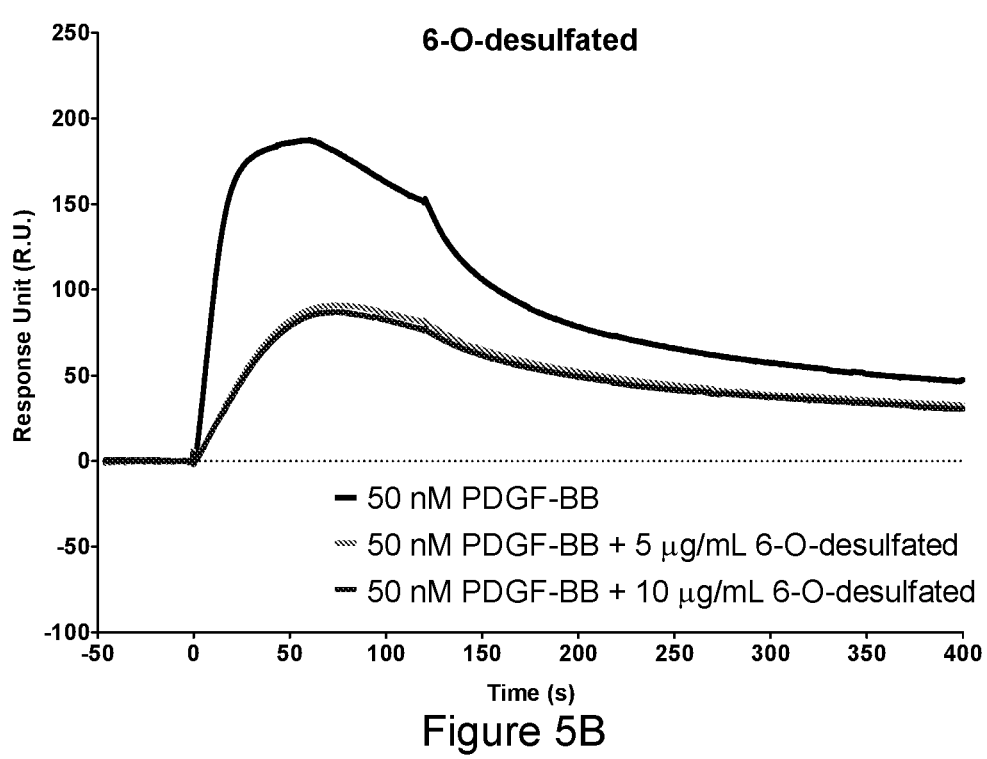
Figure 5C:
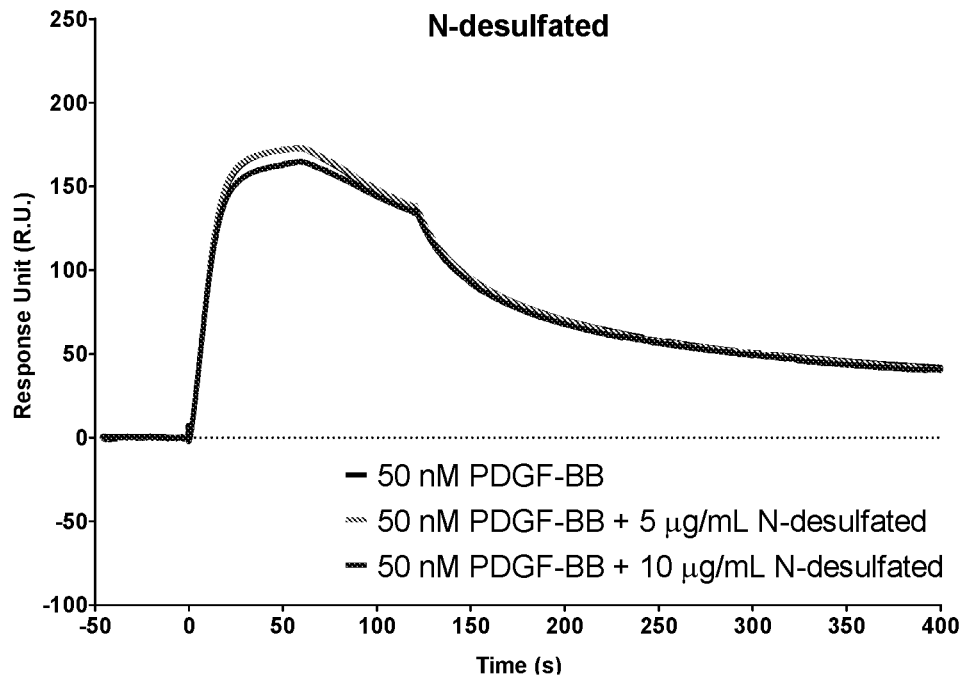
Figure 5D:
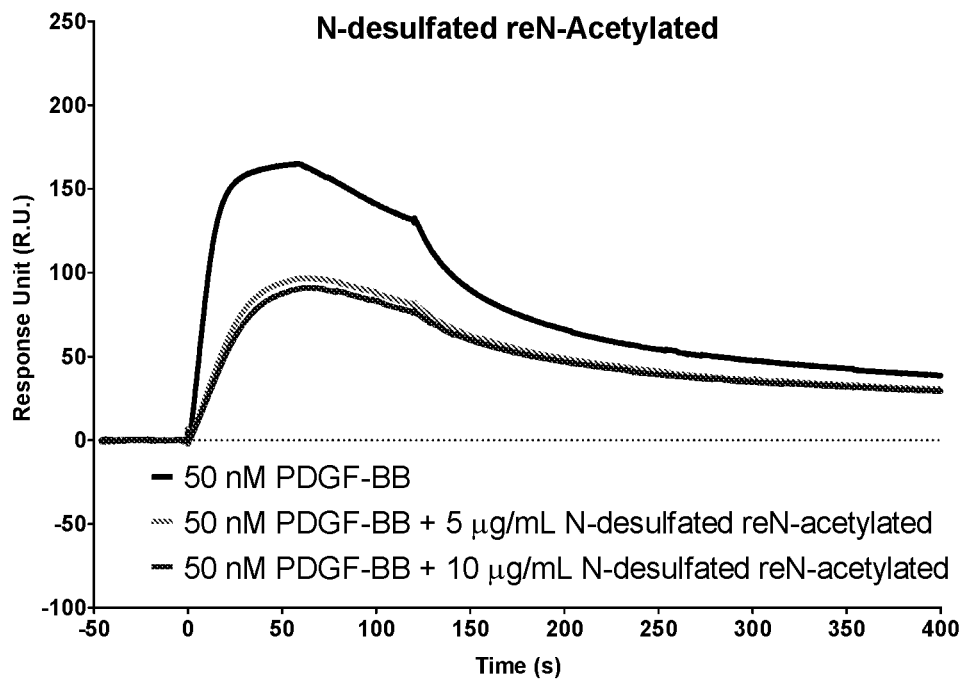
Figure 8:
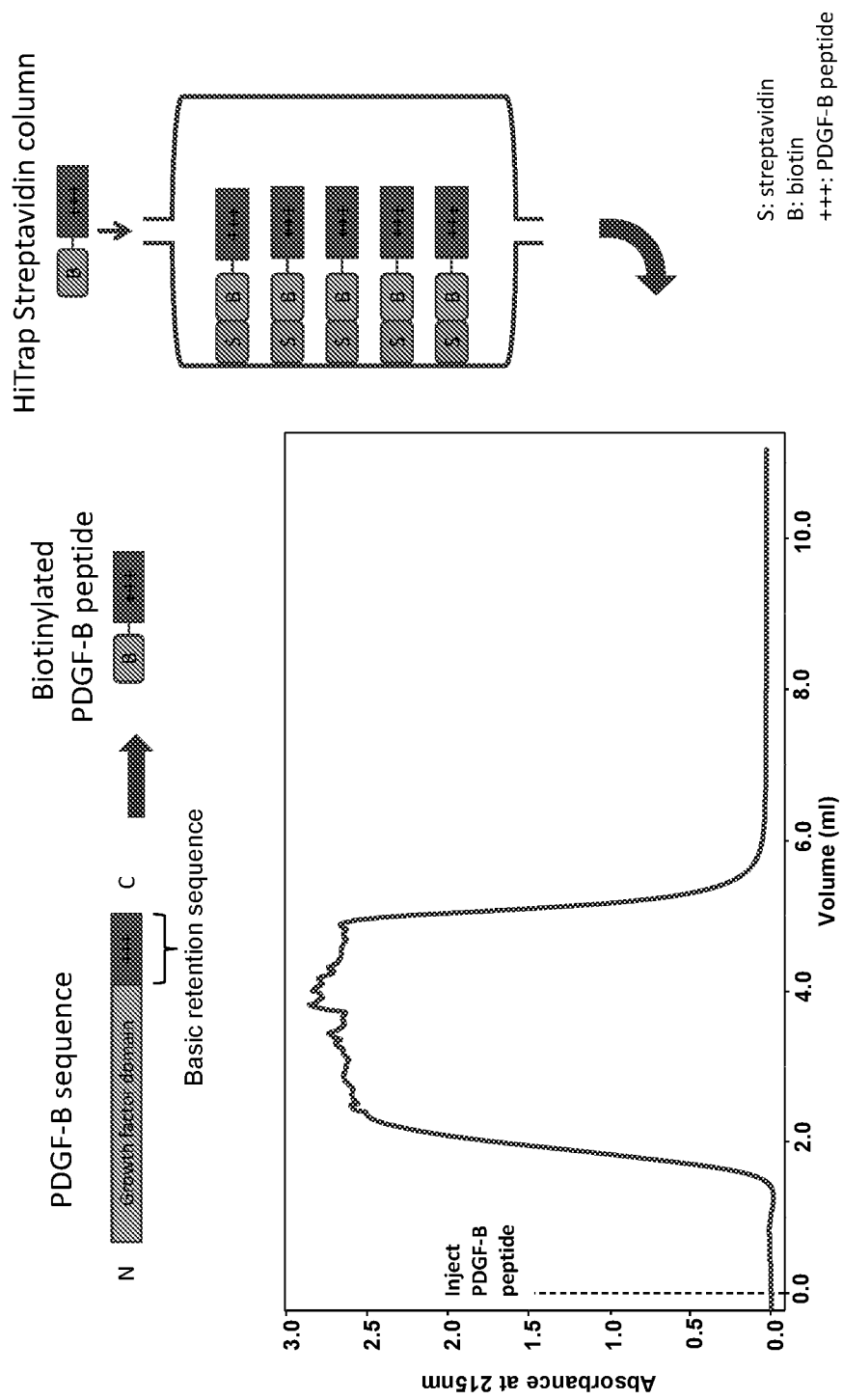
FIG. 8. Chromatogram from PDGF-B peptide coupled HiTrap Streptavidin column.
Figure 9:
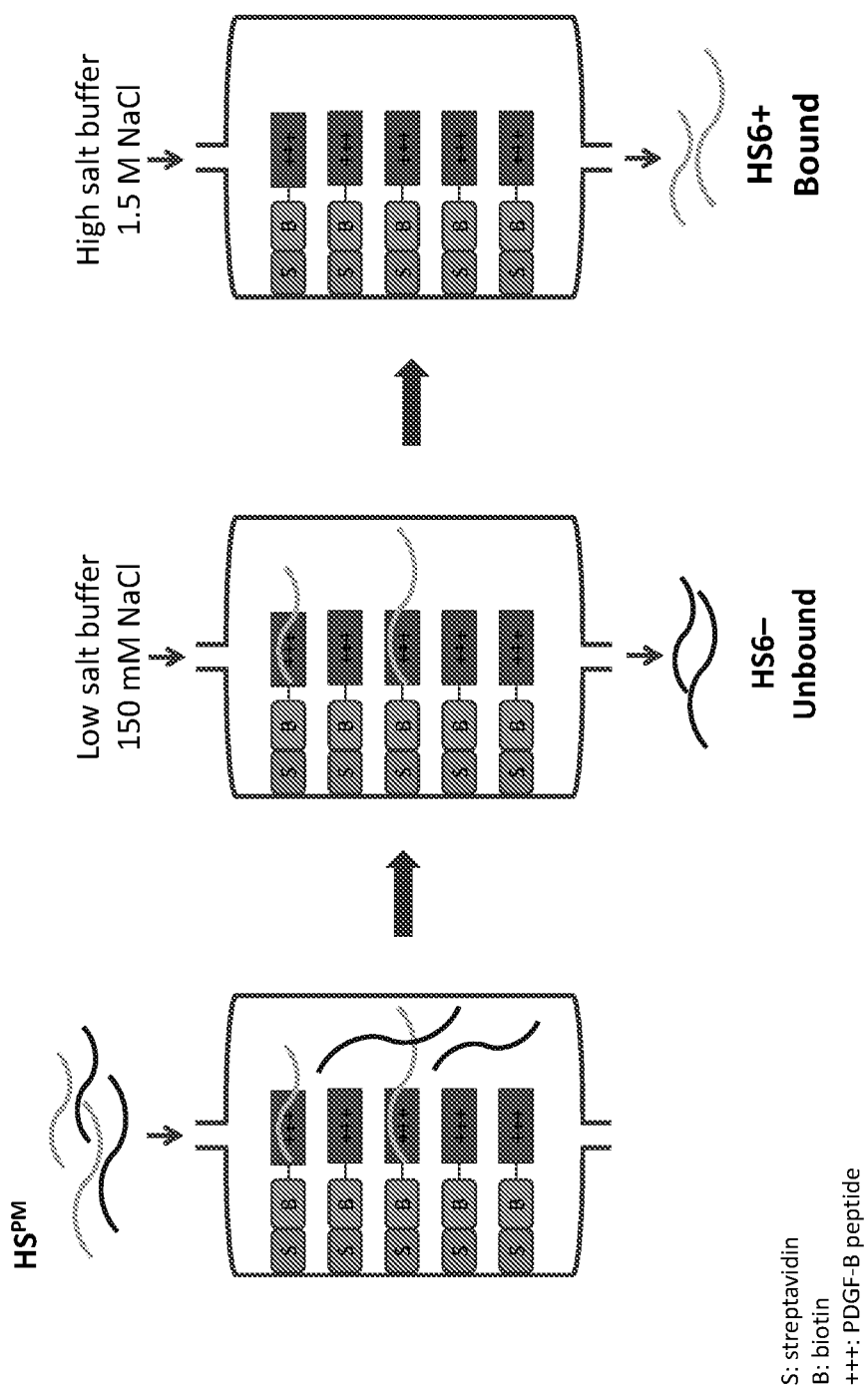
FIG. 9. Illustration of HS6 purification by affinity chromatography.

Results:

Binding of PDGF-BB increases with longer dp fragments (FIGS. 3 and 4).

The increased affinity that PDGF-BB has to the dp fragments results in decreased PDGF-BB binding to the heparin coated chip.

Example 4: N-Sulfation is Crucial for PDGF-BB Binding

The competition protocol from Example 3 was used, using the following heparin and heparin derivatives:

Desulfated heparin (Iduron): heparin that has been digested with enzymes to remove specific sulfations 2-O-deS: 2-O-desulfated heparin 6-O-deS: 6-O-desulfated heparin N-deS: N-desulfated heparin N-deS/R: N-desulfated Re-acetylated heparin Results:

N-sulfation is crucial for PDGF-BB binding (FIGS. 5 and 6).

Example 5: HS6 Purification

We investigated the purification of a new PDGF-BB binding heparan sulphate (HS) from commercially available Porcine Celsus Heparan sulphate sources (also called $HS^{PM}$) suitable for scale up of heparan sulphate (HS) preparations that can be readily used in the clinic.

The Heparin binding domain (HBD) peptide sequence RAKTPQTRVTIRTVRVRRPPKGKHRKFKHTHDK (SEQ ID NO: 1). from PDGF-B was selected and used to purify specific HS species capable of binding to PDGF-B and PDGF-BB.

Protocol:

1. 4 mg of biotinylated PDGF-BB peptide ((Biotin)K-AHX-RAKTPQTRVTIRTVRVRRPPKGKHRK-FKHTHDK [SEQ ID NO:2; AHX=6− aminohexanoic acid]) was coupled to HiTrap™ streptavidin HP column (GE Healthcare) at 1 mg/mL in low salt buffer (20 mM phosphate, 150 mM NaCl, pH 7.2) (FIG. 8).
2. $HS^{PM}$ (Celsus Laboratories Inc.) was dissolved at 1 mg/mL in low salt buffer.
3. For each run, 3 mL of 1 mg/mL $HS^{PM}$ was injected at 0.2 mL/min.
4. Column was washed in low salt buffer to elute the unbound material, until the baseline absorbance at 232 nm reached zero.
5. Bound HS was eluted with high salt buffer (20 mM phosphate, 1.5 M NaCl, pH 7.2) (FIG. 9).

Figure 10:
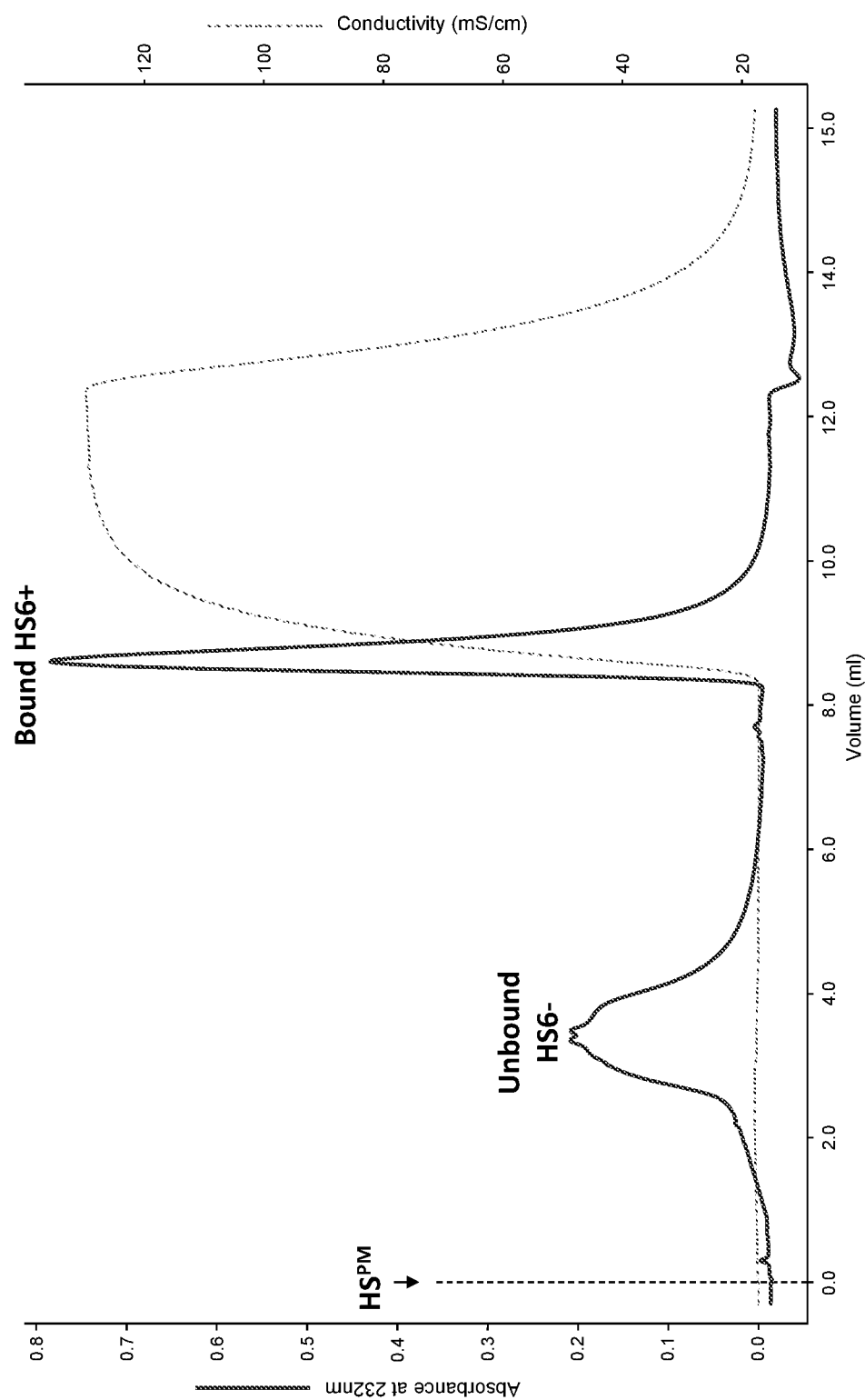
FIG. 10. Chromatogram showing HS6+ (bound fraction) and HS6− (unbound fraction).

6. Peak fractions of unbound and bound material were collected separately and freeze-dried (FIG. 10).
7. Samples were desalted on a HiPrep™ 26/10 desalting column (GE Healthcare) at a flow rate of 10 mL/min, freeze dried again and stored in a desiccator cabinet.

Results:

HS6−=HS fraction that does not bind to PDGF-B peptide in low salt buffer.

HS6+ (also called HS6)=HS fraction that binds to PDGF-B peptide in low salt buffer and eluted with high salt buffer.

Example 6: Analysis of HS6

Samples Used
Dry weight of HS preparations:

| | |
|---|---|
| HS6 +ve | 2.13 mg |
| HS6 −ve | 2.1 mg |

Included in this study as a control:

| | |
|---|---|
| Celsus HS 10697 | 2.0 mg |

Digestion of HS Samples with Heparin Lyase Enzymes

Heparan sulfate (HS) was from Celsus Laboratories Inc. (HO-03103, Lot # HO-10697). Heparin lyase I (Heparitinase, EC 4.2.2.8, also known as hepartinase I), heparin lyase II (heparitinase II, no EC number assigned) and heparin lyase III (heparinase, EC 4.2.2.7, also known as heparitinase III) were obtained from Ibex Technologies, Quebec, Canada. The enzymes, supplied as solutions (0.5 IU/50 µL) stabilised in 5% sucrose, were diluted with BSA (0.1% w/v solution in 50 mM sodium phosphate buffer; pH 7.1 containing 100 mM NaCl for heparin lyase I, pH 7.1 for heparin lyase II and pH 7.6 for heparin lyase III) and aliquots (5 mIU/5 µL) were stored frozen (−80° C.) until needed.

HS samples were solubilised in water (1 mg/mL) and aliquots (2×1 mL) of each were freeze-dried for analysis. The HS samples were digested to di- and oligosaccharides by the sequential addition of heparin lyase enzymes as described below (modified from the method of Brickman et al., 1998, Structural modification of fibroblast growth factor-binding heparan sulfate at a determinative stage of neural development. The Journal of Biological Chemistry, 273, 4350-4359). The dry HS samples (1 mg) were re-solubilised in 100 mM sodium acetate containing 2 mM calcium acetate (pH 7.0, 470 µL) and heparin lyase I (5 µL; 5 mIU) was added to each sample. The samples were incubated (37° C., 2 h) with gentle mixing on a rotating wheel (11 rpm). Heparin lyase III (5 µL; 5 mIU) was added and the samples were incubated for a further 1 h (as above). Heparin lyase II (5 µL; 5 mIU) was then added and the samples were incubated as above, for a further 18 h. Finally, aliquots (5 µL; 5 mIU) of all three heparin lyases were added simultaneously and the samples were incubated for a further 24 h. The enzyme digestion was terminated by heating (100° C., 5 min).

HPLC-SEC-RI of Digested HS Samples

The HPLC-SEC chromatograms were obtained using two Superdex™ Peptide 10/300 GL columns (300×10 mm, GE Healthcare, Buckinghamshire, UK) in series, on a Waters 2690 Alliance system with a Waters 2410 refractive index detector (range 64). The do/dc for quantification from the RI was set at 0.129 (Knobloch and Shaklee, 1997). Samples (2 mg/mL) were injected (50 µL; 100 µg) and eluted with 50 mM ammonium acetate (0.5 mL/min) at room temperature. Heparin oligosaccharide standards (Iduron Ltd, Manchester, UK and Dextra Laboratories Ltd, Reading, UK), previously run under the same conditions, were used for identification purposes. Run times for these columns were 120 min. Data was collected and analysed using DAWN Astra software (Version 4.73.04, Wyatt Technology Corp., Santa Barbara, Calif., USA).

Figure 25:
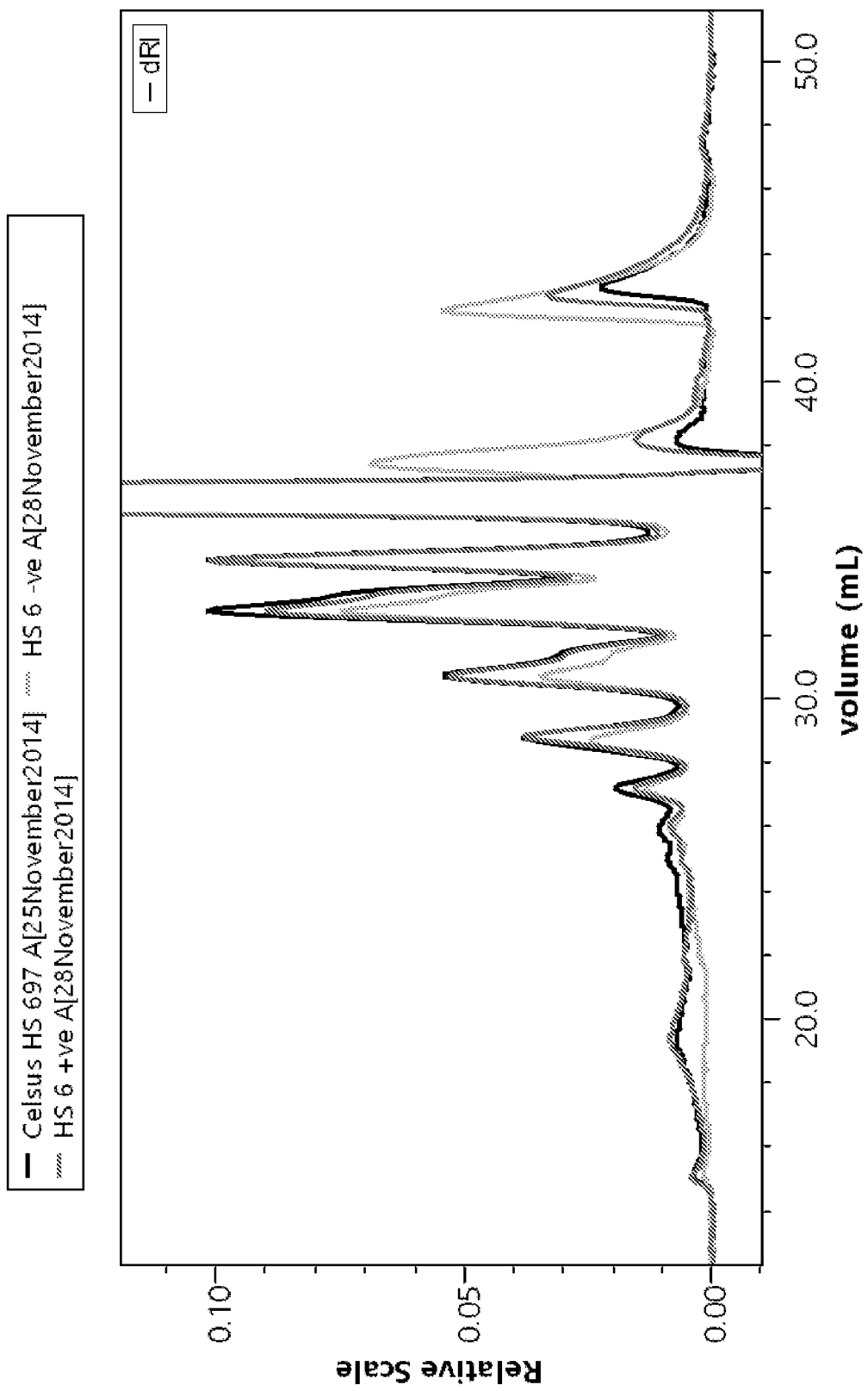
FIG. 25. HPLC-SEC-RI chromatograms of heparin lyase digests of HS6+, HS6− and Celsus HS.

The four late eluting signals correspond to the trisulfated disaccharides (28.8 mL), disulfated disaccharides (30.7 mL), mono- and un-sulfated disaccharides (32.8 mL) and sucrose (34.3 mL; from the enzyme solution), respectively (see FIG. 25). The large signal at approximately 36.3 mL is from buffer salts. Larger oligosaccharides and material elute before approximately 28 mL. The peak eluting at approximately 42-43 mL is NaCl.

For Celsus HS 10697 (starting material) the disaccharides and >dp2 material accounted for approximately 75 µg of the 100 µg injected onto the columns. For the HS-6 samples this value was lower (~67 µg for HS-6 +ve and between 48-58 µg for HS-6 −ve). This reflects the increased NaCl contents of the HS-6 samples compared to Celsus HS 697. There was also a reasonably large unidentified peak (~37 mL) present in the HS-6 −ve samples.

Disaccharide Compositional Analysis by HPLC

Twelve disaccharide standards, derived from the digestion of high-grade porcine heparin by bacterial heparinases, were purchased from Iduron Ltd, Manchester, UK. A stock solution of each disaccharide standard was prepared by dissolving the disaccharide in water (1 mg/mL).

To determine the calibration curves for the disaccharide standards, a standard mix containing 20 µg/mL of each of the disaccharides was prepared from the stock solutions. From this twelve disaccharide standard mix a dilution series containing 20, 10, 5, 2.5, 1.25, 0.625 and 0.3125 µg/mL of each disaccharide was prepared.

The HS digests (2 mg/mL) were diluted with water to give 100 µg/mL solutions and then filtered (hydrophilic PTFE disposable syringe filter units, 0.2 µm, 13 mm, Advantec). The HPLC separation conditions were based on those of Skidmore et al. (2010). The analyses were performed on an Agilent 1260 Infinity liquid chromatography system (Agilent Technologies) with an Agilent 1260 MWD VL detector monitored at 232 nm. HS-derived disaccharides were separated on a ProPac™ PA1 column (Thermo Scientific, 4 mm×250 mm) with a guard column. Gradient elution was performed using a binary solvent system. Eluent A was water at pH 3.5 (adjusted using HCl), and eluent B was 2 M NaCl at pH 3.5 (adjusted with HCl). The gradient program was as follows: 100% A from 0-1 min, then 0-35% B from 1-32 min, then 35-65% B from 32-47 min, then 100% B from 47-57 min, then 100% A from 57-60 min. The injection volume was 50 µL. The column was eluted at a flow rate of 1.0 mL/min and maintained at 40° C.

Disaccharides present in the HS digests were identified from their elution times by comparison with the elution times of the disaccharides in the twelve disaccharide standard mixes. A dilution series of the twelve disaccharide standard mix was run with the digested HS samples. The detector response was linear for all of the disaccharide standards at all of the concentrations tested. These linear calibration curves were used to calculate the proportions of the various disaccharides present in the digests.

Figure 28:
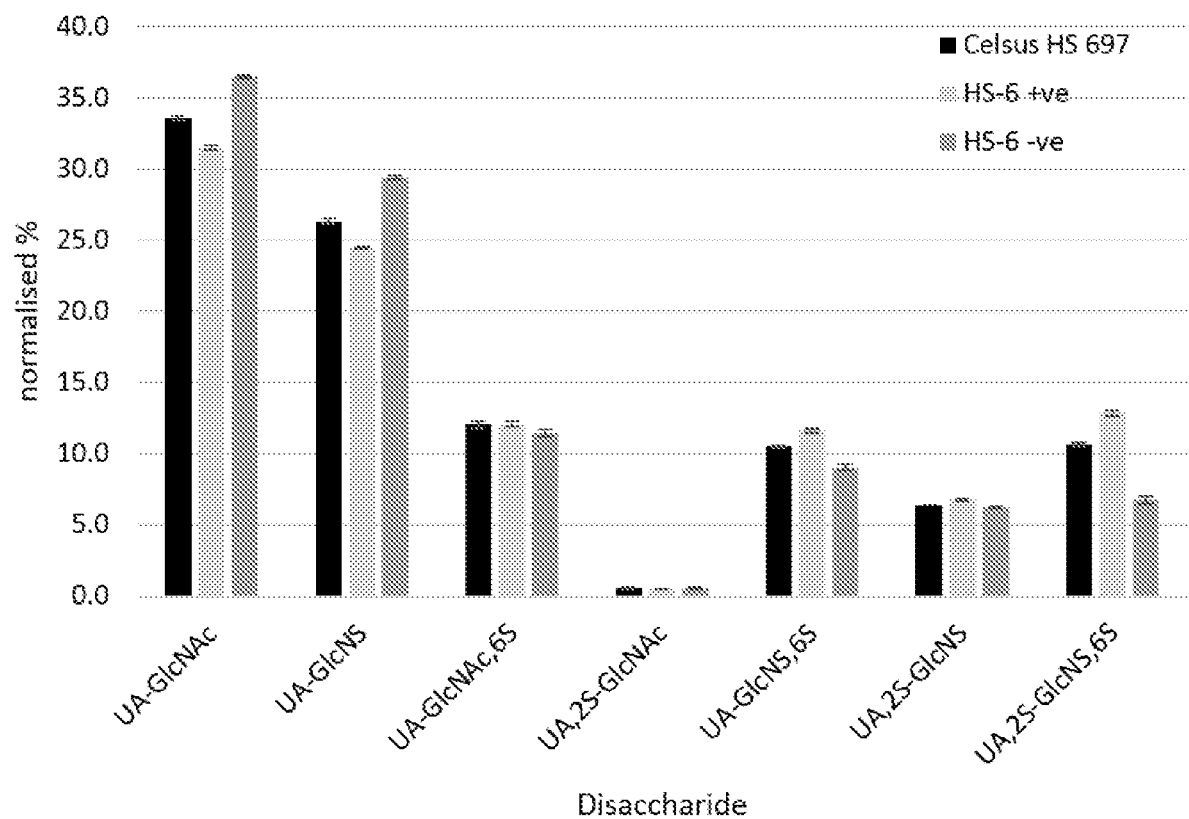
FIG. 28. Chart showing disaccharide composition of HS-6 samples (SAX-HPLC of heparan lyase digests). UV SAX HPLC analysis of the disaccharide composition of heparin lyase digests of heparin sulphate preparations: Celsus HS, HS6+, HS6−.

The HS samples (Celsus HS 10697, HS6 +ve and HS6 −ve) were all digested in duplicate. The duplicate digests of all the samples were injected twice in the HPLC (total of four analyses for each sample). The disaccharide compositions (normalised % disaccharides) determined from each HPLC run are shown in FIG. 27, together with the mean averages. FIG. 28 shows the mean average normalised percentage of each disaccharide in each of the digests. The error intervals were determined using student's t-distribution with confidence limits set at 95.

The proportions of the seven disaccharides in the Celsus HS digests were similar to those found in previous analyses of Celsus HS 10697. The predominant disaccharides were ΔUA-GlcNAc and ΔUA-GlcNS, with smaller proportions of ΔUA-GlcNAc,6S, ΔUA-GlcNS,6S and ΔUA,2S-GlcNS,6S, a small proportion of ΔUA,2S-GlcNS and trace amounts of ΔUA,2S-GlcNAc.

HS-6 has slightly less ΔUA-GlcNAc and ΔUA-GlcNS than Celsus HS 10697 and is slightly enriched in ΔUA-GlcNS,6S and ΔUA,2S-GlcNS,6S, though the differences are only ~1-2%. The non-retained HS-6 contains more ΔUA-GlcNAc and ΔUA-GlcNS than HS-6 and Celsus HS 10697 and less ΔUA-GlcNS,6S and ΔUA,2S-GlcNS,6S.

Example 7: HS6+ Binds to PDGF-BB

GAG Protocol:
1. GAG binding plate (Iduron) was coated with 200 μL/well of 5 μg/ml HS6+ and HS6− fractions prepared in Standard Assay Buffer (SAB, 100 mM NaCl, 50 mM Sodium Acetate, 0.2% (v/v) Tween-20, pH 7.2) overnight. Plates are protected from light at every incubation step.
2. Plates were washed thrice with SAB.
3. Add 250 μL/well of 0.4% (w/v) gelatin blocking solution and incubate at 37° C. for 1 hour.
4. Plates were washed thrice with SAB.
5. Add 200 μL/well of 125, 250 and 500 ng/mL PDGF-BB (R&D) prepared in blocking solution and incubate at 37° C. for 2 hour.
6. Plates were washed thrice with SAB.
7. Add 200 μL/well of 250 ng/mL biotinylated anti-PDGF-BB antibody (R&D) prepared in blocking solution and incubate at 37° C. for 1 hour.
8. Plates were washed thrice with SAB.
9. Add 200 μL/well of 220 ng/mL ExtrAvidin prepared in blocking solution and incubate at 37° C. for 30 minutes.
10. Plates were washed thrice with SAB.
11. Add 200 μL/well of Development Reagent Sigma-FAST p-Nitrophenyl phosphate prepared in distilled water and incubate at room temperature for 40 minutes.
12. Read plate at 405 nm within one hour.

Figure 11:
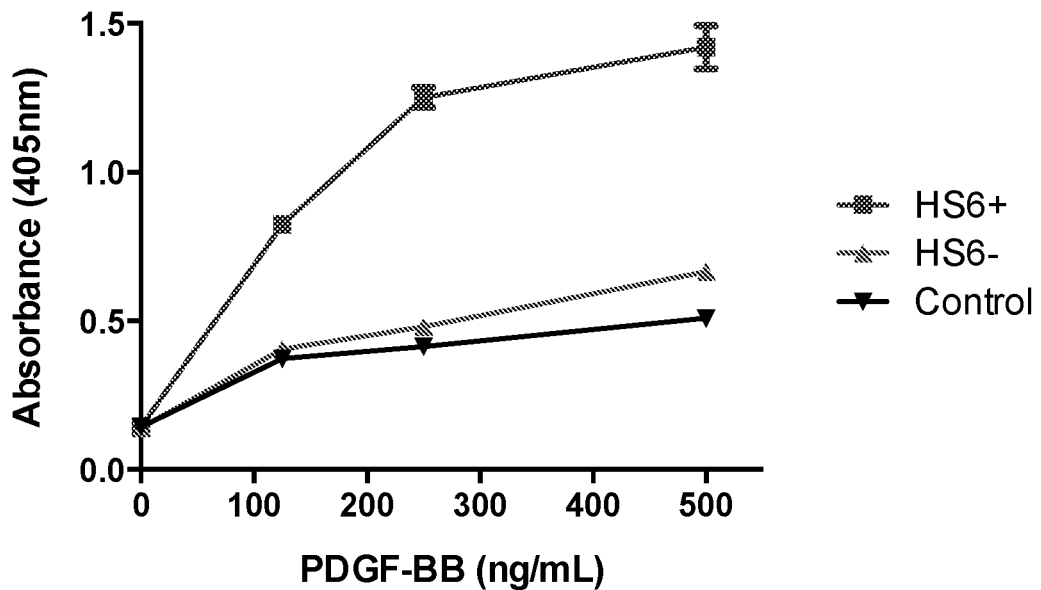
FIG. 11. Chart showing PDGF-BB binding to HS fractions. HS6+ binds to PDGF-BB.

Results:
HS6+ selectively binds to PDGF-BB compared to HS6− (FIG. 11).

Example 8: HS6+ Also Interacts with Other Growth Factors

Figure 12A:
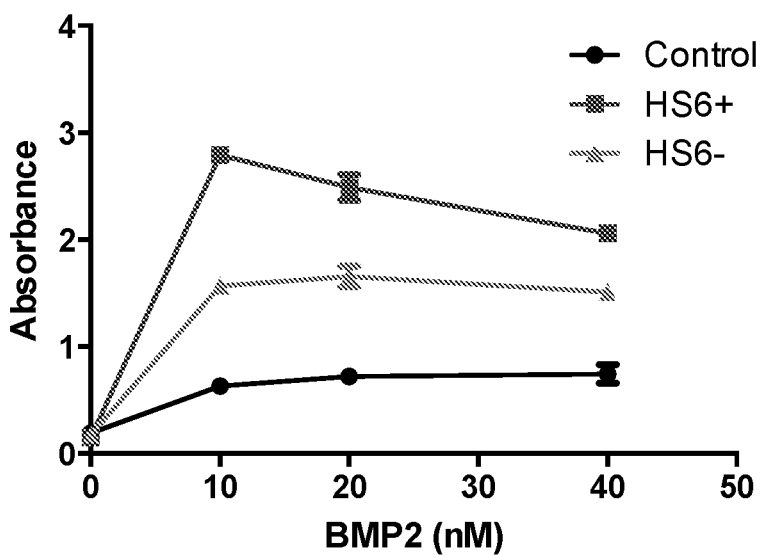
FIG. 12. Charts showing HS6+ interaction with growth factors. (A) Interaction with BMP-2, (B) Interaction with FGF2, (C) Interaction with VEGF-165.
Figure 12B:
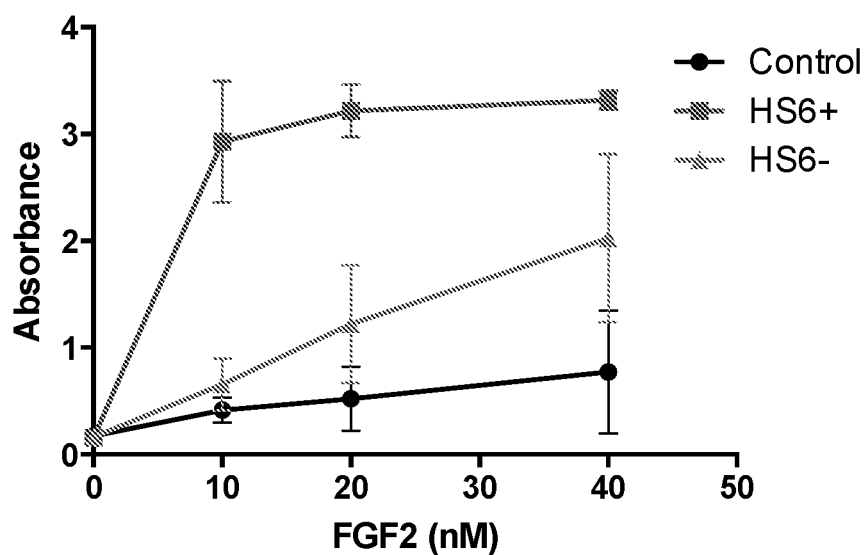
Figure 12C:
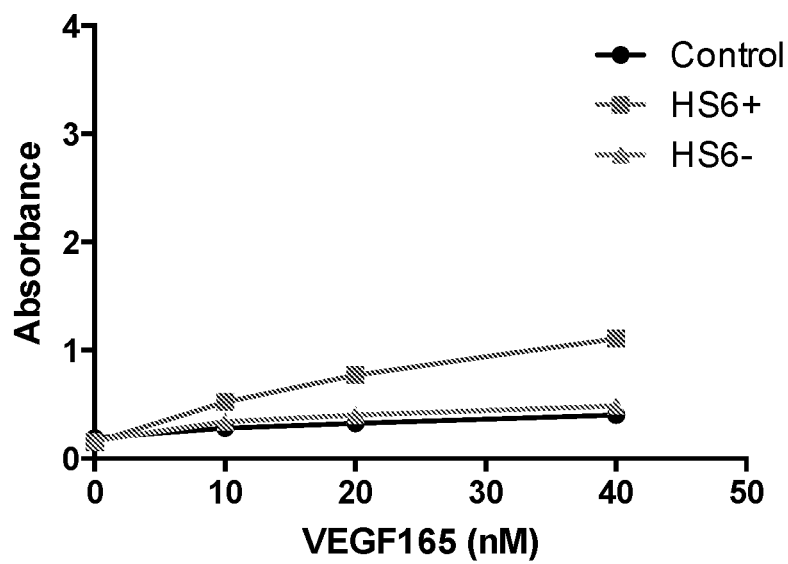

Whilst HS6+ is isolated based on affinity for a peptide sequence contained within the amino acid sequence of PDGF-BB, HS6+ is also able to interact with other pro-healing factors present in wound sites such as BMP-2 and FGF-2, and displays some association with VEGF165 (FIG. 12). This binding may simply be based on the increased charge density of HS6+ and not related to sequence information. What is interesting to note is that HS6+ binds with high affinity to PDGF-BB whilst the flow through fraction HS6− does not bind much PDGF-BB, yet the HS6− fraction still contains chains with affinity for BMP-2, FGF-2 but not VEGF165 (FIG. 12). Thus HS6+ may generate its affect through a range of factors making it particularly useful for wound healing.

Example 9: PDGF-BB and HS6+ Dose Dependent Increase in HDF Proliferation

Proliferation Protocol:
1. Thaw human dermal fibroblast (HDF, Cascade Biologics) into a T75 in maintenance medium at 5×10³ cells/cm² (α-MEM, 10% FCS, P/S) at 37° C. 5% CO² humidified incubator.
2. At 70-80% confluence, wash cells in PBS twice, add 1 ml of 0.125% trypsin and incubate for 3 mins. Tap the dish and stop the trypsin by adding 5 ml of medium. Centrifuge cells down at 180 g for 7 mins.
3. Count total number of cells.
4. Seed cells at 500 μl of 3000 cells/cm² cell suspension per well and place the plates into the incubator for 24 hrs.
5. Change media to α-MEM, 1% FCS, P/S media for 24 hrs.
6. Treat cells with PDGF-BB and HS fractions.
7. After 72 hrs, wash cells with PBS and add 100 ul of trypsin, incubate for 3 mins.
8. Add 100 ul of Guava Viacount dye mastermix into each well of trypsinize cells.
9. Transfer total volume of 200 ul of cells per well into a 96 well Guava plate.

Figure 13A:
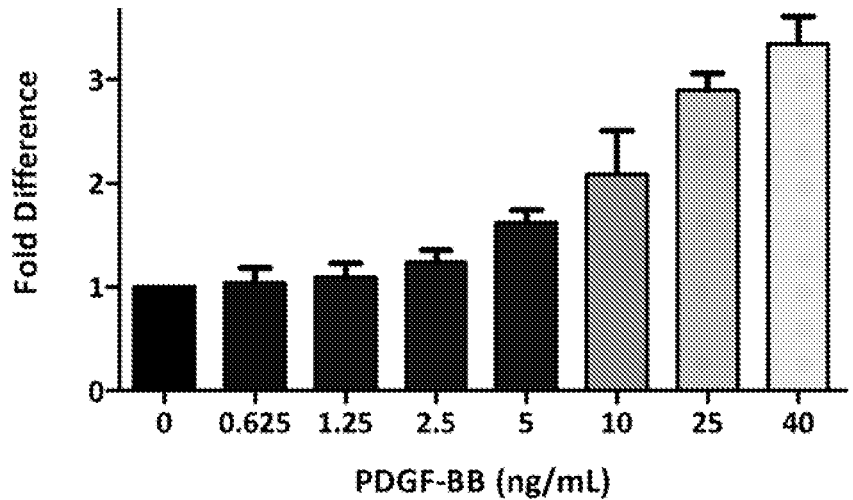
FIG. 13. Charts showing PDGF-BB and HS6+ dose dependently increase HDF proliferation. (A) PDGF-BB dosing, (B) HS6+ dosing, (C) PDGF-BB and HS6 dosing.
Figure 13B:
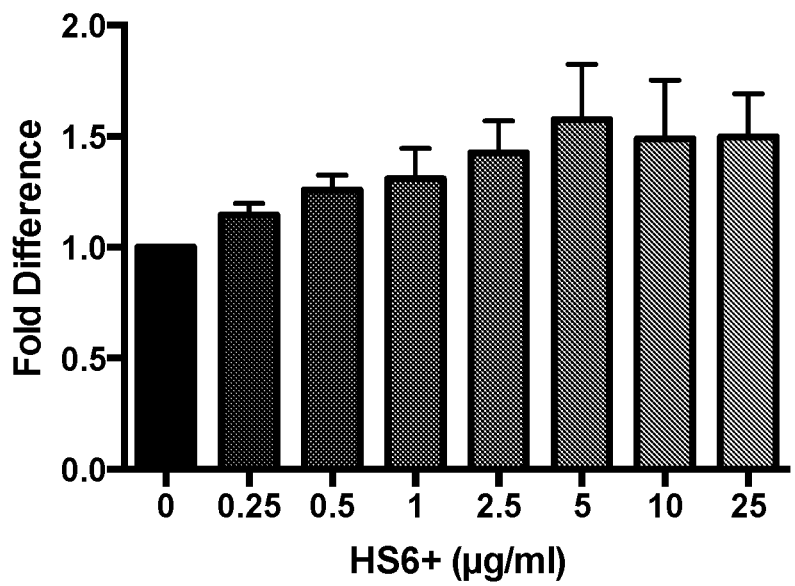
Figure 13C:
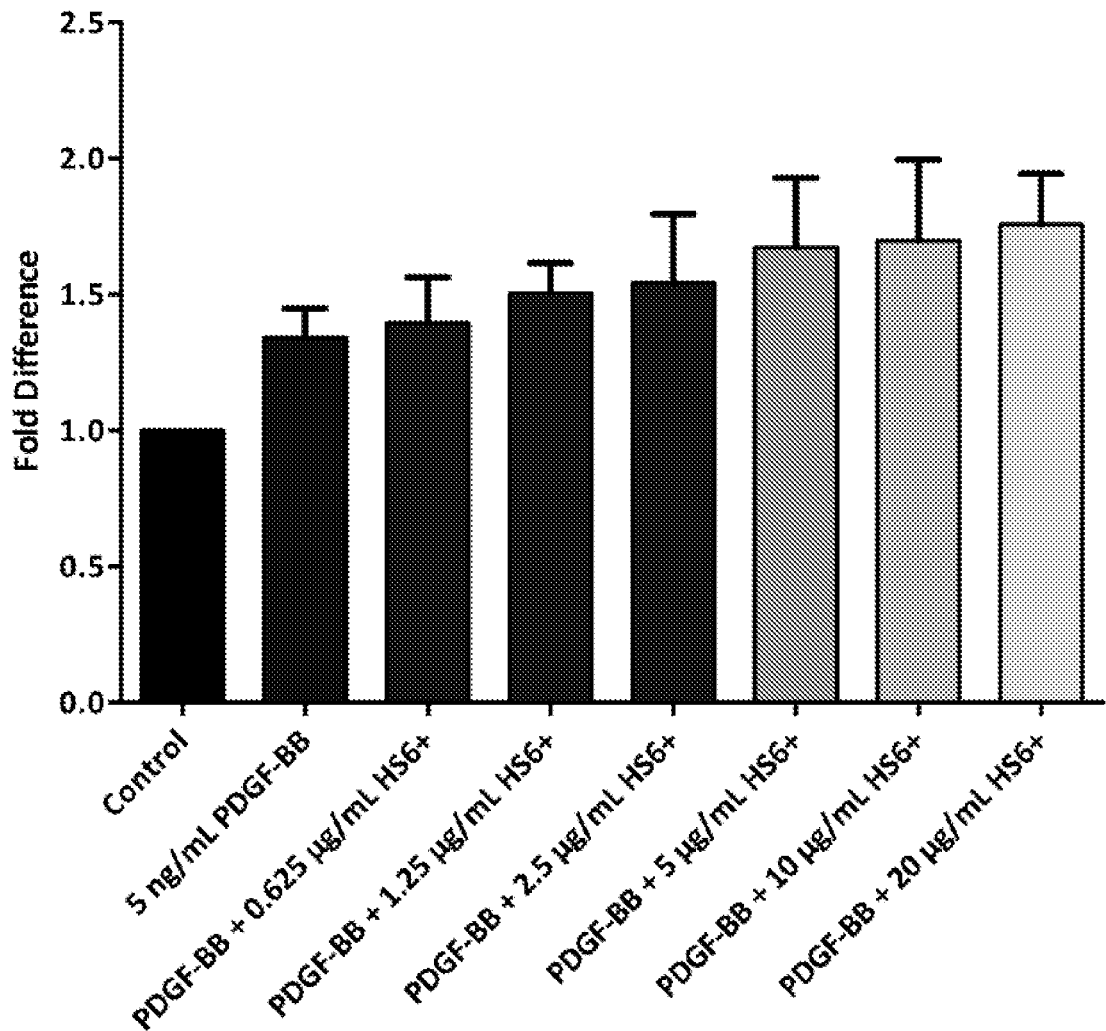

Results:
There is a PDGF-BB dose dependent increase in proliferation of HDF (FIG. 13). 10 ng/mL was the optimal concentration for proliferation.

Higher concentration of PDGF-BB results in a decreased viability of HDF.

A sub-optimal PDGF-BB concentration at 5 ng/mL was used for future proliferation experiments.

Similarly, an increase in HS6+ concentration results in a gradual increase in proliferation. Proliferation plateaus with the addition of 20 μg/mL HS6+ and 5 ng/mL.

20 μg/mL was selected as the HS6+ concentration to be used to compare between the different fractions.

Example 10: PDGF-BB and HS6+ Increases HDF Proliferation

The proliferation protocol described in Example 9 was used.

Figure 14:
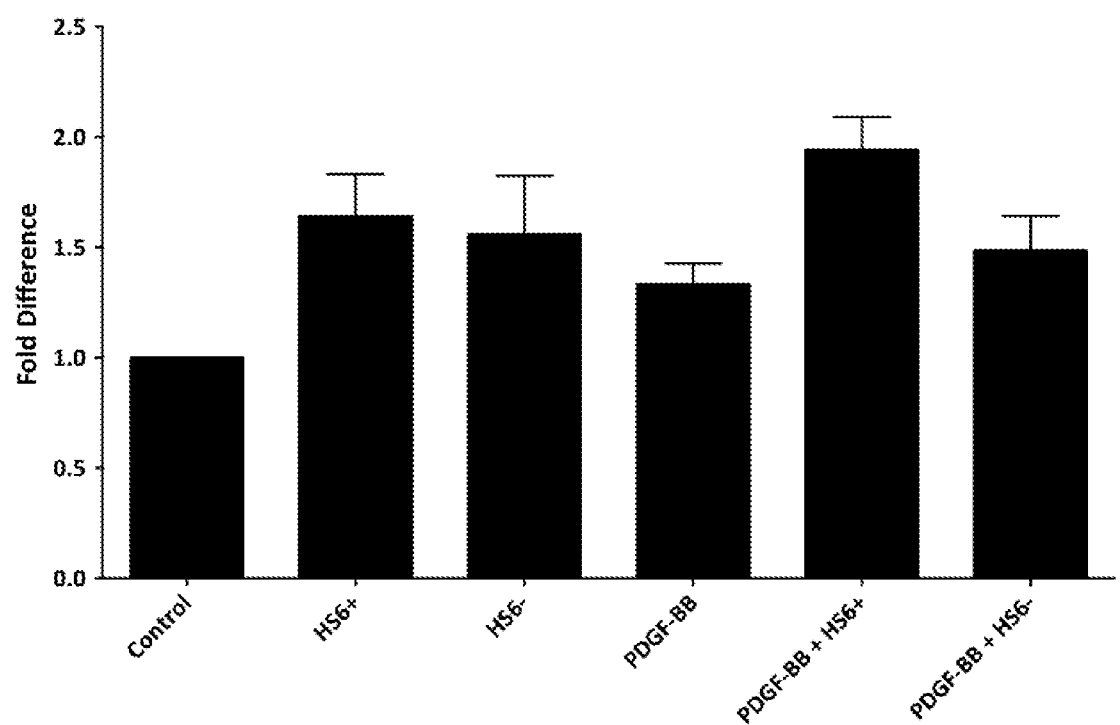
FIG. 14. Chart showing HDF Proliferation with 5 ng/mL PDGF-BB+20 μg/mL HS. PDGF-BB and HS6+ increase HDF proliferation.

Results are for 72 h proliferation:

20 μg/mL HS6+ and HS6− alone is able to induce proliferation better than 5 ng/mL PDGF-BB (FIG. 14).

In combination, 20 μg/mL HS6+ with 5 ng/mL PDGF-BB increases HDF proliferation compared to HS6− with PDGF-BB (FIG. 14).

Not shown in FIG. 14 is the different morphology of HDF treated with HS6+ and PDGF-BB. Cells look spindle shaped and may be stained for myofibroblast marker such as alpha smooth muscle actin.

The HS6− fraction is able to also enhance the growth of HDFs presumably because it can bind and activate FGF-2 (FIG. 12). The fact that HS6− when combined with PDGF does not produce an additive affect, suggests there is little interaction between these two factors, consistent with FIG. 11.

Example 11: PDGF-BB Induces HDF Migration

Migration Protocol:
1. Seed 10,000 HDF per well in maintenance media, into a 96 well ImageLock plate.
2. After 24 hrs, change media to 1% α-MEM
3. Once cells are confluent, scratch the surface using the wound maker and wash once with PBS.
4. Add 100 μl of treatment media into each well and place plate into IncuCyte and run for 40 hours.
5. Program is set up to take photo every 2 hours.

Results:
Rate of wound closure increases up to 10 ng/mL PDGF-BB (FIG. 15).

Figure 15:
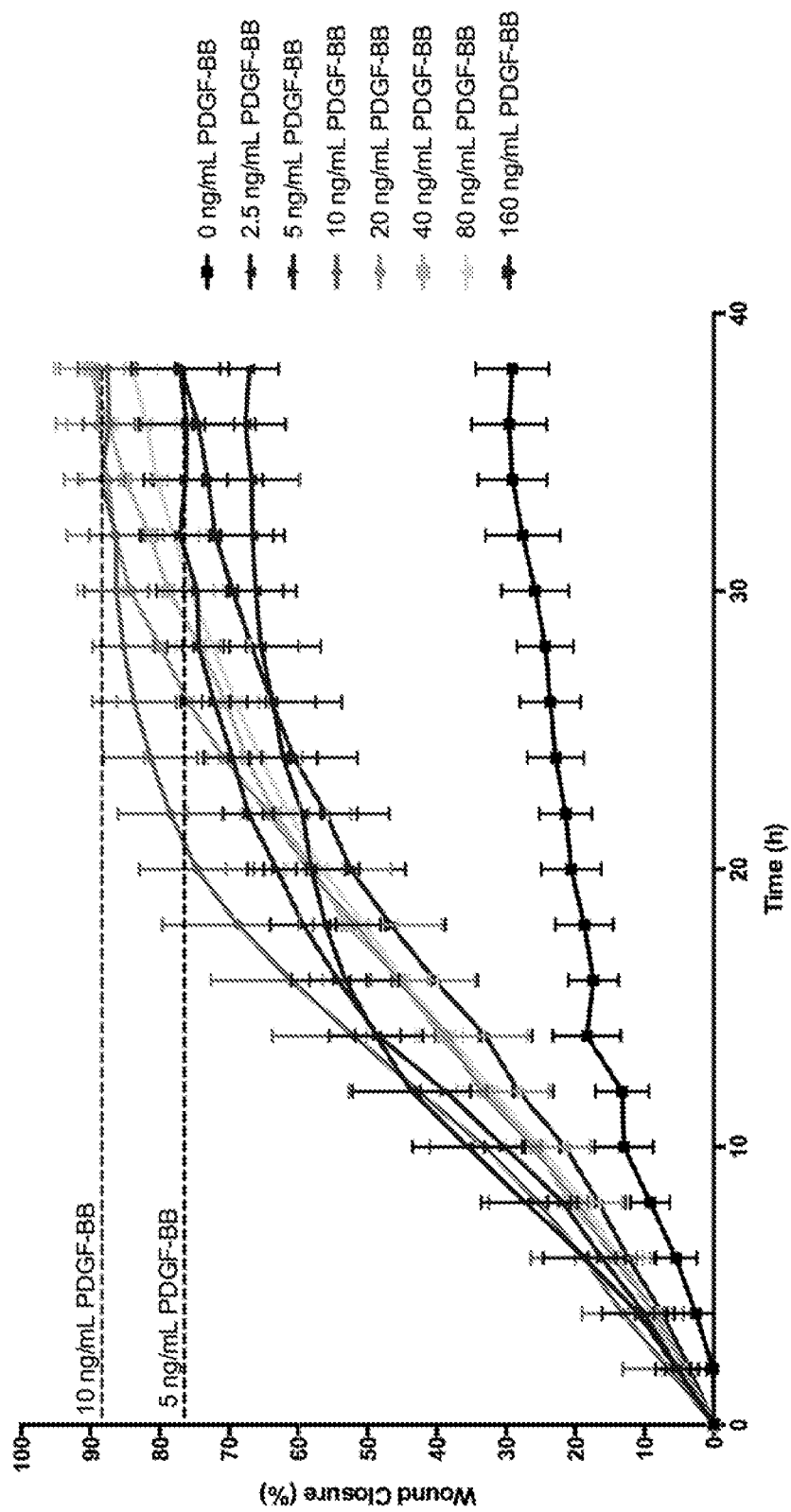
FIG. 15. Chart showing effect of PDGF-BB dosing in HDF migration studies in a Scratch Assay. PDGF-BB induces HDF migration.

The addition of more than 10 ng/mL PDGF-BB does not speed up the rate of closure (FIG. 15).

Sub optimal concentration of 5 ng/mL PDGF-BB was selected for use in future migration studies.

Example 12: HS6+ Dosing for Migration Studies

The migration protocol from Example 11 was followed using a range of HS6+ doses (20 μg/mL, 40 μg/mL, 60 μg/mL) with 5 ng/ml PDGF-BB.

Figure 16:
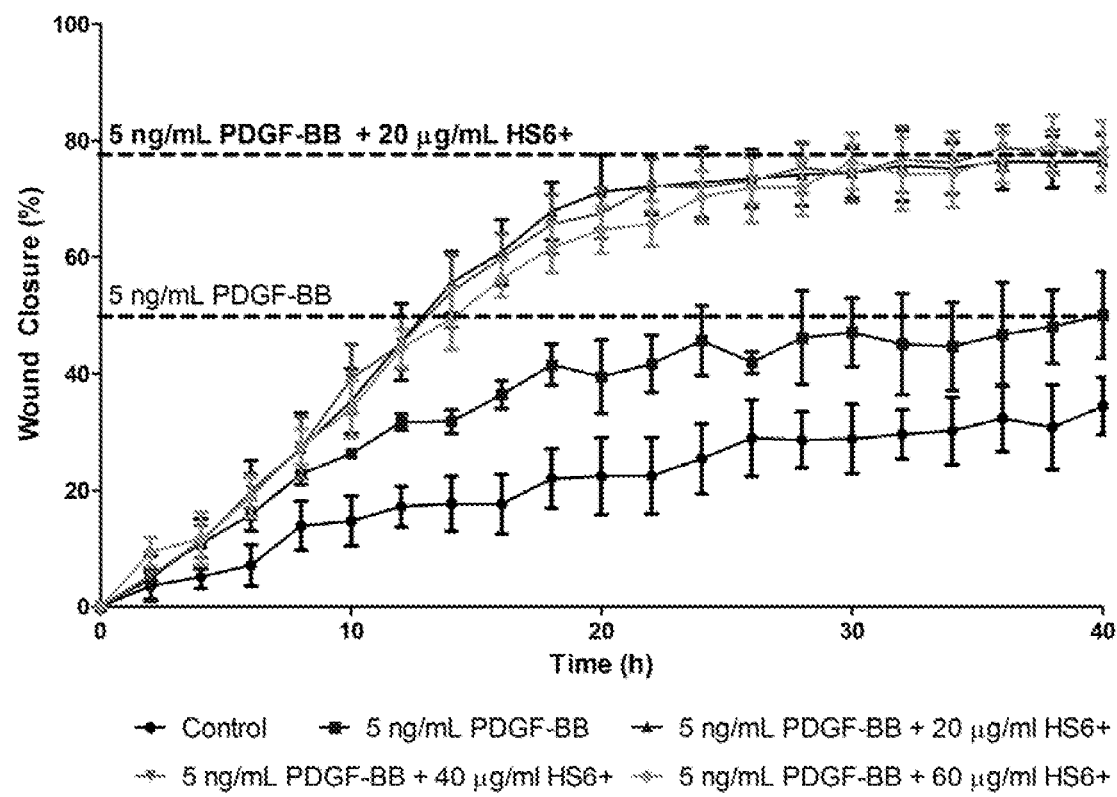
FIG. 16. Chart showing effect of HS6+ dosing in HDF migration studies in a Scratch Assay.

Results:
Addition of 20 ug/ml of HS6+ significantly increases the rate of wound closure compared to 5 ng/ml PDGF-BB alone. Addition of more than 20 ug/ml HS6+ does not further speed up rate of wound closure (FIG. 16).

Figure 17:
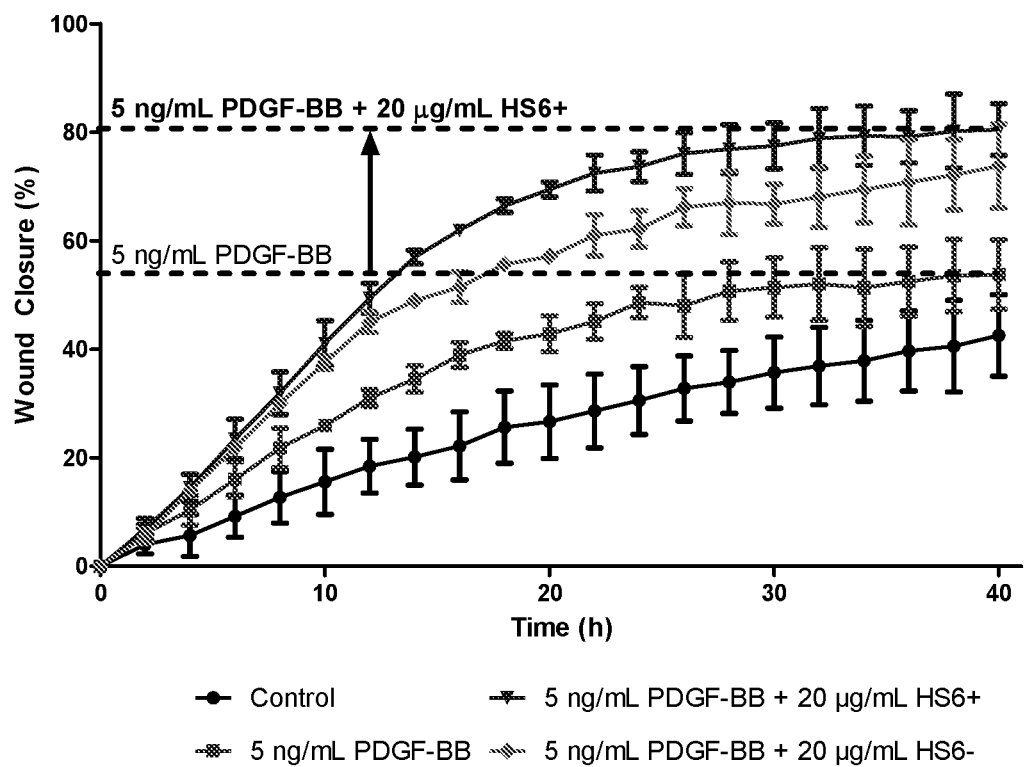
FIG. 17. Chart showing PDGF-BB and HS6+ increase migration of HDFs in a Scratch Assay. 5 ng/mL PDGF-BB+20 μg/mL HS fractions.

HS6– was better than PDGF-BB alone, but has a lower rate of wound closure compared to HS6+(FIG. 17).

Example 13: HS6+ Increases Phosphor-PDGFRβ in HDFs

Figure 18A:
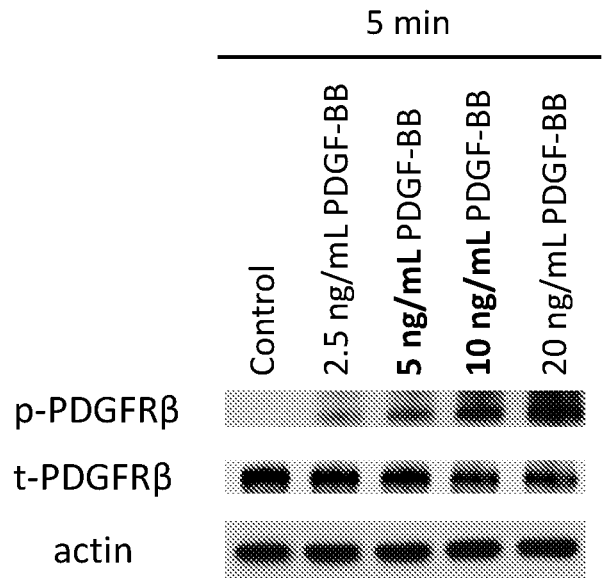
FIG. 18. HS6+ increases phosphor-PDGFRβ in HDFs. (A) Photograph showing PDGFRβ phosphorylation in response to PDGF-BB, (B) Photograph showing PDGFRβ phosphorylation in response to HS6, (C) Chart showing PDGFRβ phosphorylation in HDF in response to PDGF-BB, PDGF-BB+HS6+, PDGF-BB+HS6−.
Figure 18B:
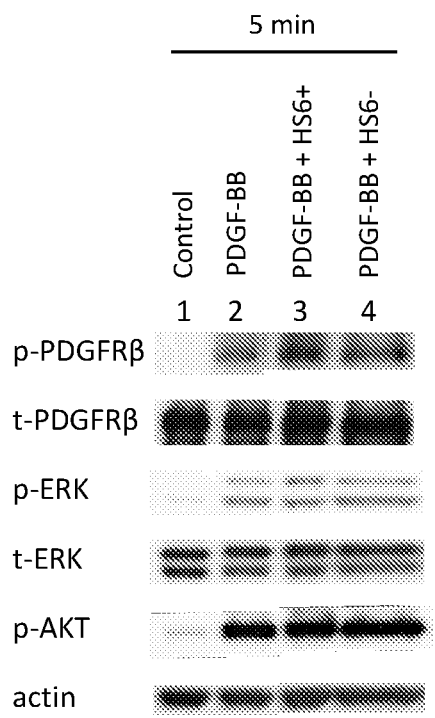
Figure 18C:
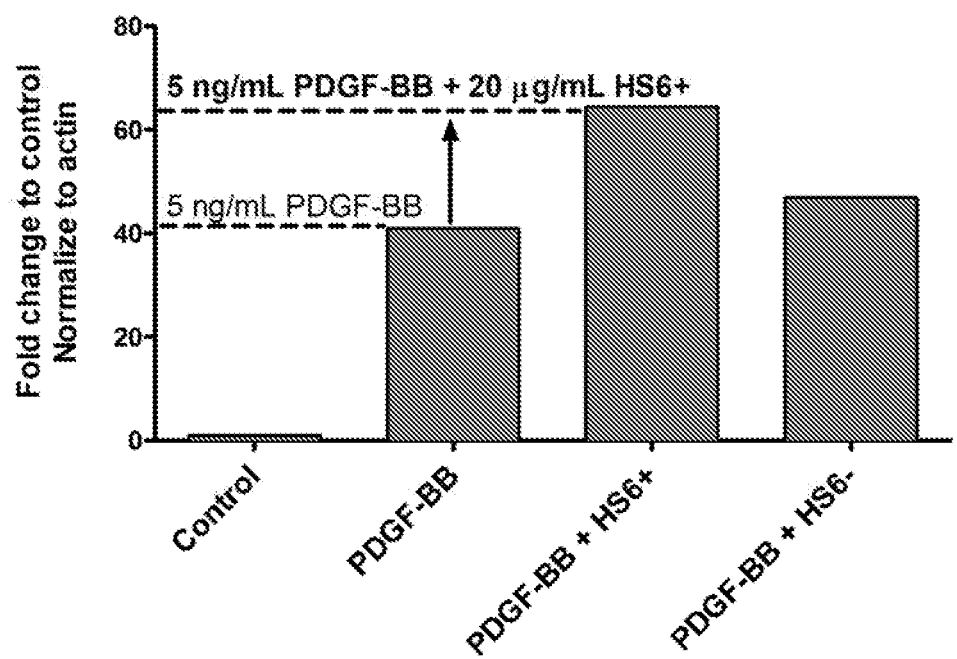
Figure 19:
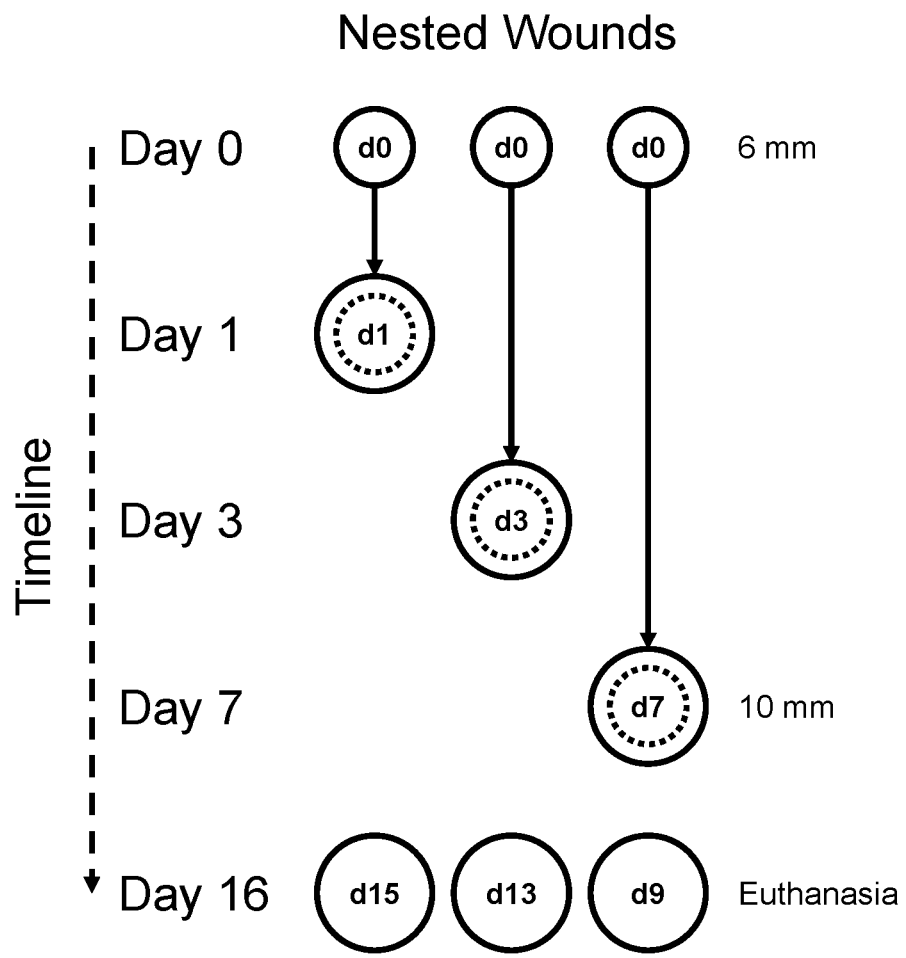
FIG. 19. Representation of nested wounds in pig skin model.

Protocol:
1. Thaw human dermal fibroblast (HDF, Cascade Biologics) into a T75 in maintenance medium at 5×10³ cells/cm² (α-MEM, 10% FCS, P/S) at 37° C. 5% CO₂ humidified incubator.
2. At 70-80% confluence, wash cells in PBS twice, add 1 ml of 0.125% trypsin and incubate for 3 mins. Tap the dish and stop the trypsin by adding 5 ml of medium. Centrifuge cells down at 180 g for 7 mins.
3. Count total number of cells.
4. Seed cells at 10,000 cells/cm² cell suspension per well and place the plates into the incubator for 24 hrs.
5. Change media to α-MEM, 1% FCS, P/S media for 24 hrs.
6. Treat cells with PDGF-BB and HS fractions.
7. Remove old media and wash cells twice with PBS.
8. Add Laemmli (2×) Sigma into each well and scrap cells.
9. Collect samples into labeled eppendorf tubes and denature at 95° C. for 5 mins.
10. Store all samples at –20° C.
11. SDS Page→Transfer→antibody incubation Results:
HS6+ increases phosphor-PDGFRβ in HDFs (FIG. 18).

Example 14: Pick Skin Wound Healing Model

Full thickness excisional wounds were created on the back of five adult micropigs. The back of the anaesthetized pigs was shaved and cleaned with povidone iodine solution. To serve the experimental timepoints at day 1, 3, 7, 9, 13 and 15, nested wounds were created using a 6 and 10 mm biopsy punch. A set of three wounds is required for the entire experimental timepoints. The initial three wounds were made with a 6 mm biopsy punch. At day 1, 3 and 7, each wound is cored out with a 10 mm biopsy punch. By day 16, the 10 mm wounds serve as day 9, 13 and 15 timepoints.

Treatments were initiated by the topical application of 250 μg/cm³ HS compound via 10 mg/ml carboxymethyl cellulose (CMC) (Sigma) gel (n=6), or CMC gel alone (untreated wound) (n=6). 56.5 μL and 157 μL of HS compound was applied respectively into the 6 and 10 mm wounds at day 0 and 1. The wounds were covered with Tegaderm dressing (3M Singapore). All of the wounds were examined and photographed following surgery.

The pigs were euthanized at day 16 and full thickness skin samples of the wounds with surrounding unwounded skin were excised and cut into half. One half was fixed in 10% neutral buffered formalin for histological analysis. Another half was placed into TRIzol (Life Technologies) and frozen at –80° C. for subsequent molecular analysis.

Treatment and dosage groups may be summarised as follows:
Endogenous PDGF-BB
Treatment groups
  Empty
  Carrier: 10 mg/mL carboxymethylcellulose (CMC) gel
  250 μg/cm³ HS6+ in CMC
  250 μg/cm³ HS6– in CMC
HS dosage
  6 mm→14.13 μg in 56.5 μL of CMC gel
  10 mm→39.25 μg in 157 μL of CMC gel
Treat at day 0 and 1

Figure 20:
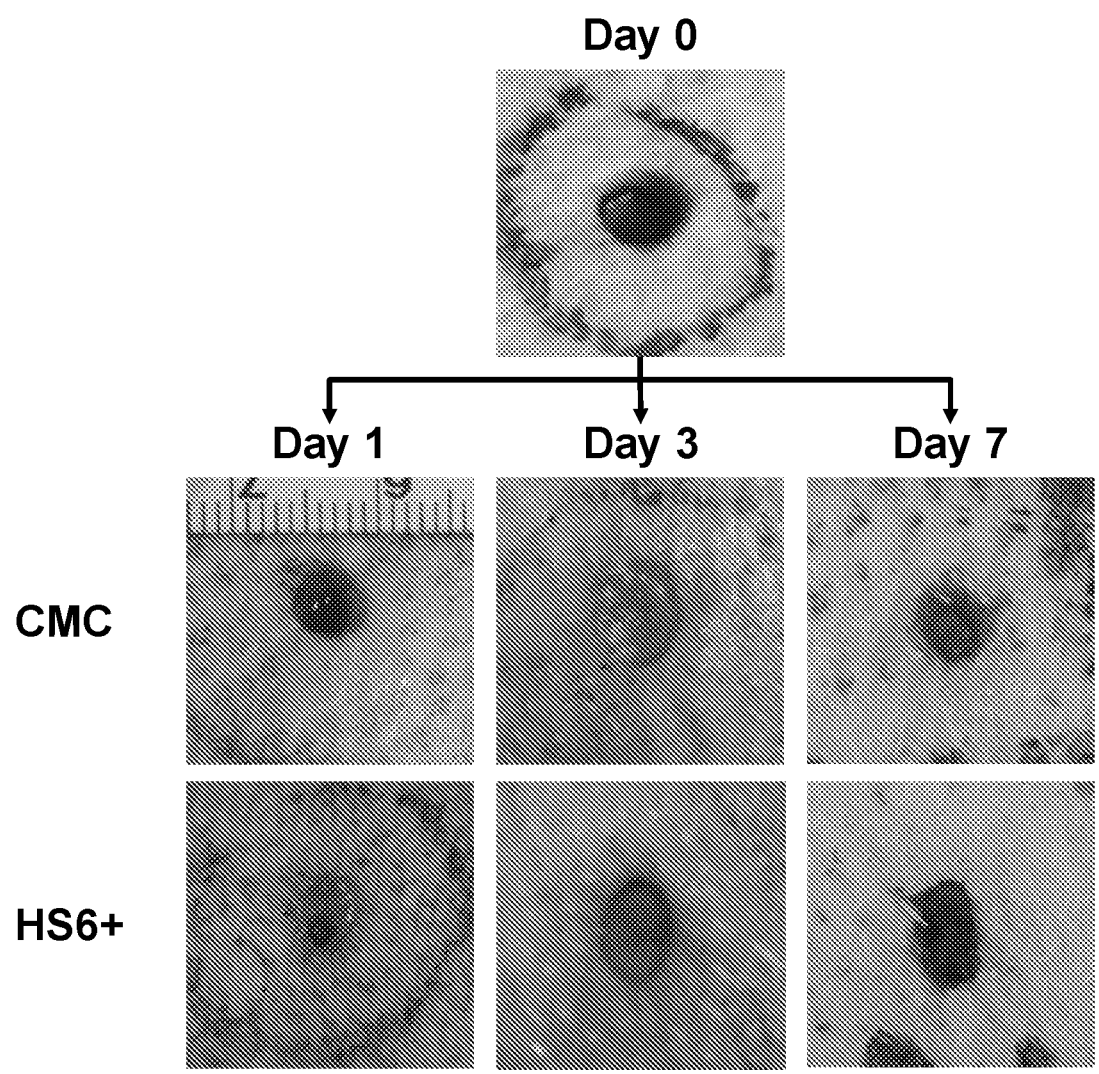
FIG. 20. Photographs showing wound healing of 6 mm wounds at day 1, 3, 7 with CMC or HS6+.
Figure 21:
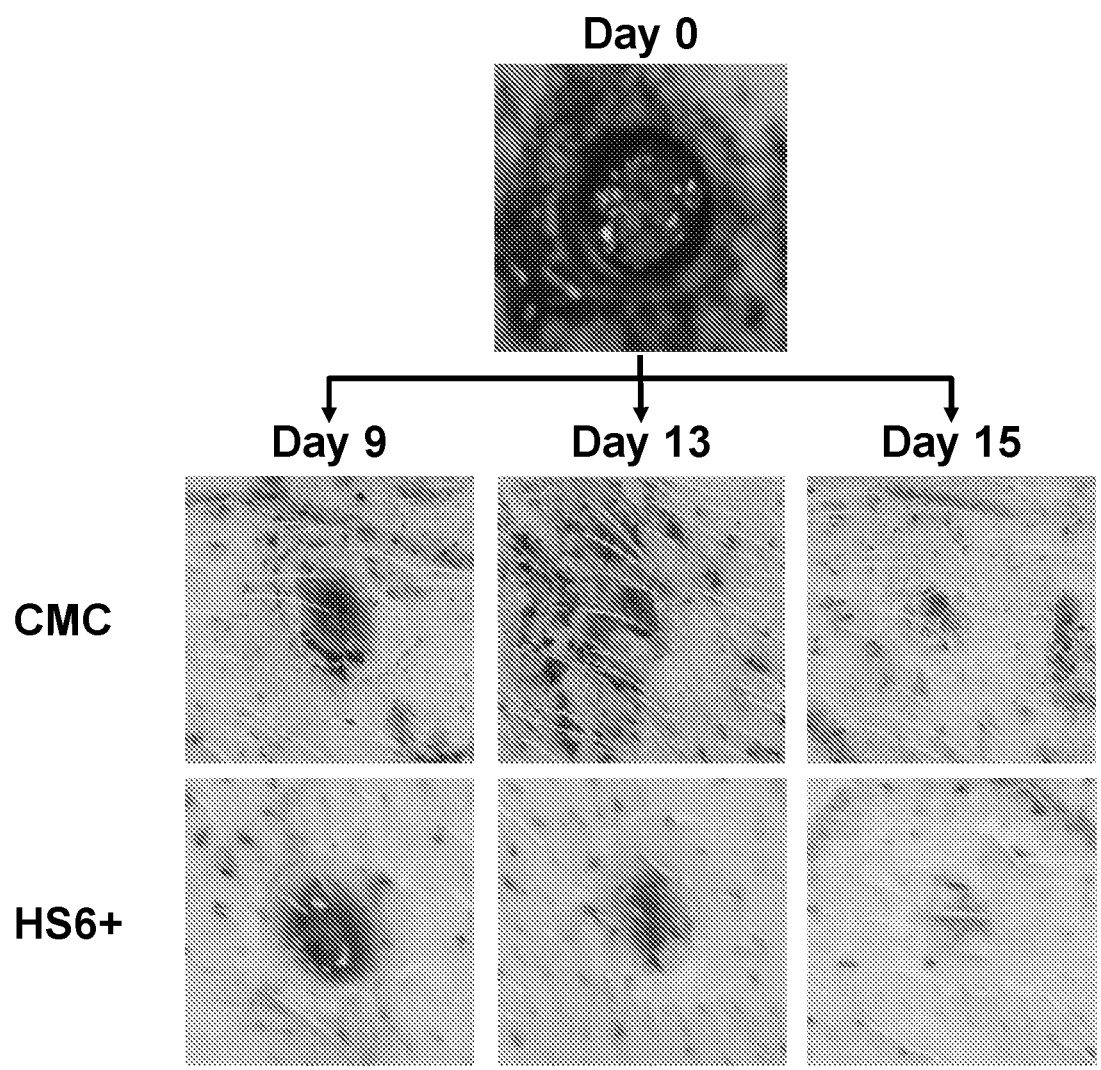
FIG. 21. Photographs showing wound healing of 10 mm wounds at day 9, 13, 15 with CMC or HS6+.

Degree of wound healing is shown in FIGS. 20 and 21. HS6+ treatment group shows accelerated wound healing compared to CMC group.

Figure 22A:
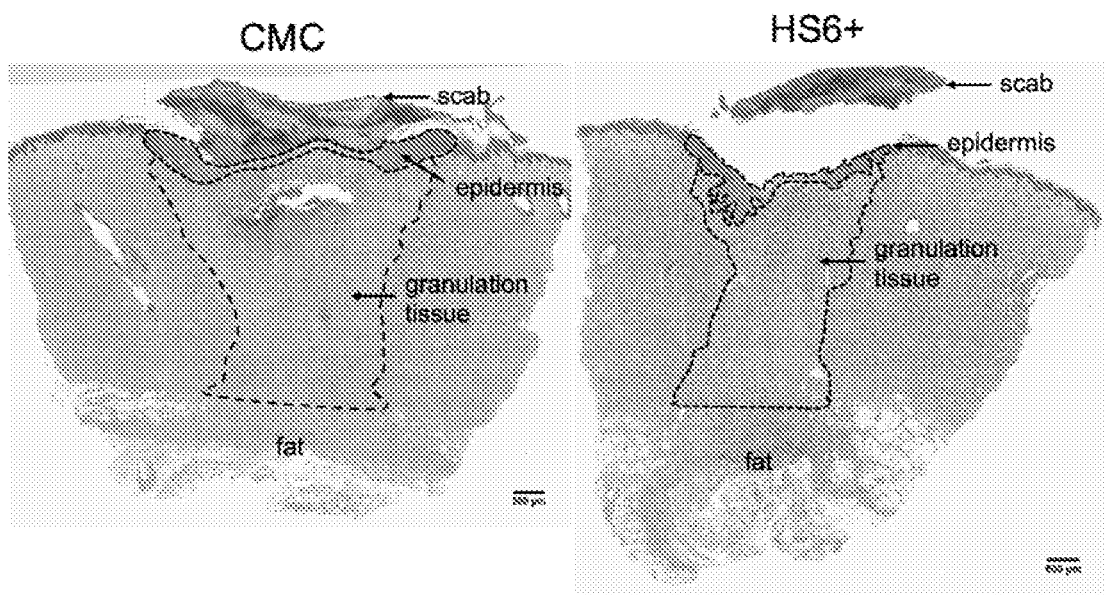
FIG. 22. Differences in hematoxylin and eosin (H&E) staining at day 7. (A) Illustration of H&E staining at day 7 in CMC control and in HS6+ treatment group. (B) Graphical representation of differences in H&E staining, shown as area of granulation tissue at day 7. Each point represents a separate wound treated with either CMC carrier alone or CMC carrier containing HS6+. Line represents median score FIG. 23. Decreased cellular infiltrates with HS6+. (A) Illustration of cellular infiltration following HS6+ treatment. (B) Graphical representation of cellular infiltrates at day 7 in CMC control and HS6+ treatment group. Each point represents a separate wound treated with either CMC carrier alone or CMC carrier containing HS6+. Line represents median score.
Figure 22B:
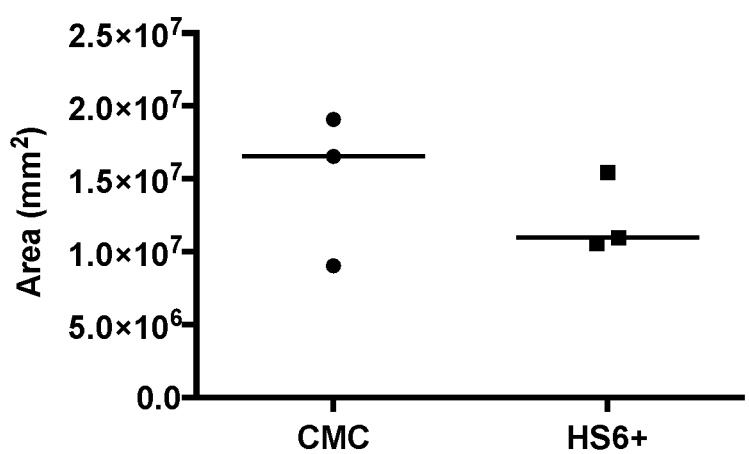
Figure 23A:
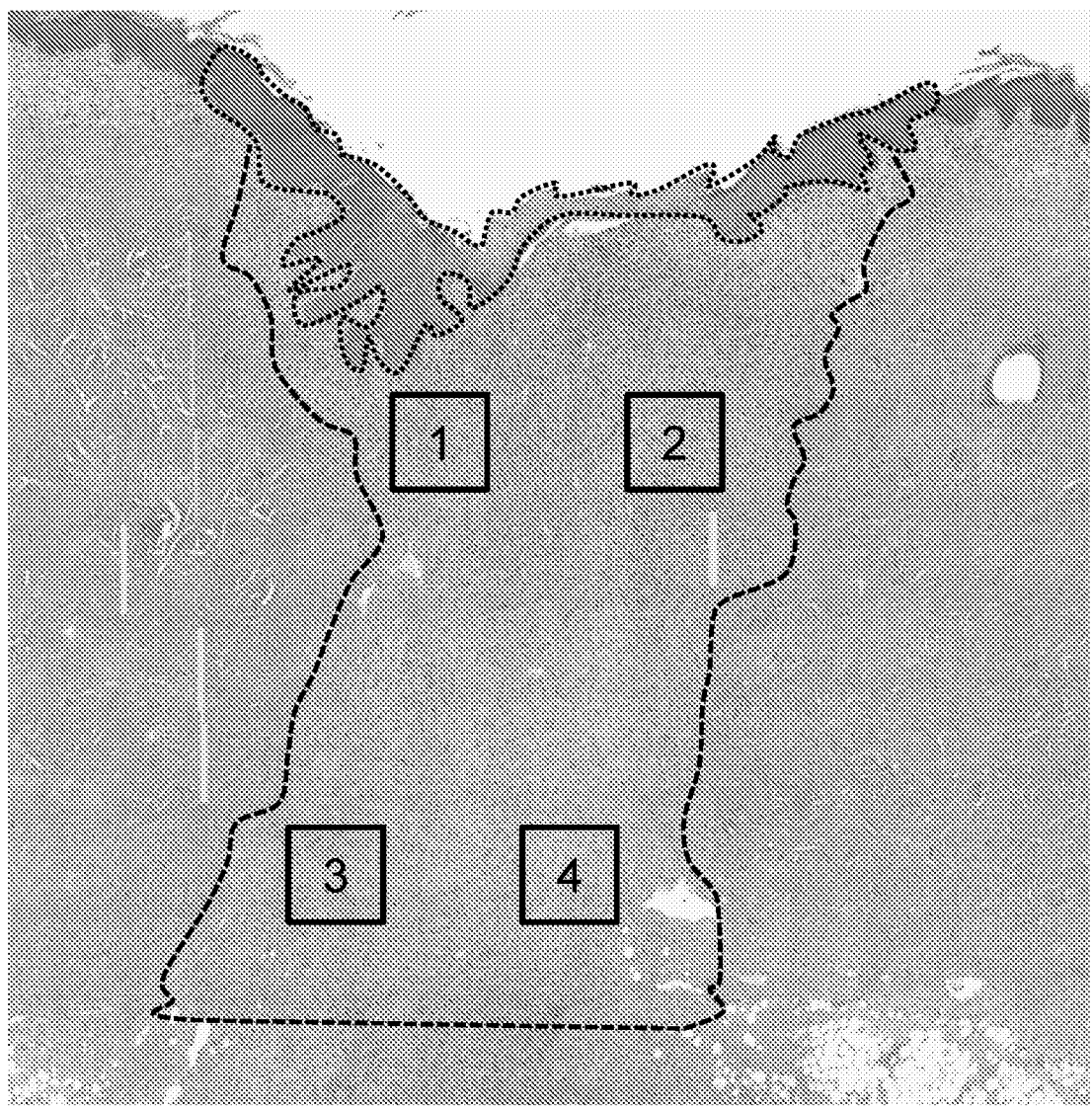
Figure 23B:
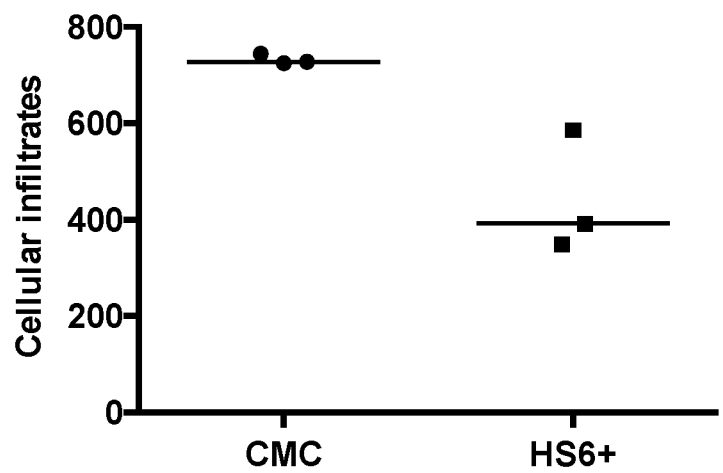
Figure 24A:
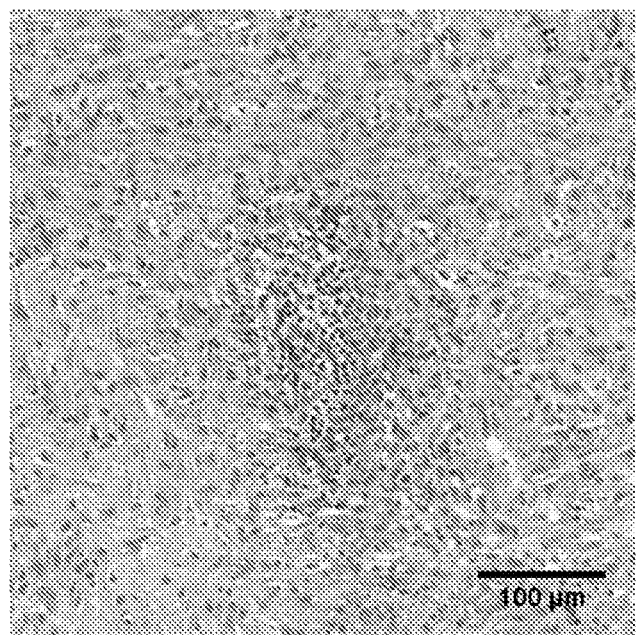
FIG. 24. Photographs showing presence of blood vessels following treatment with (A) CMC control or (B) HS6+.
Figure 24B:
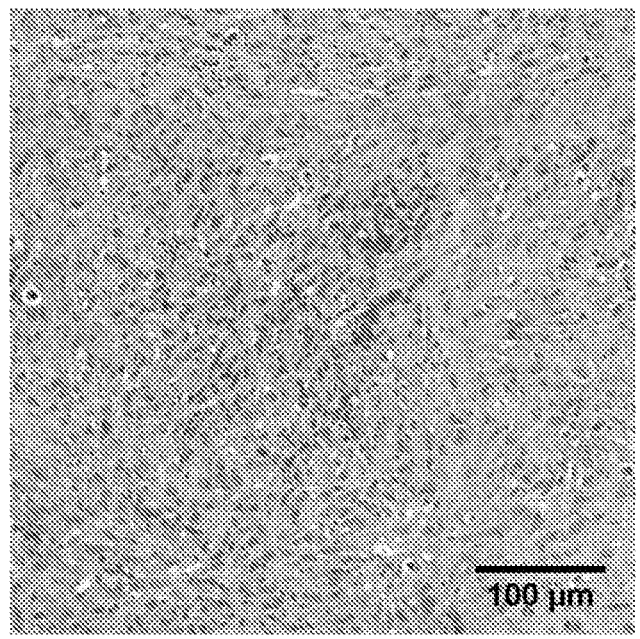

Differences in Hematoxylin and Eosin (H&E) Staining at Day 7:
HS6+ treatment group shows (FIG. 22):
  Advanced epidermis structure
  Contraction of granulation tissue
  Increased matrix deposition
  Formation of blood vessels
  Decreased cellular infiltrates (inflammatory cells)
Decreased Cellular Infiltrates with HS6+
  Numbers of infiltrating leucocytes were counted in four 1 mm zones per wound bed (FIG. 23).
Presence of Blood Vessels with HS6+
  FIG. 24 shows inflammation with carrier alone, and more matrix and blood vessel formation following treatment with HS6+

Summary
Treatment with HS6+ led to complete re-epithelization and formation of granulation tissue at Day 7, contraction of granulation tissue, increased matrix deposition, formation of blood vessels, decreased cellular infiltrates (inflammatory cells).

Example 15: Effects of HS6 on HDF and Keratinocyte Proliferation In Vitro

The effects of HS6 on keratinocytes within the skin epidermis, and human dermal fibroblasts (HDFs) was investigated, because both cell types are important in wound healing.

Figure 29A:
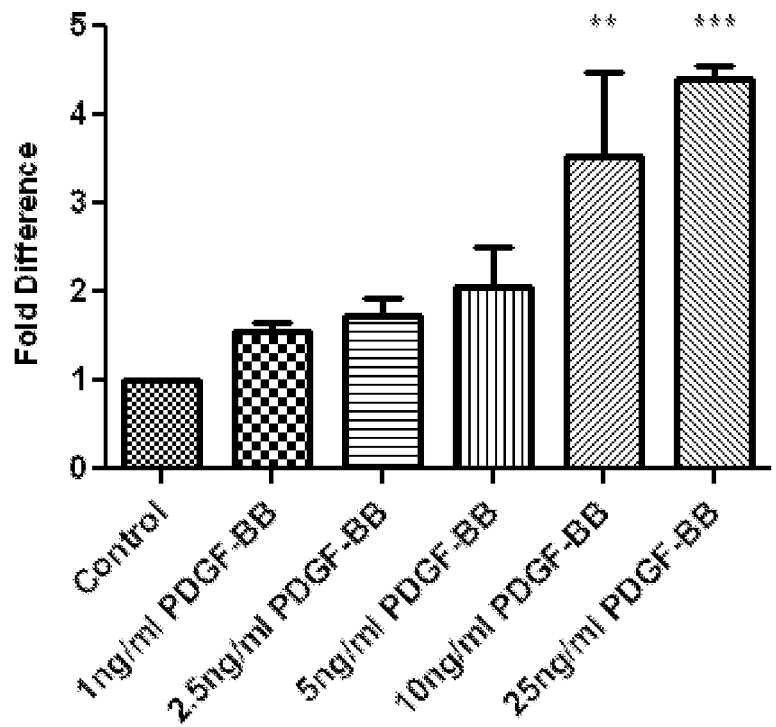
FIG. 29. Charts showing proliferative effect of PDGF-BB and HS6 on human dermal fibroblasts: (A) PDGF-BB (1, 2.5, 5, 10, 25 ng/ml), (B) HS6 (0.25, 0.5, 1, 2.5, 5, 10, 25 μg HS6), (C) 2.5 ng PDGF-BB+HS6 (0, 0.25, 0.5, 1, 2.5, 5, 10, 25 μg).
Figure 29B:
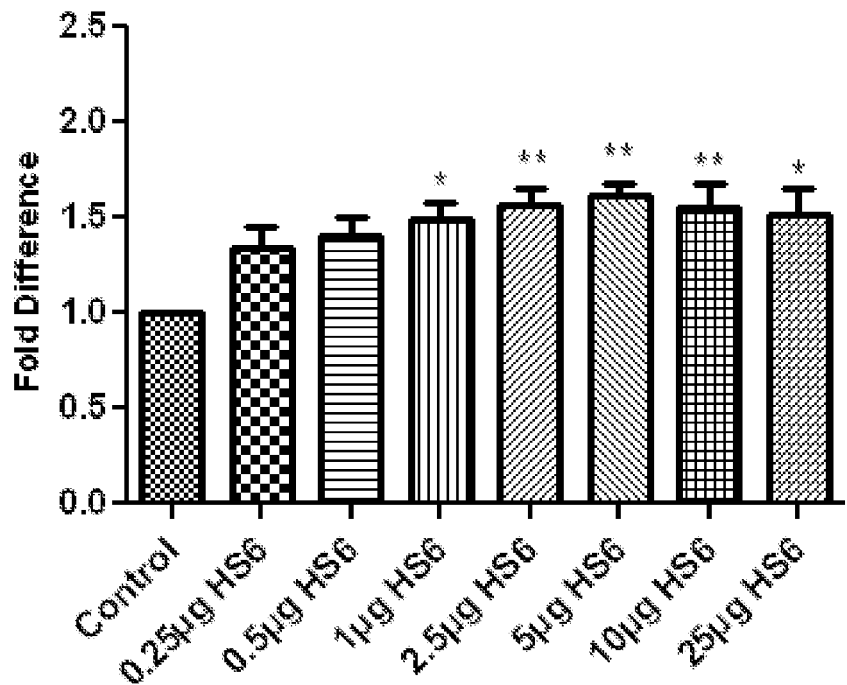
Figure 29C:
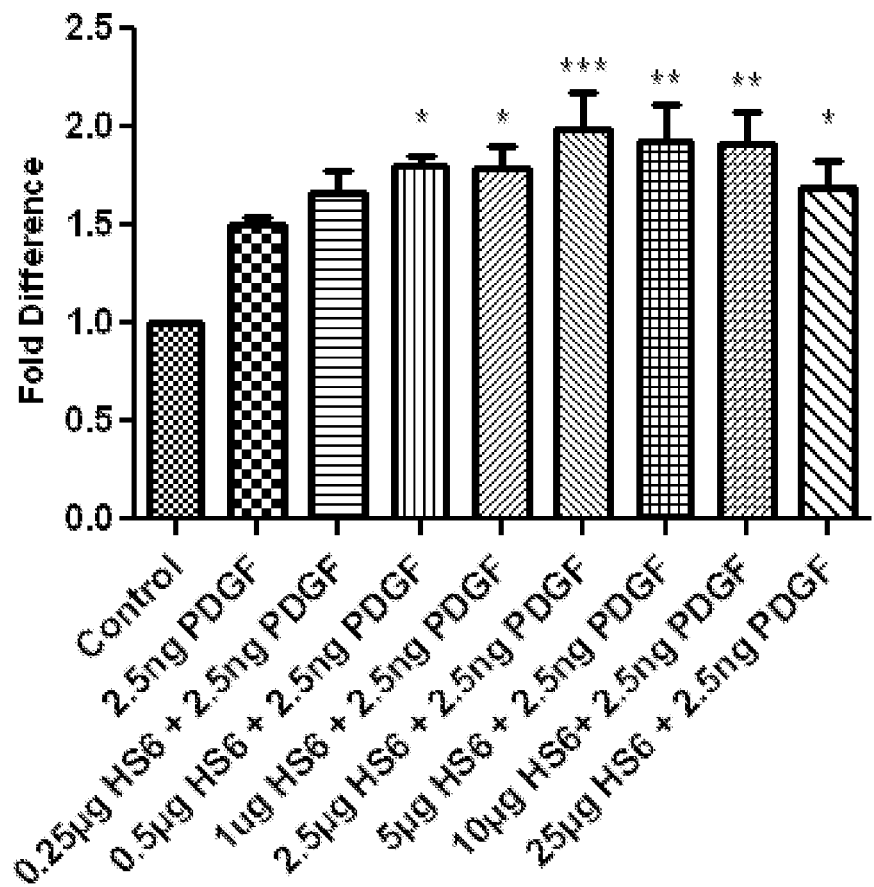

FIG. 29B shows that HS6 drives in vitro proliferation of HDFs by itself, and FIG. 29C shows that HS6 also increases proliferation-promoting effects of PDGF-BB (FIG. 29A) when HS6 and PDGF-BB are used in combination.

Figure 30A:
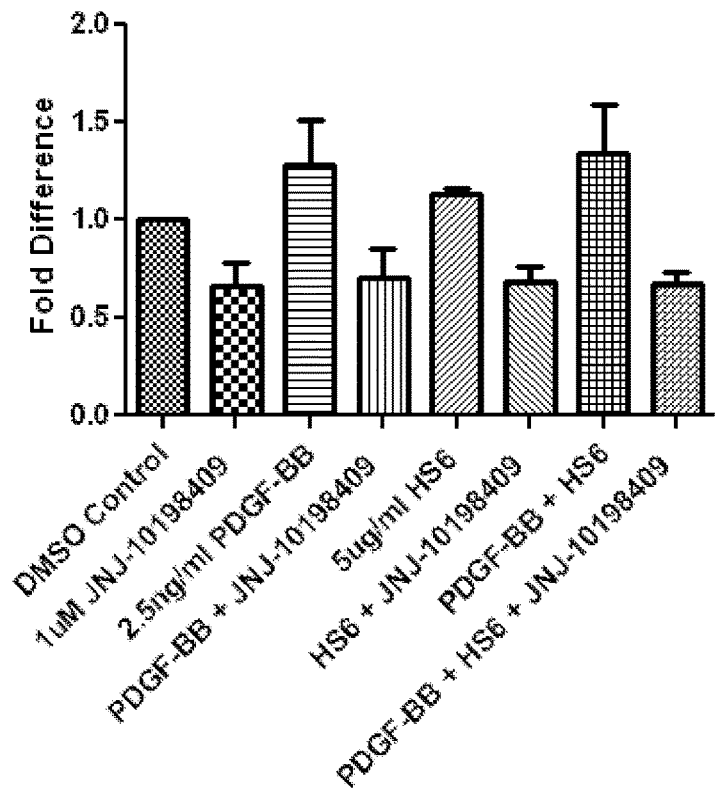
FIG. 30. Charts showing effect of PDGFR and FGFR inhibition. (A) Effect of PDGFR inhibitor JNJ-10198409; (B) Effect of FGFR1 inhibitor SU5402.
Figure 30B:
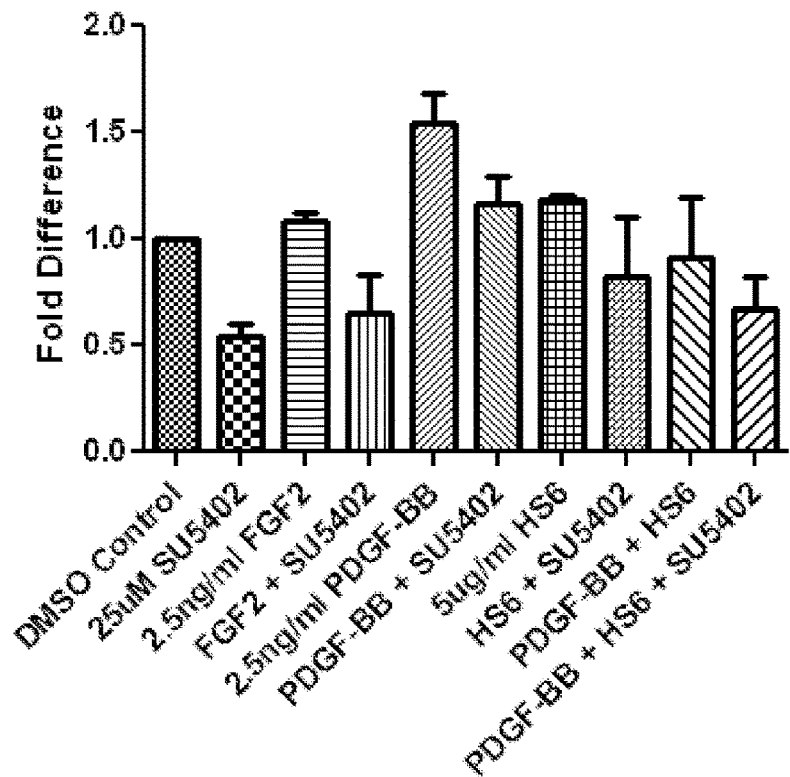

FIGS. 30A and 30B show that stimulation of proliferation is very strongly inhibited in the presence of the PDGF-R inhibitor JNJ-10198409 (FIG. 30A), and is also inhibited—but not as strongly—in the presence of FGFR1 inhibitor SU5402 (FIG. 30B).

Figure 31A:
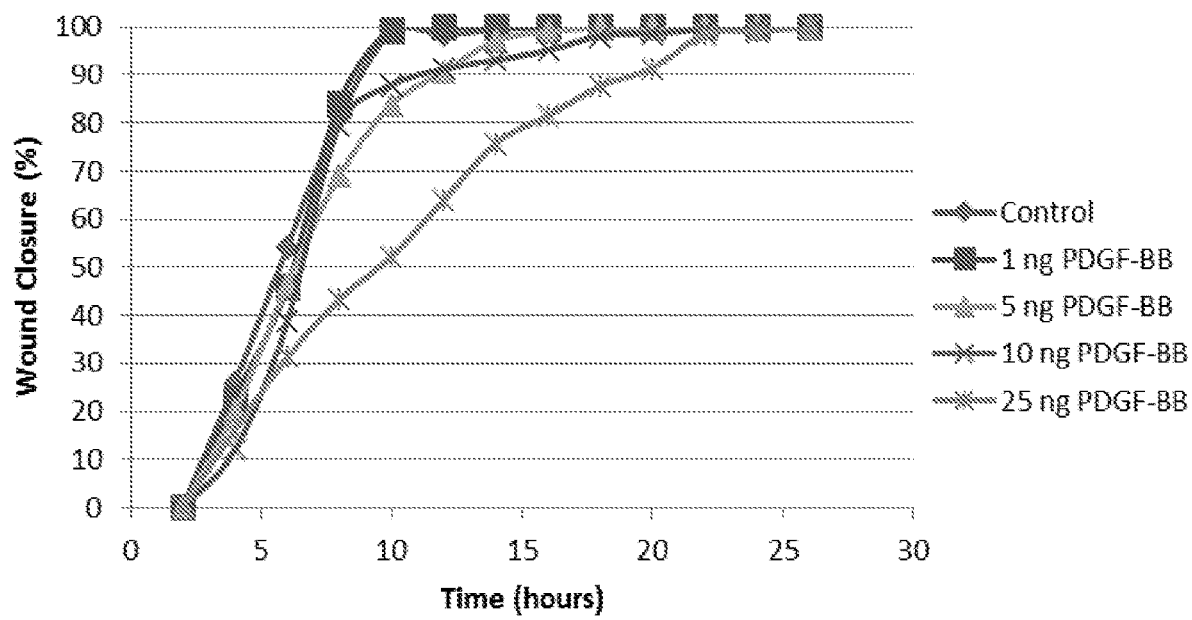
FIG. 31. Charts showing results of scratch wound assay on keratinocytes (N-TERT/1): (A) PDGF-BB (0, 1, 5, 10, 25 ng); (B) HS6 (0, 0.25, 0.5, 1, 2.5, 5, 10, 25 μg).
Figure 31B:
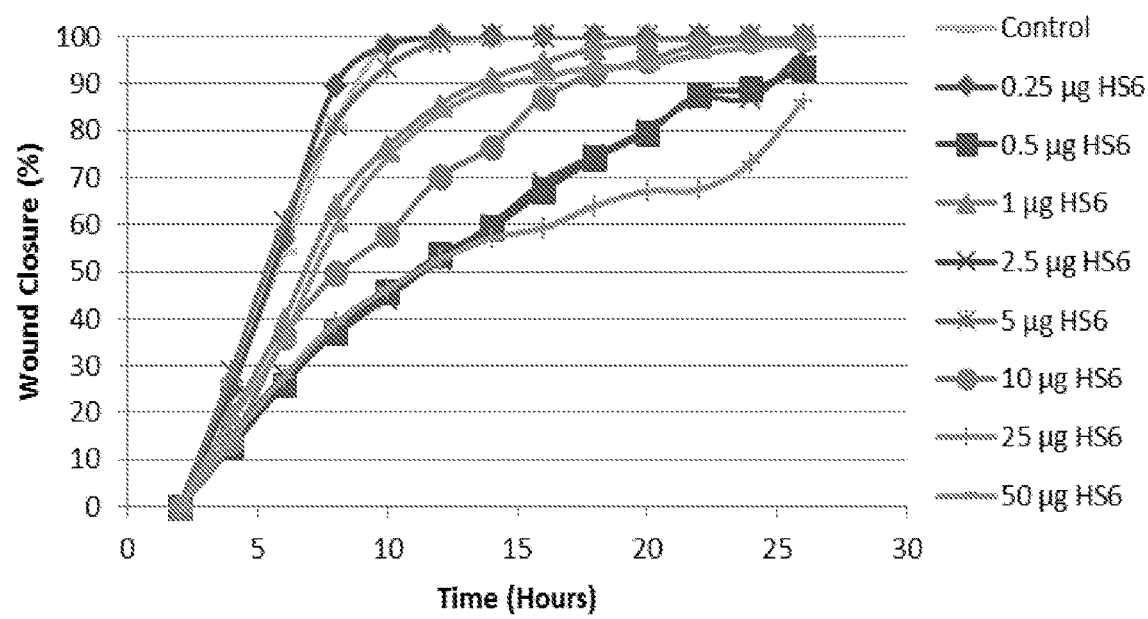
Figure 32:
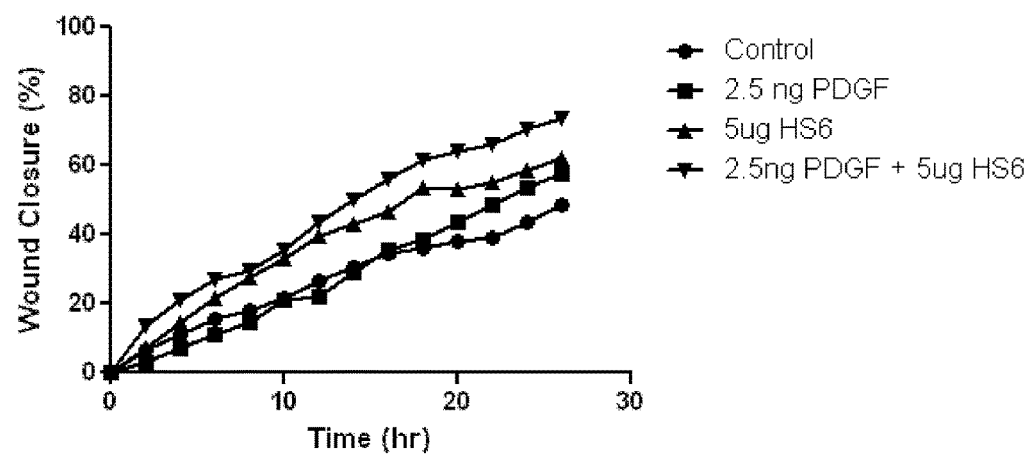
FIG. 32. Chart showing result of scratch wound assay on human dermal fibroblasts.

FIG. 31 shows that when human N-TERT/1 keratinocytes are grown to confluency in vitro, and then scratched using the IncuCyte system, the presence of increasing amounts of HS6, like the PDGF positive control, is able to improve the closure of the "wound" in vitro. The same effect, although less pronounced, is seen for HDFs (FIG. 32).

We thus conclude that HS6 exerts effects both within the epidermis, on keratinocytes, and the dermis, on the dermal fibroblasts.

Example 16: Effects of HS6 on Association of PDGF-BB with PDGFRβ

The influence of HS6 on association between PDGF-BB and PDGFRβ (platelet derived growth factor receptor beta) was investigated by co-immunoprecipitation analysis.

20 µl of protein A/G agarose beads (Santa Cruz) were added to eppendorfs, and 1 µg/mL PDGFRβ-Fc was added to the eppendorfs and immobilised on the beads by rotation at 4° C. for 1 hour. A negative control sample was prepared to which PDGFRβ-Fc was not added. After immobilisation, the beads were washed three times with PBS. Each time, beads were pelleted by centrifugation at 14,000 rpm for 1 min and the supernatant was discarded. 3 µg/mL aliquots of PDGFBB were preincubated with 0, 125, 250 or 500 µg/mL HS6+ on ice, for 10 min. The PDGF-BB/HS mixtures were then applied to the beads. The beads were then washed in PBS three times as above, and finally re-suspended in 40 µl of Laemmli buffer. Samples were boiled for 5 minutes to denature proteins, and then loaded into a 10 well 4-12% Bis-Tris gel, and blotted onto a nitrocellulose membrane. Membranes were blocked, and then incubated with anti-PDGFRβ or anti-PDGF-BB antibodies.

Figure 33:
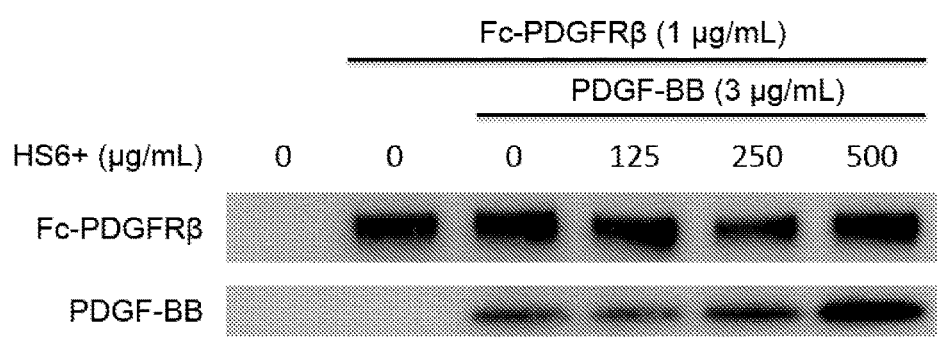
FIG. 33. Photographs showing results of co-immunoprecipitation studies investigating binding of PDGF-BB to Fc-PDGFRβ. HS6+ increases association of PDGF-BB with Fc-PDGFRβ.

FIG. 33 shows the results of the co-immunoprecipitation studies. In the presence of HS6, there is much more association PDGF-BB and PDGFRβ, as can be seen by the increased intensity of the PDGF-BB bands of lanes 4 to 6 (i.e. HS6+ 125, 250 and 500 µg/mL, respectively) relative to the PDGF-BB band of lane 3 (i.e. HS6+0 µg/mL).

The results suggest that HS6+ enhances binding between PDGF-BB and PDGFRβ.

REFERENCES

1. Brickman, Y. G., Ford, M. D., Gallagher, J. T., Nurcombe, V., Bartlett, P. F. & Turnbull, J. E. (1998) Structural modification of fibroblast growth factor-binding heparan sulfate at a determinative stage of neural development. The Journal of Biological Chemistry, 273, 4350-4359.
2. Knobloch, J. E., & Shaklee, P. N. (1997) Absolute molecular weight distribution of low-molecular-weight heparin and heparan sulfate by size-exclusion chromatography with multiangle laser light scattering detection. Analytical Biochemistry, 245, 231-241.
3. Skidmore, M. A., Guimond, S. E., Dumax-Vorzet, A. F., Yates, E. A. & Turnbull, J. E. (2010) Disaccharide compositional analysis of heparan sulfate and heparin polysaccharides using UV or high-sensitivity fluorescence (BODIPY) detection. Nature Protocols, 5 (12), 1983-1992.
4. The effect of controlled release of PDGF-BB from heparin-conjugated electrospun PCL/gelatin scaffolds on cellular bioactivity and infiltration. Lee J, Yoo J J, Atala A, Lee S J. Biomaterials. 2012 33(28):6709-20.
5. Heparan sulfate side chains have a critical role in the inhibitory effects of perlecan on vascular smooth muscle cell response to arterial injury. Gotha L, Lim S Y, Osherov A B, Wolff R, Qiang B, Erlich I, Nili N, Pillarisetti S, Chang Y T, Tran P K, Tryggvason K, Hedin U, Tran-Lundmark K, Advani S L, Gilbert R E, Strauss B H. Am J Physiol Heart Circ Physiol. 2014 Aug. 1; 307(3):H337-45.
6. Priming with proangiogenic growth factors and endothelial progenitor cells improves revascularization in linear diabetic wounds. Ackermann M, Pabst A M, Houdek J P, Ziebart T, Konerding M A. Int J Mol Med. 2014 April; 33(4):833-9.
7. Defective N-sulfation of heparan sulfate proteoglycans limits PDGF-BB binding and pericyte recruitment in vascular development. Abramsson A1, Kurup S, Busse M, Yamada S, Lindblom P, Schallmeiner E, Stenzel D, Sauvaget D, Ledin J, Ringvall M, Landegren U, Kjellén L, Bondjers G, Li J P, Lindahl U, Spillmann D, Betsholtz C, Gerhardt H. Genes Dev. 2007 Feb. 1; 21(3):316-31.

The invention claimed is:

1. A method of treating a disease, condition or injury to skin in a patient, the method comprising administration of a therapeutically effective amount of heparan sulphate HS6 to the patient leading to repair and/or regeneration of the skin, wherein the heparan sulphate HS6 is capable of binding a peptide or polypeptide having, or consisting of, the amino acid sequence RAKTPQTRVTIRTVRVRRPPKGKHRK-FKHTHDK (SEQ ID NO:1);

wherein following digestion with heparin lyases I, II, and III and then subjecting the resulting disaccharide fragments to HPLC analysis, the heparan sulphate HS6 has a disaccharide composition comprising:

| Disaccharide | Normalised weight percentage |
| --- | --- |
| ΔUA,2S-GlcNS,6S | 12.9 ± 3.0 |
| ΔUA,2S-GlcNS | 6.8 ± 2.0 |
| ΔUA-GlcNS,6S | 11.7 ± 3.0 |
| ΔUA-GlcNS | 24.5 ± 3.0 |
| ΔUA,2S-GlcNAc | 0.5 ± 0.5 |
| ΔUA-GlcNAc,6S | 12.1 ± 3.0 |
| ΔUA-GlcNAc | 31.6 ± 3.0. |

2. The method of claim 1 wherein the method comprises administering the heparan sulphate HS6 to tissue at or surrounding a wound or location on the patient's body at which regeneration or repair of skin is required.

3. The method of claim 1, wherein the method further comprises administering PDGF-B, PDGF-BB or a heterodimer comprising PDGF-B to the patient.

4. A method of treating a disease, condition or injury to skin in a patient, the method comprising surgically implanting a biocompatible implant or prosthesis, which implant or prosthesis comprises a biomaterial and heparan sulphate HS6, into tissue of the patient at or surrounding the site of the disease, condition or injury leading to repair and/or regeneration of the skin, wherein the heparan sulphate HS6 is capable of binding a peptide or polypeptide having, or consisting of, the amino acid sequence RAKTPQTRVTIRT-VRVRRPPKGKHRKFKHTHDK (SEQ ID NO:1);

wherein following digestion with heparin lyases I, II, and III and then subjecting the resulting disaccharide fragments to HPLC analysis, the heparan sulphate HS6 has a disaccharide composition comprising:

| Disaccharide | Normalised weight percentage |
| --- | --- |
| ΔUA,2S-GlcNS,6S | 12.9 ± 0.5 |
| ΔUA,2S-GlcNS | 6.8 ± 0.2 |
| ΔUA-GlcNS,6S | 11.7 ± 0.5 |
| ΔUA-GlcNS | 24.6 ± 1.5 |
| ΔUA,2S-GlcNAc | 0.5 ± 0.2 |
| ΔUA-GlcNAc,6S | 12.1 ± 0.5 |
| ΔUA-GlcNAc | 31.6 ± 0.8. |

5. The method of claim 1, wherein following digestion with heparin lyases I, II, and III and then subjecting the resulting disaccharide fragments to HPLC analysis, the heparan sulphate HS6 has a disaccharide composition comprising:

| Disaccharide | Normalised weight percentage |
| --- | --- |
| ΔUA,2S-GlcNS,6S | 12.9 ± 0.5 |
| ΔUA,2S-GlcNS | 6.8 ± 0.2 |
| ΔUA-GlcNS,6S | 11.7 ± 0.5 |
| ΔUA-GlcNS | 24.6 ± 1.5 |
| ΔUA,2S-GlcNAc | 0.5 ± 0.2 |
| ΔUA-GlcNAc,6S | 12.1 ± 0.5 |
| ΔUA-GlcNAc | 31.6 ± 0.8. |

6. The method of claim 1, wherein following digestion with heparin lyases I, II, and III and then subjecting the resulting disaccharide fragments to HPLC analysis, the heparan sulphate HS6 has a disaccharide composition comprising:

| Disaccharide | Normalised weight percentage |
| --- | --- |
| ΔUA,2S-GlcNS,6S | 12.8 ± 0.5 |
| ΔUA,2S-GlcNS | 6.8 ± 0.2 |
| ΔUA-GlcNS,6S | 11.6 ± 0.5 |
| ΔUA-GlcNS | 24.6 ± 0.5 |
| ΔUA,2S-GlcNAc | 0.5 ± 0.1 |
| ΔUA-GlcNAc,6S | 12.0 ± 0.4 |
| ΔUA-GlcNAc | 31.6 ± 0.5. |

7. The method of claim 1, wherein the heparan sulphate HS6 is obtained by a method comprising:

(i) providing a solid support having polypeptide molecules adhered to the support, wherein the polypeptide comprises a heparin-binding domain having the amino acid sequence RAKTPQTRVTIRTVRVRRPPKG-KHRKFKHTHDK (SEQ ID NO:1);

(ii) contacting the solid support with a mixture comprising glycosaminoglycan such that polypeptide-glycosaminoglycan complexes are allowed to form;

(iii) partitioning polypeptide-glycosaminoglycan complexes from the remainder of the mixture;

(iv) dissociating glycosaminoglycans from the polypeptide-glycosaminoglycan complexes; and (v) collecting the dissociated glycosaminoglycans.

8. The method of claim 7, wherein the mixture comprising glycosaminoglycans is a heparan sulphate preparation obtained from porcine mucosa (HSPM).

9. The method of claim 1, wherein the disease, condition or injury to tissue is a skin wound and the method comprises administration of a therapeutically effective amount of heparan sulphate HS6 to the subject leading to repair and/or regeneration of skin at the wound.

10. The method of claim 9, wherein the skin wound is a skin burn, ulcer, excisional wound, cut, stab or puncture wound.

11. The method of claim 9, wherein the method involves skin graft healing, skin reconstruction, or skin plastic surgery.

12. The method of claim 9, wherein the heparan sulphate HS6 is formulated for topical or transdermal administration.

13. The method of claim 9, wherein the method further comprises administration of a growth factor.

14. The method of claim 9, wherein the heparan sulphate HS6 is formulated as a combined preparation with a growth factor.

15. The method of claim 1, wherein the heparan sulphate HS6 is provided in isolated or substantially purified form.

16. The method of claim 4, wherein following digestion with heparin lyases I, II and III and then subjecting the resulting disaccharide fragments to HPLC analysis the heparan sulphate HS6 has a disaccharide composition comprising:

| Disaccharide | Normalised weight percentage |
| --- | --- |
| ΔUA,2S-GlcNS,6S | 12.9 ± 0.5 |
| ΔUA,2S-GlcNS | 6.8 ± 0.2 |
| ΔUA-GlcNS,6S | 11.7 ± 0.5 |
| ΔUA-GlcNS | 24.6 ± 1.5 |
| ΔUA,2S-GlcNAc | 0.5 ± 0.2 |
| ΔUA-GlcNAc,6S | 12.1 ± 0.5 |
| ΔUA-GlcNAc | 31.6 ± 0.8. |

17. The method of claim 4, wherein the heparan sulphate HS6 is obtained by a method comprising:

(i) providing a solid support having polypeptide molecules adhered to the support, wherein the polypeptide comprises a heparin-binding domain having the amino acid sequence RAKTPQTRVTIRTVRVRRPPKG-KHRKFKHTHDK (SEQ ID NO:1);

(ii) contacting the solid support with a mixture comprising glycosaminoglycan such that polypeptide-glycosaminoglycan complexes are allowed to form;

(iii) partitioning polypeptide-glycosaminoglycan complexes from the remainder of the mixture;

(iv) dissociating glycosaminoglycans from the polypeptide-glycosaminoglycan complexes; and (v) collecting the dissociated glycosaminoglycans.

18. The method of claim 1, wherein the heparan sulphate HS6 is capable of binding PDGF-B, PDGF-BB, or both PDGF-B and PDGF-BB.

19. The method of claim 4, wherein the heparan sulphate HS6 is capable of binding PDGF-B, PDGF-BB, or both PDGF-B and PDGF-BB.

20. The method of claim 13, wherein the growth factor is PDGF-B or PDGF-BB, or a heterodimer comprising PDGF-B.

21. The method of claim 1, wherein the heparan sulphate HS6 is capable of stimulating the proliferation of dermal fibroblasts and keratinocytes.

22. The method of claim 4, wherein the heparan sulphate HS6 is capable of stimulating the proliferation of dermal fibroblasts and keratinocytes.

* * * * *

UNITED STATES PATENT AND TRADEMARK OFFICE
CERTIFICATE OF CORRECTION

PATENT NO. : 10,723,813 B2
APPLICATION NO. : 15/542123
DATED : July 28, 2020
INVENTOR(S) : Simon Cool et al.

It is certified that error appears in the above-identified patent and that said Letters Patent is hereby corrected as shown below:

In the Claims

In Claim 4, Column 47, Line 48-54, please delete:

| "Disaccharide | Normalised weight percentage |
|---|---|
| $\Delta$UA,2S-GlcNS,6S | 12.9 ±0.5 |
| $\Delta$UA,2S-GlcNS | 6.8 ±0.2 |
| $\Delta$UA-GlcNS,6S | 11.7±0.5 |
| $\Delta$UA-GlcNS | 24.6 ±1.5 |
| $\Delta$UA,2S-GlcNAc | 0.5 ±0.2 |
| $\Delta$UA-GlcNAc,6S | 12.1 ±0.5 |
| $\Delta$UA-GlcNAc | 31.6 ±0.8" |

And insert:

| --Disaccharide | Normalised weight percentage |
|---|---|
| $\Delta$UA,2S-GlcNS,6S | 12.9 ±3.0 |
| $\Delta$UA,2S-GlcNS | 6.8 ±0.2 |
| $\Delta$UA-GlcNS,6S | 11.7±3.0 |
| $\Delta$UA-GlcNS | 24.5 ±3.0 |
| $\Delta$UA,2S-GlcNAc | 0.5 ±0.5 |
| $\Delta$UA-GlcNAc,6S | 12.1 ±3.0 |
| $\Delta$UA-GlcNAc | 31.6 ±3.0-- |

Signed and Sealed this
Sixteenth Day of March, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 3

<210> SEQ ID NO 1
<211> LENGTH: 33
<212> TYPE: PRT
<213> ORGANISM: Homo sapiens

<400> SEQUENCE: 1

Arg Ala Lys Thr Pro Gln Thr Arg Val Thr Ile Arg Thr Val Arg Val
1               5                   10                  15

Arg Arg Pro Pro Lys Gly Lys His Arg Lys Phe Lys His Thr His Asp
            20                  25                  30

Lys

<210> SEQ ID NO 2
<211> LENGTH: 35
<212> TYPE: PRT
<213> ORGANISM: Artificial sequence
```

```
<220> FEATURE:
<223> OTHER INFORMATION: Biotinylated PDGF-BB peptide
<220> FEATURE:
<221> NAME/KEY: SITE
<222> LOCATION: (1)..(1)
<223> OTHER INFORMATION: Lys(Biotin)
<220> FEATURE:
<221> NAME/KEY: MOD_RES
<222> LOCATION: (2)..(2)
<223> OTHER INFORMATION: Acp

<400> SEQUENCE: 2

Lys Lys Arg Ala Lys Thr Pro Gln Thr Arg Val Thr Ile Arg Thr Val
1               5                   10                  15
Arg Val Arg Pro Pro Lys Gly Lys His Arg Lys Phe Lys His Thr
            20                  25                  30
His Asp Lys
        35

<210> SEQ ID NO 3
<211> LENGTH: 241
<212> TYPE: PRT
<213> ORGANISM: Homo sapiens

<400> SEQUENCE: 3

Met Asn Arg Cys Trp Ala Leu Phe Leu Ser Leu Cys Cys Tyr Leu Arg
1               5                   10                  15
Leu Val Ser Ala Glu Gly Asp Pro Ile Pro Glu Glu Leu Tyr Glu Met
            20                  25                  30
Leu Ser Asp His Ser Ile Arg Ser Phe Asp Asp Leu Gln Arg Leu Leu
        35                  40                  45
His Gly Asp Pro Gly Glu Glu Asp Gly Ala Glu Leu Asp Leu Asn Met
    50                  55                  60
Thr Arg Ser His Ser Gly Gly Glu Leu Glu Ser Leu Ala Arg Gly Arg
65                  70                  75                  80
Arg Ser Leu Gly Ser Leu Thr Ile Ala Glu Pro Ala Met Ile Ala Glu
                85                  90                  95
Cys Lys Thr Arg Thr Glu Val Phe Glu Ile Ser Arg Arg Leu Ile Asp
            100                 105                 110
Arg Thr Asn Ala Asn Phe Leu Val Trp Pro Pro Cys Val Glu Val Gln
        115                 120                 125
Arg Cys Ser Gly Cys Cys Asn Asn Arg Asn Val Gln Cys Arg Pro Thr
    130                 135                 140
Gln Val Gln Leu Arg Pro Val Gln Val Arg Lys Ile Glu Ile Val Arg
145                 150                 155                 160
Lys Lys Pro Ile Phe Lys Lys Ala Thr Val Thr Leu Glu Asp His Leu
                165                 170                 175
Ala Cys Lys Cys Glu Thr Val Ala Ala Ala Arg Pro Val Thr Arg Ser
            180                 185                 190
Pro Gly Gly Ser Gln Glu Gln Arg Ala Lys Thr Pro Gln Thr Arg Val
        195                 200                 205
Thr Ile Arg Thr Val Arg Val Arg Arg Pro Pro Lys Gly Lys His Arg
    210                 215                 220
Lys Phe Lys His Thr His Asp Lys Thr Ala Leu Lys Glu Thr Leu Gly
225                 230                 235                 240
Ala
```